US008252782B2

(12) United States Patent
Brickner et al.

(10) Patent No.: US 8,252,782 B2
(45) Date of Patent: Aug. 28, 2012

(54) MONOCARBAMS

(75) Inventors: Steven Joseph Brickner, Ledyard, CT (US); Mark Edward Flanagan, Gales Ferry, CT (US); Manjinder Singh Lall, East Lyme, CT (US)

(73) Assignee: Pfizer Inc., New York, NY (US)

( * ) Notice: Subject to any disclaimer, the term of this patent is extended or adjusted under 35 U.S.C. 154(b) by 369 days.

(21) Appl. No.: 12/641,343

(22) Filed: Dec. 18, 2009

(65) Prior Publication Data

US 2010/0160281 A1    Jun. 24, 2010

Related U.S. Application Data

(60) Provisional application No. 61/139,159, filed on Dec. 19, 2008.

(51) Int. Cl.
*C07D 417/14* (2006.01)
*A61K 31/4439* (2006.01)
*A61P 31/04* (2006.01)
*C07D 413/04* (2006.01)
*C07D 401/04* (2006.01)
*C07D 213/81* (2006.01)
*C07D 417/12* (2006.01)

(52) U.S. Cl. ............... 514/210.02; 540/353; 546/269.4; 546/272.4; 546/296; 548/128; 548/196; 549/417

(58) Field of Classification Search ................. 540/363; 514/210.02
See application file for complete search history.

(56) References Cited

U.S. PATENT DOCUMENTS

| 4,587,047 A | 5/1986 | Breuer et al. | 260/239 |
| 4,762,922 A * | 8/1988 | Breuer et al. | 540/363 |
| 4,777,252 A | 10/1988 | Slusarchyk et al. | 540/363 |
| 4,959,470 A | 9/1990 | Treuner | 540/363 |
| 4,975,538 A | 12/1990 | Barbachyn et al. | 540/363 |
| 5,001,235 A * | 3/1991 | Kim | 540/363 |
| 5,006,650 A | 4/1991 | Barbachyn | 540/363 |
| 5,015,737 A * | 5/1991 | Kim | 540/363 |

FOREIGN PATENT DOCUMENTS

| EP | 0062876 | 10/1982 |
| EP | 0281289 | 9/1988 |
| EP | 0321844 | 6/1989 |
| EP | 0336369 | 10/1989 |
| EP | 0344707 | 12/1989 |
| EP | 0344197 | 8/1991 |
| WO | WO 8806588 | 9/1988 |
| WO | WO 9003376 | 4/1990 |
| WO | 2008/116813 | 10/2008 |

OTHER PUBLICATIONS

Page, Antimicrobial Agents and Chemotherapy, Jun. 2010, p. 2291-2302.*
Cascio, et al., "Synthesis and Antibacterial Activity of C-4-Thio- and Dithiocarbamate Monobactam Derivatives", *Il Pharmaco*, vol. 51(3), pp. 189-196 (1996).
Arnould, et al., "Synthesis and antibacterial activity of C4 substituted monobactams", *Eur. J. Med. Chem.*, vol. 27(2), pp. 131-140 (1992).
Kirrstetter, et al., "Development of new β-lactam antibiotics derived from natural and synthetic sources", *Die Pharamzie*, vol. 44(3), pp. 177-185 (1989).
Barbachyn, et al., "Synthesis and Structure-Activity Relationships of Monocarbams Leading to U-78608", *J. Antibiotics*, vol. 43(9), pp. 1199-1203 (1990).
Zurenko, et al., "In Vitro Antibacterial Activity and Interactions with β-Lactamases and Penicillin-Binding Proteins of the New Monocarbam Antibiotic U-78608", *Antimicrobial Agents and Chemotherapy*, vol. 34(5), pp. 884-888 (1990).
Kim, et al., "Synthesis and Structure-Activity Relationshipsa of C-4-Amino Acid Substituted Monobactam Analogs", *J. Antibiotics*, vol. 40(1), pp. 124-129 (1987).
Castanheira M, Deshpande LM, Mathai D, Bell JM, Jones RN, Mendes RE (2011). Early dissemination of NDM-1- and OXA-181-producing Enterobacteriaceae in Indian hospitals: Report from the SENTRY Antimicrobial Surveillance Program, 2006-2007. Antimicrob Agents Chemother 55: 1274-1278.
Castanheira M, Mendes RE, Rhomberg PP, Jones RN (2008). Rapid emergence of blaCTX-M among Enterobacteriaceae in U.S. Medical Centers: molecular evaluation from the MYSTIC Program (2007). Microb Drug Resist 14: 211-216.
Giamarellou H, Poulakou G (2009). Multidrug-resistant Gram-negative infections: What are the treatment options? Drugs 69: 1879-1901.
Livermore DM (2009). Has the era of untreatable infections arrived? J Antimicrob Chemother 64 Suppl 1: i29-i36.
CLSI. Clinical and Laboratory Standards Institute Methods for Dilution Antimicrobial Susceptibility Tests for Bacteria That Grow Aerobically; Approved Standard-Eighth Edition, CLSI document M07-A8 with Abstract, Wayne PA: Clinical and Laboratory Standards Institute, Jan. 2009, pp. i, vii, viii, ix, x, xi, xii, 1, and 65, 29(2).
CLSI. Clinical and Laboratory Standards Institute "Performance Standards for Antimicrobial Susceptibility Testing: Twenty-First Informational Supplement", CLSI document M100-S21, Wayne PA: Clinical and Laboratory Standards Institute, Jan. 2011, pp. 1, 4, 9, 10-20, 162-162, 31(1).

* cited by examiner

*Primary Examiner* — Mark Berch
(74) *Attorney, Agent, or Firm* — John A. Wichtowski

(57) ABSTRACT

The invention relates to compounds of formula (I):

(I)

wherein $R^1$, $R^2$, $R^3$, $R^4$, $R^5$, and $R^6$ as defined herein. The invention also relates to pharmaceutical compositions and methods of treating bacterial infections using compounds of formula (I).

25 Claims, No Drawings

MONOCARBAMS

FIELD OF THE INVENTION

The present invention relates to Monocarbam compounds and their use as antibacterial agents in animals, including humans. The invention also relates to methods of preparing compounds, intermediates useful in preparing compounds, and pharmaceutical compositions containing compounds. The present invention further includes methods of treating disease, e.g., bacterial infections by administering compounds or compositions to subjects in need of such treatment.

BACKGROUND OF THE INVENTION

Monocarbams are a class of synthetic monocyclic beta-lactam antibacterial agents which have as their salient feature, a substituted sulfonylaminocarbonyl activating group at the N–1 position. The early studies in this area were conducted by workers at the Squibb Institute for Medical Research, Cimarusti, C. M. & R. B. Sykes: Monocyclic β-lactam antibiotics. Med. Res. Rev. 4: 17~20, 1984. Monocarbams have also been previously discussed in EP 0281289, published Sep. 7, 1988. These and all documents cited herein are fully incorporated in their entirety by reference herein.

Although not limiting to the present invention, it is believed that monocarbams of the present invention exploit the iron uptake mechanism in bacteria through the use of siderphore-monobactam and siderphore-monocarbam conjugates. Barbachyn, M. R., Tuominen, T. C.: Synthesis And Structure-Activity Relationships of Monocarbams Leading to U-78608. Journal of Antibiotics Vol. XLIII No. 9: 1199-1203, 1990. Thus, at least in general terms, the activity and mechanism of action of monocarbams are generally known, although the present invention is not bound or limited by any theory.

There is a continuing need for new antibiotics, such as monocarbams, in response to the increasing emergence of resistant organisms and to improve safety, among other reasons.

SUMMARY OF THE INVENTION

The present invention relates to certain compounds of formula (I), their preparation and useful intermediates, pharmaceutical compositions thereof, and methods of treating and preventing bacterial infections therewith. In many embodiments, the compounds are active and effective against organisms that are resistant to other antibiotics.

In particular, the present invention relates to a compound of formula (I):

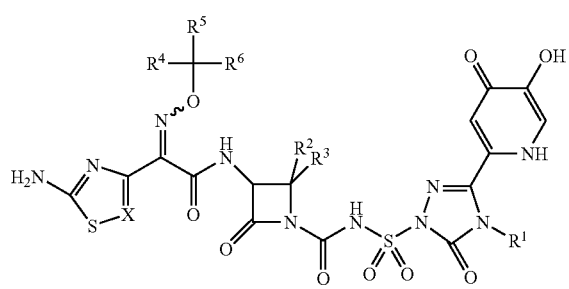

(I)

or pharmaceutically acceptable salt thereof; wherein $R^1$ is $(C_1-C_6)$alkyl substituted with 1 to 3 substituents selected from the group consisting of halo, hydroxy, $(C_1-C_6)$alkoxy, $-NR^7R^8$, $-C(=O)NR^7R^8$, and a 3 to 7 membered heterocycle, wherein $R^7$ and $R^8$ are independently hydrogen or $(C_1-C_6)$alkyl, wherein said heterocycle contains 1 to 3 heteroatoms independently selected from O, N, or S;

$R^2$ is hydrogen or methyl;

$R^3$ is hydrogen or methyl;

$R^4$ is hydrogen, deuterium, or methyl optionally substituted with 1 to 3 substituents independently selected from F or Cl;

$R^5$ is hydrogen, deuterium or methyl optionally substituted with 1 to 3 substituents independently selected from F or Cl;

$R^6$ is H or $-C(=O)OH$; and

X is C(H), C(F), C(Cl), or N.

In one embodiment, the compound of formula (I) has the formula (IA):

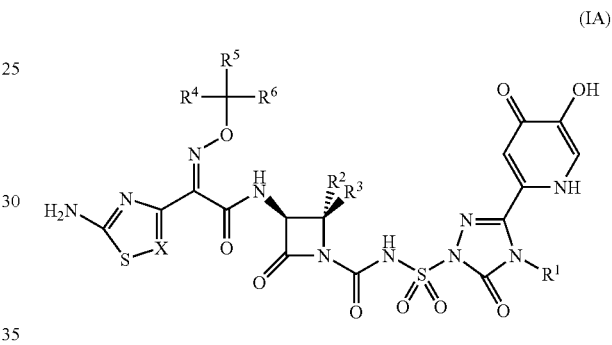

(IA)

or pharmaceutically acceptable salt thereof. In one embodiment $R^4$ is methyl optionally substituted with 1 to 3 substituents selected from F or Cl. In another embodiment $R^4$ is hydrogen. In another embodiment $R^5$ is methyl optionally substituted with 1 to 3 substituents selected from F or Cl. In another embodiment $R^5$ is hydrogen. In another embodiment $R^6$ is $-C(=O)OH$. In another embodiment $R^6$ is hydrogen. In another embodiment X is C(F). In another embodiment X is C(H).

In another embodiment X is C(Cl). In another embodiment X is N. In another embodiment $R^2$ is hydrogen. In another embodiment $R^2$ is methyl. In another embodiment $R^3$ is hydrogen. In another embodiment $R^3$ is methyl.

In yet another embodiment, $R^2$ is hydrogen; $R^3$ is hydrogen; $R^4$ is methyl; $R^5$ is methyl; $R^6$ is $-C(=O)OH$; and X is C(H). In another embodiment, additionally $R^1$ is $(C_1-C_6)$alkyl substituted with 1 to 3 substituents selected from the group consisting of halo, hydroxy, $-NH_2$, $-C(=O)NH_2$, and a 3 to 7 membered heterocycle, wherein said heterocycle contains 1 to 3 heteroatoms independently selected from O, N, or S. Alternatively, in another embodiment, $R^1$ is $(C_1-C_6)$alkyl substituted with 1 to 3 halo. Alternatively, in another embodiment, $R^1$ is $(C_1-C_6)$alkyl substituted with 1 to 3 hydroxy. Alternatively, in another embodiment, $R^1$ is $(C_1-C_6)$alkyl substituted with 1 to 3 $NH_2$. Alternatively, in another embodiment, $R^1$ is $(C_1-C_6)$alkyl substituted with $-C(=O)NH_2$. Alternatively, in another embodiment, $R^1$ is a 3-7 membered heterocycle, wherein said heterocycle contains 1 to 3 heteroatoms independently selected from O, N, or S.

In one particular embodiment, the invention is:

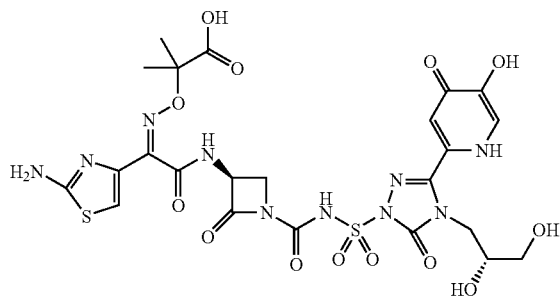

or a pharmaceutically acceptable salt thereof.
In another particular embodiment, the invention is:

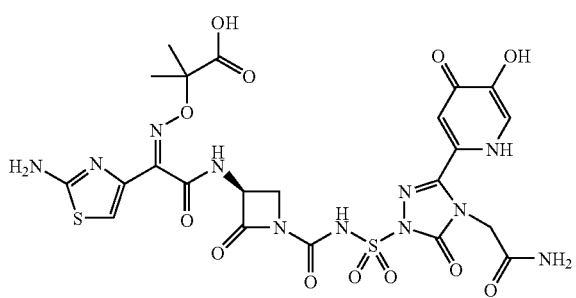

or a pharmaceutically acceptable salt thereof.
In another particular embodiment, the invention is:

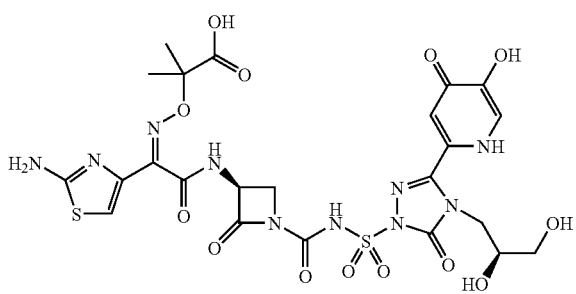

or a pharmaceutically acceptable salt thereof.
In another particular embodiment, the invention is:

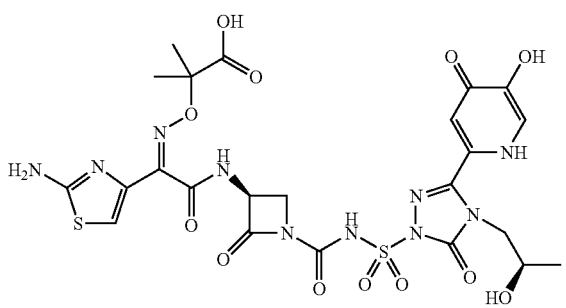

or a pharmaceutically acceptable salt thereof.

In another particular embodiment, the invention is:

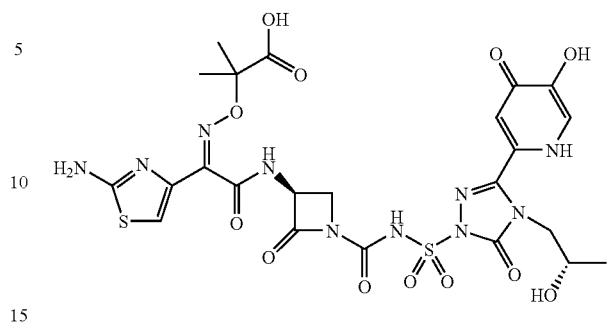

or a pharmaceutically acceptable salt thereof.
In another embodiment, the compound of formula I has the formula (IB):

(IB)

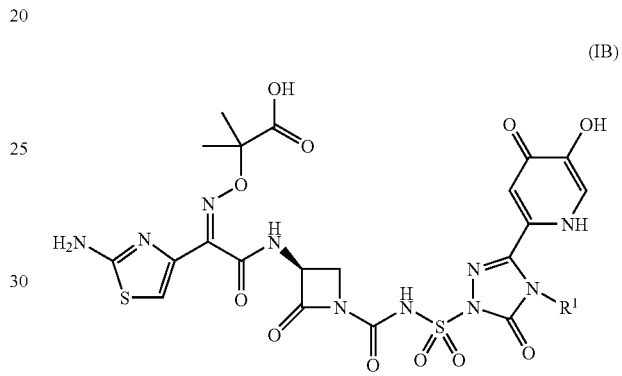

wherein $R^1$ is selected from the group consisting of:

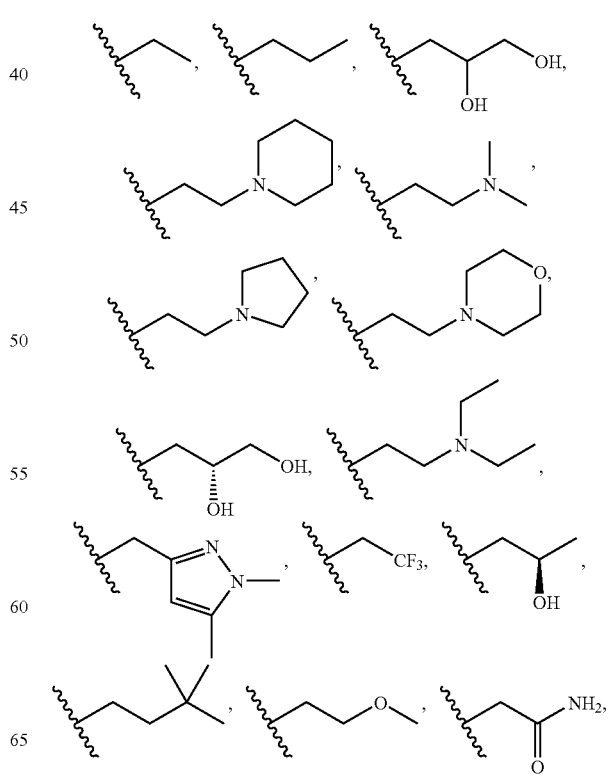

-continued

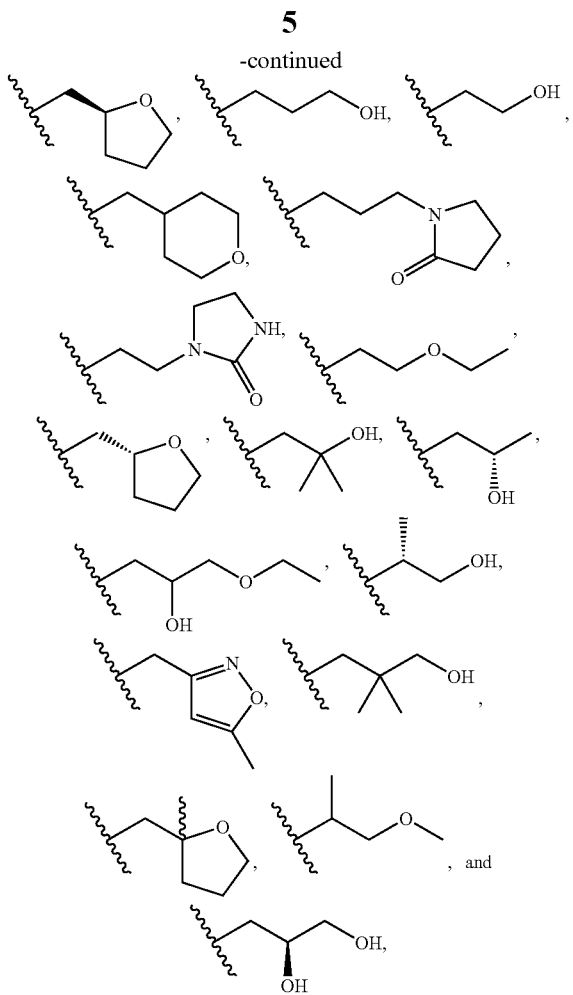

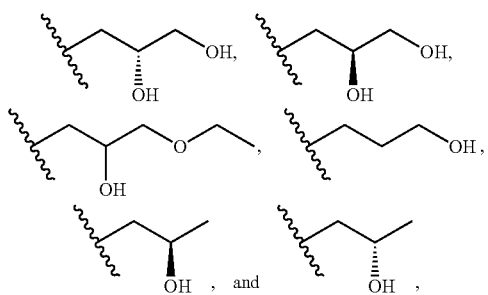

and pharmaceutically acceptable salts thereof.

In one embodiment the invention is a compound of formula (IB) wherein $R^1$ is selected from the group consisting of:

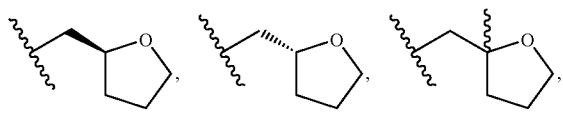

and pharmaceutically acceptable salts thereof.

In another embodiment the invention is a compound of formula (IB) wherein $R^1$ is selected from the group consisting of:

-continued

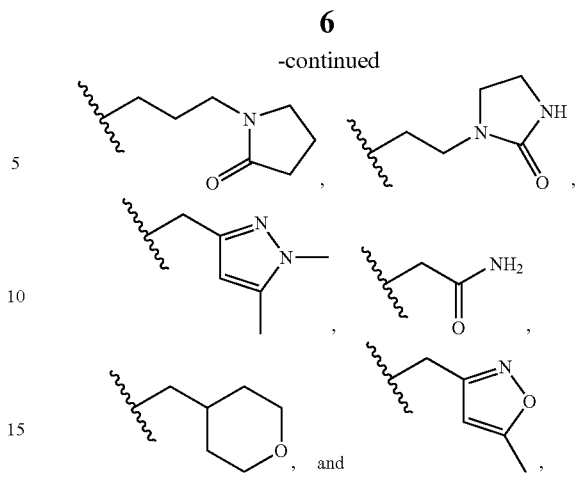

and pharmaceutically acceptable salts thereof.

In another embodiment the invention is a compound of formula (IB) wherein $R^1$ is selected from the group consisting of:

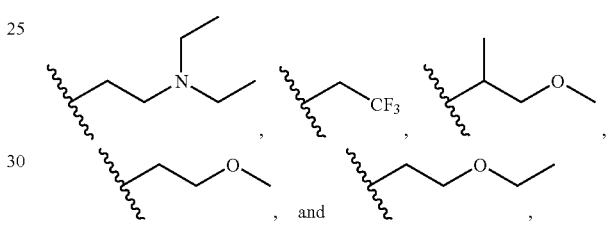

and pharmaceutically acceptable salts thereof.

In another embodiment the invention is a compound of formula (IB) wherein $R^1$ is selected from the group consisting of:

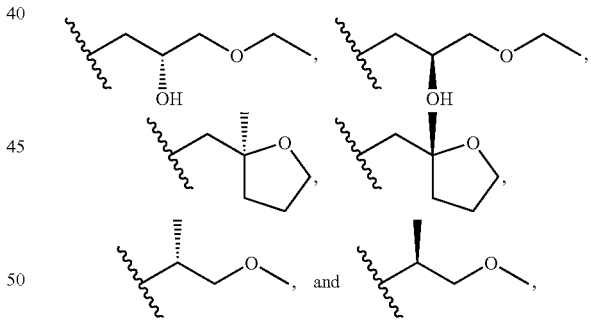

and pharmaceutically acceptable salts thereof.

In one embodiment, the pharmaceutically acceptable salt of compounds of the invention is a potassium or sodium salt.

In one embodiment, the pharmaceutically acceptable salt of compounds of the invention is a bis-potassium or bis-sodium salt.

In another embodiment, the invention is a pharmaceutical composition comprising the compounds described above, or pharmaceutically acceptable salt thereof, and a pharmaceutically acceptable carrier.

In another embodiment, the invention is a method for the treatment of a bacterial infection in a mammal comprising administering to said mammal an amount of a compound of formula (I) or pharmaceutically acceptable salt thereof that is effective in treating a bacterial infection. In one particular embodiment the bacterial infection is resistant or susceptible. In another particular embodiment, the bacterial infection is MDR (multi-drug resistant). In one embodiment, the bacterial infection is selected from the group consisting of respiratory tract infections, lung infection in cystic fibrosis patients, complicated urinary tract infections, burn infections, wound infections, blood infections, complicated skin and soft tissue infections, nail infections, ear infections, infections caused from medical devices, infections caused from a catheter, noscomial pneumonia, ventilator-associated pneumonia (VAP), community-acquired pneumonia (CAP), bacteremia, hot-tub rash (dermatitis), and post-operative infection in radial keratotomy surgery in humans. In another embodiment, the bacterial infection is selected from the group consisting of Nosocomial pneumonia, ventilator-associated pneumonia (VAP), complicated UTI (urinary tract infection), complicated skin and skin structure, and bacteremia. In another embodiment, the bacterial infection is a burn infection. In another embodiment, the bacterial infection is a lung infection in cystic fibrosis patients.

The present invention also relates to a method of treating infection caused by *Pseudomonas aeruginosa*, *Escherichia coli*, a *Klebsiella* species, or an *Acinetobacter* species, comprising administering a therapeutically effective amount of the compound of formula (I) or pharmaceutically acceptable salt thereof to a mammalian subject in need thereof. In one particular embodiment, the infection is caused by *Pseudomonas aeruginosa*.

The present invention also relates to a method of treating infection by *Pseudomonas aeruginosa* that is resistant to doripenem, meropenem or piperacillin comprising administering a therapeutically effective amount of the compound of formula (I) or pharmaceutically acceptable salt thereof to a mammalian subject in need thereof.

The present invention also relates to a composition comprising a compound of formula (I), or pharmaceutically acceptable salt thereof, and an additional antibacterial agent selected from the group consisting of beta-lactams, aminoglycosides, polymyxins, penicillins, and lincosamides. In one embodiment, the additional antibacterial agent is a beta-lactam selected from the group consisting of cephalosporins, carbapenems, and beta-lactamase inhibitors or beta-lactam/beta-lactamase inhibitor combinations. In another embodiment, the additional antibacterial agent is selected from the group consisting of clindamycin, metronidazole, imipenem, meropenem, doripenem, ertapenem, cefotetan, cefepime, and cefpirome, or a third generation cephalosporin. In one particular embodiment, the additional antibacterial agent is cefepime. In another embodiment, the addition antibacterial agent is meropenem. In another embodiment of the composition, the compound is:

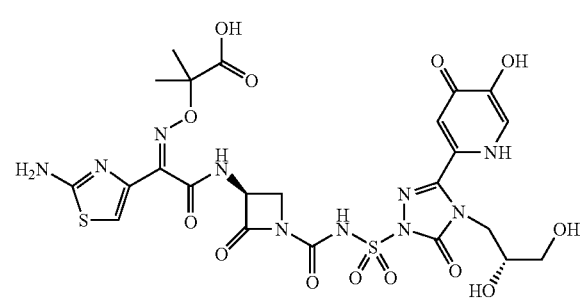

or a pharmaceutically acceptable salt thereof. In another embodiment of the composition, the compound is:

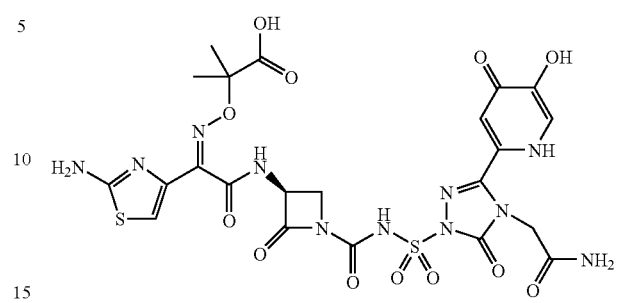

or pharmaceutically acceptable salt thereof. In another embodiment of the composition, the compound is:

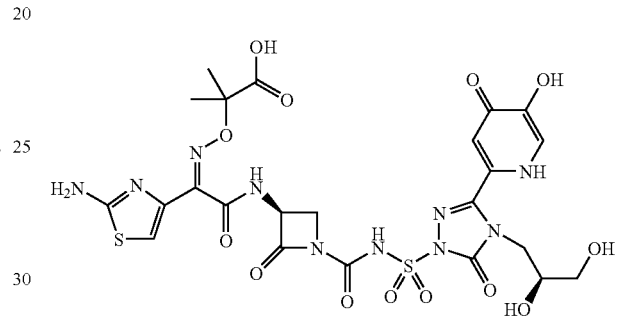

or pharmaceutically acceptable salt thereof. In another embodiment of the composition, the compound is:

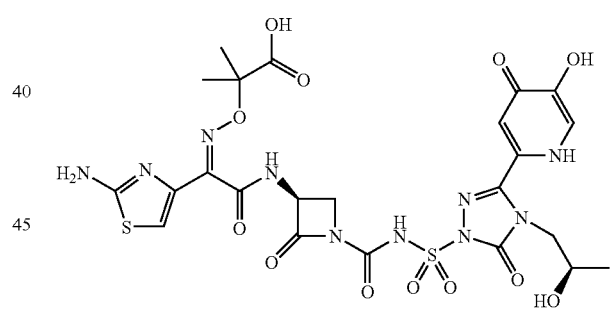

or pharmaceutically acceptable salt thereof. In another embodiment of the composition, the compound is:

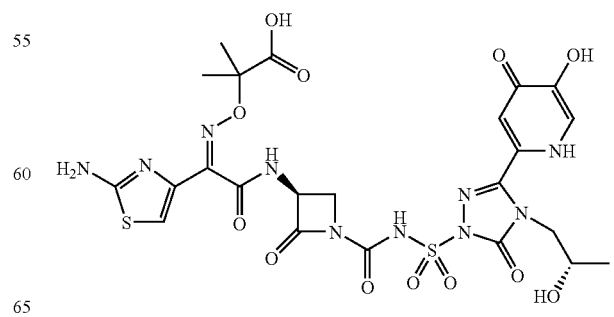

or pharmaceutically acceptable salt thereof.

In another embodiment, the composition is one of the specific compounds shown above and the additional antibacterial agent is cefepime.

In another embodiment, the composition is one of the specific compounds shown above and the additional antibacterial agent is meropenem.

The present invention also relates to a complex or chelate comprising a compound of formula (I) or a pharmaceutically acceptable salt thereof, as a ligand and an iron (+3) cation, wherein the ratio of ligand to iron cation is from about 1:1 to about 3:1, respectively. In one embodiment, the ratio is about 3:1.

The present invention includes methods of treatment of the human or non-human animal body, e.g., to combat or treat (including prevention) bacterial infections, comprising administering to subjects a useful or effective amount of a compound of the invention, including a physiologically acceptable salt or solvate thereof, and including compositions.

The compounds of the invention can also be combined with other active ingredients as desired to attain combination therapy for more than one condition or biological target. For example, the compounds of the invention can be combined with other anti-infectives, or agents that increase the efficacy or other properties of the anti-infective, e.g., efflux inhibitors.

The compounds of formula (I) are useful for treating a patient suffering from a disorder such as, e.g., a bacterial infection.

Bacterial infections amenable to treatment by compounds of formula (I), pharmaceutical compositions, and methods of the present invention include those caused by *Acinetobacter baumannii, Acinetobacter* spp., *Bacteroides fragilis, Citrobacter diversus, Citrobacter freundii, Enterobacter aerogenes, Enterobacter cloacae, Escherichia coli, Haemophilus influenzae* β-lactamase negative, *Haemophilus influenzae* β-lactamase positive, *Klebsiella oxytoca, Klebsiella pneumoniae* (including those encoding extended-spectrum β-lactamases (hereinafter "ESBLs"), *Legionella pneumophila, Moraxella catarrhalis* β-lactamase-negative, *Moraxella catarrhalis* β-positive, *Morganella morganii, Neisseria meningitidis, Prevotella* spp. (and members of the Enterobacteriaceae that express ESBLs and AmpC-type beta-lactamases that confer resistance to currently available cephalosporins, cephamycins and beta-lactam/beta-lactamase inhibitor combinations), *Proteus mirabilis, Pseudomonas aeruginosa, Salmonella/Shigella*, and *Serratia marcescens*.

The compounds of formula (I) may, in one embodiment, be used to treat a variety of hospital and community acquired infections such as respiratory tract infections (including lung infection in cystic fibrosis patients), complicated urinary tract infections, burn infections, wound infections, blood infections, complicated skin and soft tissue infections, nail and ear infections, infections caused from medical devices (e.g., catheter, etc.), noscomial pneumonia (including ventilator-associated pneumonia (VAP)), community-acquired pneumonia (CAP), bacteremia, "hot-tub rash" (dermatitis), and post-operative infection in radial keratotomy surgery in humans (hereinafter "the infections").

In one embodiment, the infection is selected from the group consisting of noscomial pneumonia, ventilator-associated pneumonia, complicated urinary tract infections, complicated skin & skin structure infections, and bacteremia.

In one embodiment, the composition of the invention comprises a therapeutically effective amount of a compound of formula (I) of the invention.

The invention also relates to compositions of the invention which comprise any combination of one or more compounds of formula (I) and at least one additional ingredient (hereinafter "the compositions of the invention").

Non-limiting examples of the at least one additional ingredient include impurities (e.g., intermediates present in the unrefined compounds of formula (I)), active or pharmaceutical agents as discussed below (e.g., another antibacterial agent), pharmaceutically acceptable excipients, or one or more solvents (e.g., a pharmaceutically acceptable carrier as discussed herein).

Compositions of the invention that are suitable for administration to a patient in need thereof (e.g., a human) are also referred to herein as "pharmaceutical compositions of the invention."

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration. In one particular embodiment, the method of administration is intravenous.

The pharmaceutical composition may, for example, be in a form suitable for oral administration as a tablet, capsule, pill, powder, sustained release formulation, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Reminaton's Pharmaceutical Sciences*, Mack Publishing Company, Easter, Pa., 15th Edition (1975).

The minimum amount of the compounds of formula (I) to be administered is a therapeutically effective amount. The term "therapeutically effective amount" means the amount of compound which prevents the onset of, alleviates the symptoms of, stops the progression of, and/or eliminates a bacterial infection in a mammal, e.g., a human.

Typically, an effective dosing schedule of the compounds of formula (I) of the invention for adults is about 50 mg to about 3000 mg of a compound of formula (I) in a single dose; in another embodiment, an effective single dose is about 100 mg to about 2000 mg. In another embodiment, an effective single dose is about 800 mg to about 1000 mg. Typically the dosages are given 1 to 4 times per day. In one embodiment, the dosages are given 3 times per day. In some cases, it may be necessary to use dosages outside these limits.

The compounds of formula (I) of the invention may be administered in combination with one or more additional medicinal or pharmaceutical agents ("the additional active agent"). Such use of the compounds of formula (I) in combination with an additional active agent may be for simultaneous, separate or sequential use.

In one embodiment, the additional active agent is an antibacterial agent.

In one embodiment the antibacterial agent is a β-lactam. Non-limiting examples of β-lactams include cephalosporins (e.g., cefepime, ceftazidime, cefpirome, cefditoren pivoxil (Spectracef®), cefoperazone, ceftazidime, cefdinir, cefotaxime, cefpodoxime, cephalothin, cefaclor or cefixime), cephamycins (e.g., cefotetan), carbapenems (e.g., imipenem, meropenem, ertapenem, doripenem), beta-lactamase inhibitors and beta-lactam/beta-lactamase inhibitor combinations such as sulbactam, clavulanic acid, tazobactam and piperacillin in combination with tazobactam (Zosyn®), and sulopenum.

In another embodiment the antibacterial agent is may be selected from aminoglycosides (e.g., amikacin, gentamicin, kanamycin, neomycin, netilmicin, paromomycin, rhodostreptomycin, streptomycin, tobramycin, apramycin, etc.), polymyxins (e.g., polymyxin B, colistin), fluoroquinolones (norfloxacin, ciprofloxacin, levofloxacin (Levaquin®), moxifloxacin (Avelox®), or enoxacin), penicillins (e.g., amoxicillin, ampicillin, etc.), and lincosamides (e.g., clindamycin, lincomycin, etc.).

In another embodiment the additional anti-bacterial agent is selected from metronidazole, glycopeptides (e.g., vancomycin, dalbavancin, telavancin, oritivancin), oxazolidinones (e.g., linezolid), lipeopetides (e.g., daptomycin), and tetracyclines including gylcylcyclines (e.g., tigecycline).

Other non-limiting examples of additional antibacterial agents can be found in Walsh and Wright, *Chemical Reviews* 105(2):391-394 (2005); and Bush et al., *Current Opinion in Microbiology* 7:466-476 (2004).

In one embodiment, the additional antibacterial agent is used in combination with compounds or pharmaceutically acceptable salts of the invention to lower the frequency of resistance. Examples include cefepime, cefpirome, imipenem, meropenem, ertapenem, doripenem, sulopenem, ceftazidime, piperacillin/tazobactam, ciprofloxacin, levofloxacin, moxifloxacin, polymyxin B, and tigecycline.

In another embodiment, the additional antibacterial agent may be a standard anti-anaerobe drug used in combination with compounds or pharmaceutically acceptable salts of the invention to treat intra-abdominal infections. Examples include clindamycin, metronidazole, imipenem, meropenem, doripenem, ertapenem, cefotetan, cefepime, cefpirome, and third generation cephalosporins.

In another embodiment, the additional antibacterial agent may be an acceptable anti-Gram positive agent used in combination with compounds or pharmaceutically acceptable salts of the invention for empiric therapy to treat *P. aeruginosa* and all *Enterobateriaceae*. Examples include vancomycin, linezolid, daptomycin, dalbavancin, telavancin, and oritivancin.

In one embodiment, the one or more additional active agents, when used, are administered prior to administration of a compound of formula (I). In another embodiment, the one or more additional active agents, when used, are administered after administration of a compound of formula (I). In another embodiment, the one or more additional active agents, when used, are administered at about the same time as administration of a compound of formula (I).

The additional active agent may be administered by any route useful to administer said additional active agent.

In one embodiment, the one or more additional active agents are present in the pharmaceutical composition of the invention. Accordingly, in another embodiment, the invention relates to a method of treating a patient with a pharmaceutical composition of the invention further comprising one or more additional active agents.

It is to be understood that any section headings and subheadings herein are for the convenience of the reader and are non-limiting. For example, the subject matter in the Summary of the Invention has no special status solely as a result of its placement in that section.

Unless otherwise indicated, the language and terms used in this document are to be given their broadest reasonable interpretation as understood by the relevant skilled artisan. In addition, in descriptions and claims in which the subject matter (e.g., substitution at a given molecular position) is recited as being selected from a group of possibilities, the recitation is specifically intended to include any subset of the recited group. In the case of multiple variable positions or substituents, any combination of group or variable subsets is also contemplated.

Unless otherwise stated, the following abbreviations have the following meaning: "L" means "liter", "mL" means "milliliter", "mol" means "moles", "mmol" means "millimoles", "Ac" means "acetyl", "Ph" means "phenyl", "Bz" means "benzoyl", "DCM" or "$CH_2Cl_2$" means "dichloromethane", "DMSO" means "dimethylsulfoxide", "MIC" means "minimum inhibitory concentration", "MS" means "Mass Spectrometry" (all samples herein were analyzed either by LCMS-electrospray (gradient elution using acetonitrile, water, formic acid mixtures) or probe APCl methods), "LCMS" means "liquid chromatography mass spectrometry", "NMR" means "nuclear magnetic resonance spectroscopy" (All samples herein were run at 400 MHz on Varian instruments, unless otherwise indicated), "THF" means "tetrahydrofuran", "spp." means "species" and "cfu" means "colony-forming unit".

As used herein, the term "$(C_1-C_6)$alkyl" refers to linear or branched hydrocarbons (e.g., methyl, ethyl, n-propyl, isopropyl) of 1 to 6 carbon atoms in length.

Unless otherwise indicated, the term "heterocycloalkyl", as used herein, refer to non-aromatic cyclic groups containing one or more heteroatoms, preferably from one to four heteroatoms, each preferably selected from oxygen, sulfur and nitrogen. The heterocycloalkyl groups of this invention can also include ring systems substituted with one or more oxo moieties. Examples of non-aromatic heterocycloalkyl groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, and 1,4-diox-aspiro[4.2]heptyl.

Unless otherwise indicated, the term "heteroaryl", as used herein, refers to an aromatic ring containing one or more heteroatoms (preferably oxygen, sulfur and nitrogen), preferably from one to four heteroatoms. Examples of 5 to 6 membered heteroaryls are pyridinyl, pyridazinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, triazinyl, purinyl, oxadiazolyl, thiadiazolyl, furazanyl.

The term "heterocycle" includes heteroaryl and heterocycloalkyl rings as well as non-aromatic heterocyclic rings containing zero or more double bonds.

Unless otherwise apparent or indicated, the compounds of the invention and term "compound" in the claims embraces any pharmaceutically acceptable salts or solvates, and any amorphous or crystal forms, or tautomers, whether or not specifically recited in context. Similarly, a recitation is open to any material or composition containing the recited compound (e.g., a composition containing a salt of a racemic mixture of compounds, tautomers, epimers, stereoisomers, impure mixtures, etc.).

The compounds of formula (I) may exist in unsolvated and solvated forms. Thus, it will be understood that the compounds of the invention also include hydrate and solvate forms as discussed below.

The term "solvent" as it relates to the compositions of the invention includes organic solvents (e.g., methanol, ethanol, isopropanol, ethyl acetate, methylene chloride, and tetrahydrofuran) and water. The one or more solvents may be present in a non-stoichiometric amount, e.g., as a trace impurity, or in sufficient excess to dissolve the compound of the invention. Alternatively, the one or more solvents may be present in a stoichiometric amount, e.g., 0.5:1, 1:1, or 2:1 molar ratio, based on the amount of compound of the invention.

The term "solvate" is used herein to describe a noncovalent or easily reversible combination between solvent and solute, or dispersion means and disperse phase. It will be understood that the solvate can be in the form of a solid, slurry (e.g., a suspension or dispersion), or solution. Non-limiting examples of solvents include ethanol, methanol, propanol, acetonitrile, dimethyl ether, diethyl ether, tetrahydrofuran, methylene chloride, and water. The term 'hydrate' is employed when said solvent is water.

A currently accepted classification system for organic hydrates is one that defines isolated site, or channel hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Unless otherwise indicated, the term "pharmaceutically acceptable salt(s)", as used herein, unless otherwise indicated, includes salts of acidic or basic groups which can be present in the compounds. Compounds that are basic in nature are capable of forming a wide variety of salts with various inorganic and organic acids. The acids that can be used to prepare pharmaceutically acceptable acid addition salts of such basic compounds are those that form non-toxic acid addition salts. The compounds can form, e.g., sulfates, phosphates, citrates, acetates, tosylates, succinates, besylates, mesylates, lactates, and hydrochlorides. Basic salts can be mono or dibasic. In one preferred embodiment, the salt is a fumarate.

Unless otherwise indicated, the terms "treat," "treatment," and "treating", as used herein in the context of using the compounds of the present invention, unless otherwise indicated, means reversing, alleviating, inhibiting the progress of one or more symptoms of such disorder or condition.

As used herein the term "patient" refers to a mammal such as, e.g., a human, dog, cat, horse, pig, cow, and the like. In one embodiment, the patient is a human.

Unless otherwise indicated, the term "pharmaceutical composition" refers to an active compound in any form suitable for effective administration to a subject, e.g., a mixture of the compound and at least one pharmaceutically acceptable carrier.

Unless otherwise indicated, the term "pharmaceutically acceptable carrier" refers to a material that can be administered to a subject together with a compound in a pharmaceutical composition. The carrier should not destroy the pharmacological activity of the compound and should be non-toxic when administered in doses sufficient to deliver a therapeutic amount of the compound.

The term "excipient" means an inert material that is combined with the compounds of formula (I) to produce a pharmaceutical composition or oral drug dosage form. The term "pharmaceutically acceptable excipient" means that the excipient must be compatible with other ingredients of the composition, and not deleterious to the recipient thereof. The pharmaceutically acceptable excipients are chosen on the basis of the intended dosage form.

Compounds of the present invention have asymmetric centers and therefore can exist in different enantiomeric and diastereomeric forms. The invention includes all optical isomers and stereoisomers, and mixtures thereof in all ratios, and to all pharmaceutical compositions and methods of treatment that can employ or contain them. Although specific compounds exemplified in this application can be depicted in a particular stereochemical configuration, compounds having either the opposite stereochemistry at any chiral centers or mixtures thereof are also envisioned. The foregoing can be present as mixtures or enriched in any component to any degree. Where stereochemistry at a position is not specified, such is intended to encompass either configuration or a mixture of any ratio.

Compounds of this invention include pharmaceutically acceptable derivatives or prodrugs thereof. A "pharmaceutically acceptable derivative or prodrug" means any pharmaceutically acceptable salt, ester, salt of an ester or other derivative of a compound that, upon administration to a recipient, is capable of providing (directly or indirectly) a compound of this invention or a metabolite or residue thereof. Particularly favored derivatives and prodrugs of the invention are those that increase the bioavailability of the compounds when such compounds are administered to a patient (e.g., by allowing an orally administered compound to be more effectively absorbed into the blood), enhance delivery of the parent compound to a given biological compartment, increase solubility to allow administration by injection, alter metabolism or alter rate of excretion.

The compounds of formula (I) may exhibit polymorphism. Polymorphic compounds of formula (I) may be prepared by crystallization of a compound of the present invention under various conditions. For example, there may be employed various solvents (including water) or different solvent mixtures for recrystallization; crystallization at different temperatures; various modes of cooling ranging from very fast to very slow cooling during crystallization. Polymorphs may also be obtained by heating or melting a compound of the present invention followed by gradual or fast cooling. The presence of polymorphs may be determined by solid probe NMR spectroscopy, IR spectroscopy, differential scanning calorimetry, powder X-ray diffraction or other such techniques.

The present invention includes compounds wherein one or more hydrogen, carbon or other atoms are replaced by different isotopes thereof. Such compounds can be useful as research and diagnostic tools in metabolism pharmacokinetic studies and in binding assays. These isotopically-labeled compounds are identical to those compounds of formula (I), but for the fact that one or more atoms are replaced by an atom having an atomic mass or mass number different from the atomic mass or mass number predominantly found in nature. Examples of isotopes that can be incorporated into compounds of the invention include isotopes of hydrogen, carbon, nitrogen, oxygen, and sulfur, such as, but not limited to, $^2H$, $^3H$, $^{13}C$, $^{14}C$, $^{15}N$, $^{18}O$, $^{17}O$, and $^{35}S$, respectively. The compounds of formula (I) of the invention containing the aforementioned isotopes and/or other isotopes of these atoms are within the scope of this invention. Certain isotopically-labeled compounds of formula (I), for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labeled compounds of the invention can generally be prepared by carrying out the procedures disclosed in the Schemes and/or in the Examples and described below, by substituting a readily available isotopically-labeled reagent for a non-isotopically-labeled reagent.

The term "protecting group" refers to a suitable chemical group that can be attached to a functional group and removed at a later stage to reveal the intact functional group. Examples of suitable protecting groups for various functional groups are described in T. W. Greene and P. G. M. Wuts, Protective Groups in Organic Synthesis, 2nd Ed., John Wiley and Sons (1991 and later editions); L. Fieser and M. Fieser, Fieser and Fieser's Reagents for Organic Synthesis, John Wiley and Sons (1994); and L. Paquette, ed. Encyclopedia of Reagents for Organic Synthesis, John Wiley and Sons (1995). The term "hydroxy protecting group", as used herein, unless otherwise indicated, includes Ac, Bz, and various hydroxy protecting groups familiar to those skilled in the art, including the groups referred to in Greene.

The examples and preparations provided below further illustrate and exemplify the compounds of the present invention and methods of preparing such compounds. It is to be understood that the scope of the present invention is not limited in any way by the scope of the following examples and preparations.

All patents, patent applications, publications, test methods, literature, and other materials cited above and below herein are hereby incorporated herein by reference in their entireties.

DETAILED DESCRIPTION OF THE INVENTION

As noted above, in one embodiment, the present invention relates to compounds of formula (I) and pharmaceutically acceptable salts thereof, as described above. The compounds of formula (I) are depicted structurally in the Summary of the Invention an elsewhere herein for the convenience of the reader.

General Preparation Methods

The compounds of the present invention may be prepared according to the descriptions, schemes, and examples herein, which are non-limiting, in combination with the knowledge of the skilled artisan.

Scheme A

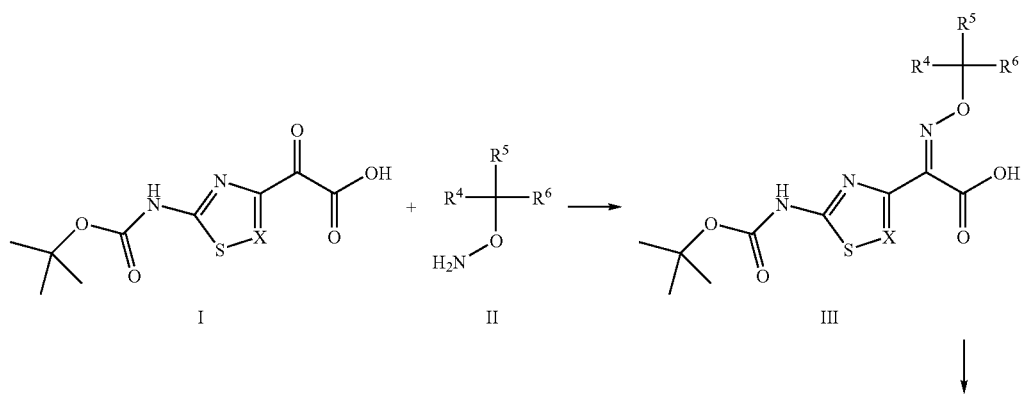

-continued

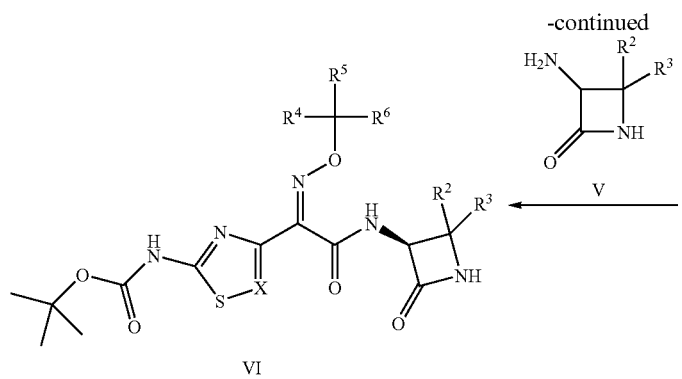

VI

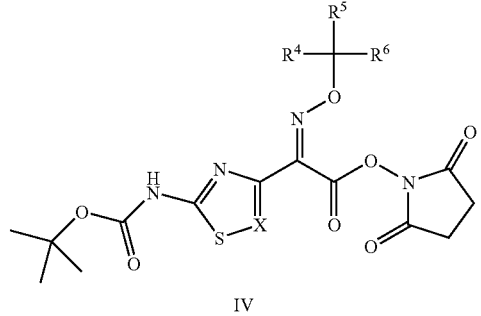

V

→

IV

The compounds of the present invention can be prepared as outlined in schemes A through C. Compounds of the general formula I (Scheme A), prepared as described in Yamawaki, K., et al., Bioorganic & Medicinal Chem., (2007), 15, 6716 and Yamamoto, H., et al., Bioorganic and Medicinal Chem., (2002), 10, 1535, can be reacted with hydroxylamines of the general formula II (prepared as described in WO 2007/065288, published Jun. 14, 2007) in a solvent such as methanol at ambient temperature for approximately 2 hours to form carboxylic acids of the formula III. Activated esters of the formula IV can be prepared by reaction of compounds of the formula III with N-hydroxysuccinamide in the presence of coupling reagent such as dicyclohexylcarbodiimide or diisopropylcarbodiimide in a solvent such as dichloromethane at ambient temperature. A compound of formula V, prepared as described by Waulte, S. R. et al. J. Org. Chem. (1986), 51, 3133; Paloma, C., et al., J. Org. Chem. (1997), 62, 2070; Lall, M. S., et al., J. Org. Chem. (2002), 67, 1536 and Chhabra, S. R., et al., J. Org. Chem. (2002), 67, 4017, can be generated by deprotection of the corresponding N-benzyloxycarbonyl (Cbz) protected compound by hydrogenolysis at ambient temperature in the presence of palladium on carbon, under approximately two to four atmospheres of hydrogen gas, in a solvent such as methanol, ethanol, tetrahydrofuran, toluene or acetic acid sometimes requiring a binary combination thereof. If the hydrogenation is done in the presence of acetic acid, the intermediate aminoazetidinone can be isolated as the acetate salt and subsequently reacted with compounds of the formula IV in solvents such as methanol, ethanol or acetonitrile in the presence of a base such as triethylamine to form amides of the general formula VI. When acetic acid is not used in the hydrogenation, the aminoazetidinones produced, once the catalyst is removed by filtration, can be reacted in situ with compounds of the formula IV to generate amides of the formula VI.

Scheme B

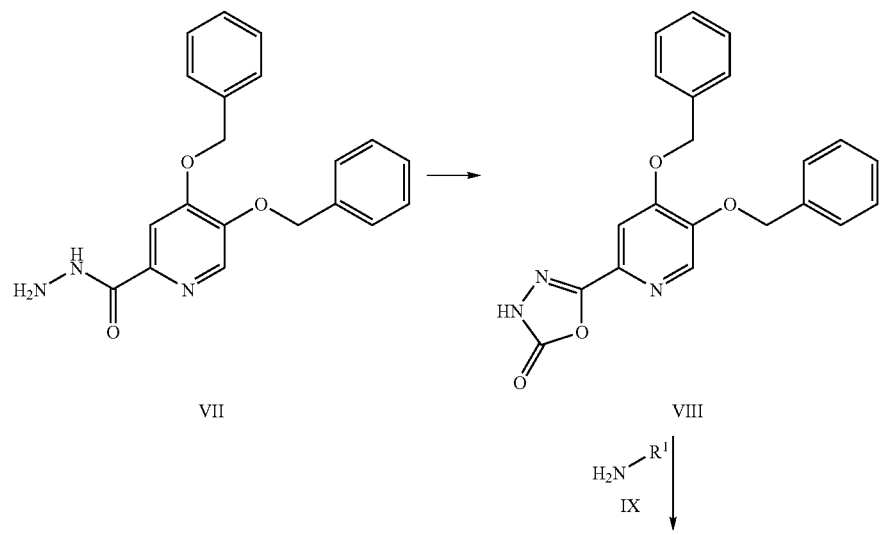

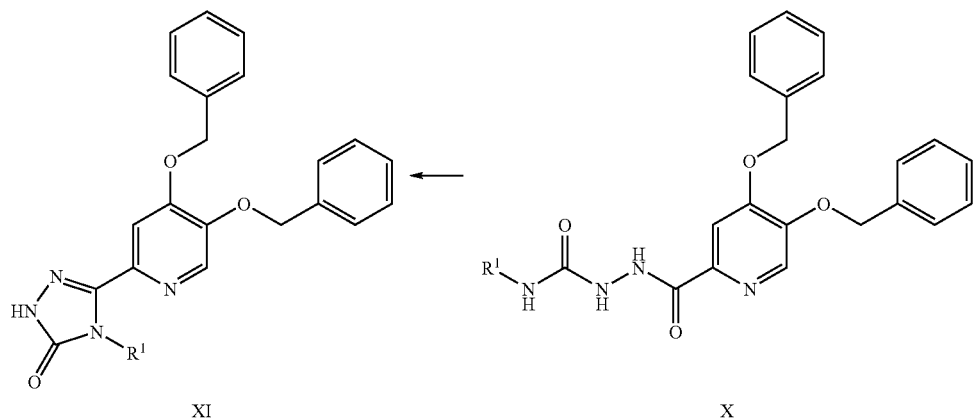

XI                                                                 X

Triazolones of the formula XI can be prepared as outlined in Scheme B. Starting from commercially available Kojic acid (CAS number: 501-30-4), compound VII can be prepared in five steps as described in EP 0281289, published Feb. 19, 1988. Reaction of VII with phosgene or a phosgene equivalent such as carbonyldiimidazole in a solvent such as dichloromethane or tetrahydrofuran at ambient temperature produces compound VIII. Reaction of compound VIII with a primary amine of formula IX in a solvent such as tetrahydrofuran at elevated temperature such as between 40° C. and 60° C. will produce compounds of the general formula X. Compounds of the formula X can be cyclized to form compounds of the formula XI by reaction in water at reflux in the presence of a base such as sodium hydroxide or potassium hydroxide. Alternatively, in some cases, a similar cyclization reaction can be accomplished by reaction of compounds of the formula X in N-trimethylsilyl-N-methyltrifluoroacetamide (MSTFA) at approximately 150° C. resulting from microwave irradiation.

Scheme C

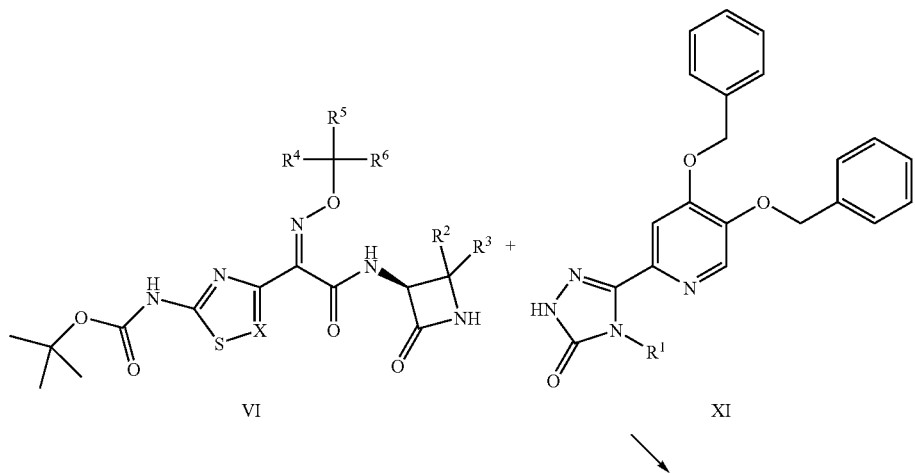

-continued

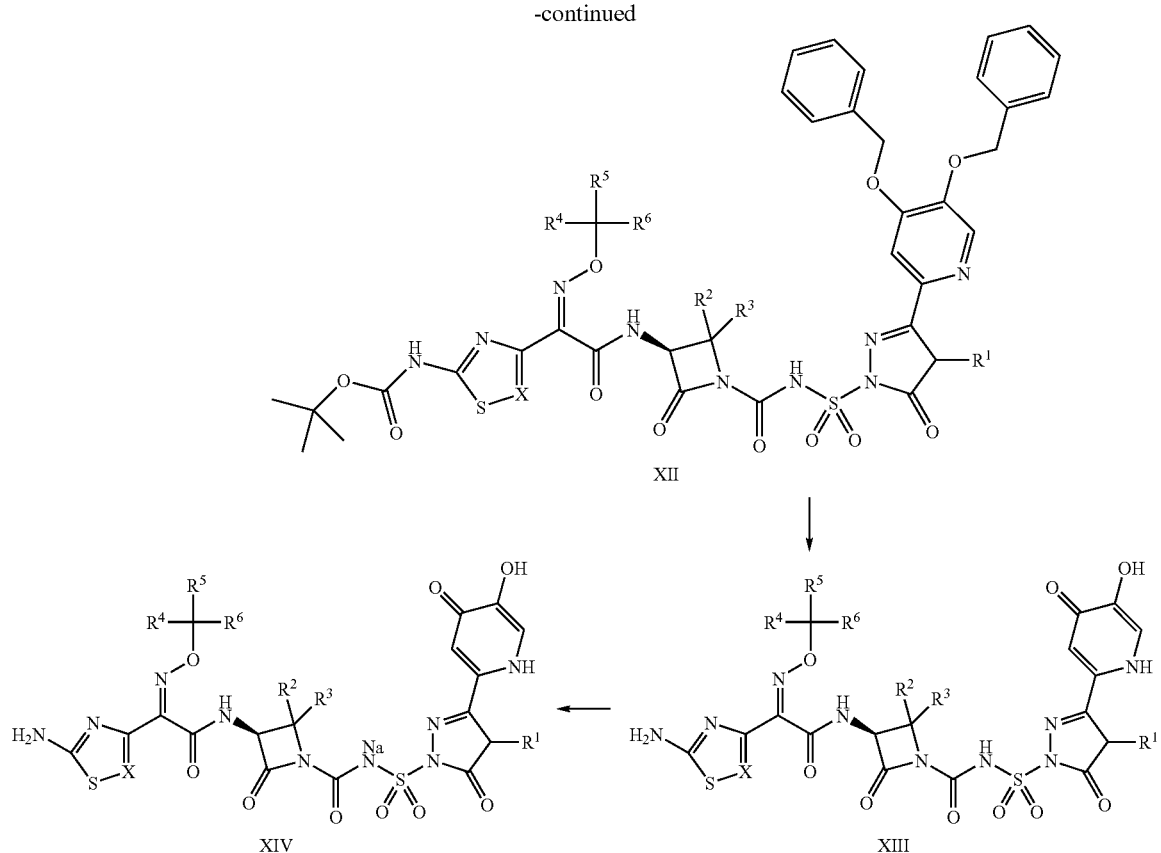

The coupling of compounds VI and XI and the final construction of the compounds of the present invention can be accomplished as outlined in Scheme C. The coupling of VI and XI to generate compounds of the general formula XII can be accomplished by first reacting compounds of the formula XI with excess MSTFA in tetrahydrofuran at approximately 40° C. for one to two hours followed by removal of the tetrahydrofuran, excess MSTFA and byproducts under vacuum. Separately, compounds of the formula VI can be reacted with chlorosulfonylisocyanate (CSI) in dichloromethane at 0° C. for approximately 45 minutes. The adduct of the compound of formula XI can then be re-dissolved in tetrahydrofuran and to this mixture added the adduct from reaction of the compound of formula VI with CSI. Stirring of these two components at 0° C. for approximately two hours followed by stirring at ambient temperature for up to 18 hours produces the compounds of the general formula XII. Alternatively, this coupling reaction can be accomplished as follows: the CSI adduct prepared as described above is mixed with the compound of formula XI, which can be silylated by reaction with excess hexamethyldisilizide (HMDS) in the presence of a catalytic amount of trimethylsilylchloride (TMS-Cl) at approximately 140° C. After cooling to ambient temperature, this material can be dissolved in a solvent such as dichloromethane and mixed the CSI adduct generating the compound of formula XII. Removal of the benzyl protecting groups from compounds of the formula XII can be accomplished by reaction with between two and four atmospheres of hydrogen gas in a binary solvent system consisting of tetrahydrofuran and acetic acid at ambient temperature and in the presence of a palladium catalyst such as palladium black. Following removal of the catalyst and solvent, treatment of the crude material with an acid such as trifluoroacetic acid in a solvent such as dichloromethane at ambient temperature removes the tertiary-butyloxycarbonyl protecting group and the tertiary-butylester if contained within $R^6$. The crude material of the present invention (XIII) can then be purified by reverse-phase chromatography using a C18 resin with a gradient mobile phase consisting of acetonitrile and water, buffered with formic acid. The sodium salts with the general formula XIV can then be generated from the compounds of formula XIII by treatment with sodium bicarbonate in water followed by lyophilization. If a second acidic site is present within $R^6$ such as a carboxylic acid, the bis-sodium salts of the formula XIV can be produced following the same procedure, but adding a second equivalent of sodium bicarbonate prior to lyophilization.

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLES

The Examples below were generally carried out under inert atmosphere (nitrogen or argon), particularly in cases where oxygen or moisture-sensitive reagents or intermediates were employed. Commercial solvents and reagents were generally used without further purification. All products were dried before characterization or use in subsequent chemistry. Chemical shifts for nuclear magnetic resonance (NMR) data

Example 1

Preparation of 2-({[(1E)-1-(2-amino-1,3-thiazol-4-yl)-2-{[(3S)-1-({[4-ethyl-3-(5-hydroxy-4-oxo-1,4-dihydropyridin-2-yl)-5-oxo-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid (1)

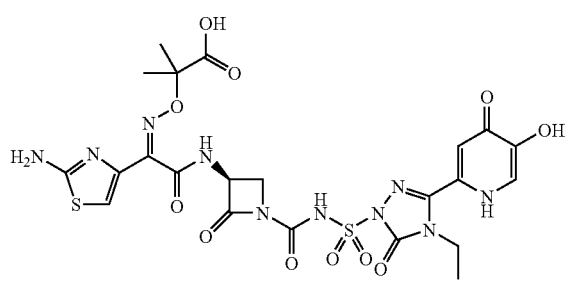

Compound 1 was prepared by the procedures depicted in schemes 1 to 6 and outlined in detail below.

Step 1. Preparation of benzyl 4,5-bis(benzyloxy)pyridine-2-carboxylate (C4)

A. Preparation of 5-(benzyloxy)-2-(hydroxymethyl)-4H-pyran-4-one (C1). 5-Hydroxy-2-(hydroxymethyl)-4H-pyran-4-one (300 g, 2.11 mol) was dissolved in methanol (9 L) and treated with potassium carbonate (439 g, 3.18 mol), followed by slow addition of benzyl chloride (433 g, 3.42 mol). The reaction mixture was stirred at 65° C. for 8 hours. After cooling to room temperature, it was stirred for an additional 16 hours, then concentrated in vacuo to a thick paste. This residue was cooled to 10° C. and diluted with ice water, resulting in a precipitate that was gathered by filtration to provide C1 as a solid. Yield: 325 g; 1.40 mol, 66%. $^1$H NMR (400 MHz, DMSO-$d_6$) δ 4.29 (s, 2H), 4.94 (s, 2H), 6.32 (s, 1H), 7.33-7.42 (m, 5H), 8.17 (s, 1H).

B. Preparation of 5-(benzyloxy)-4-oxo-4H-pyran-2-carboxylic acid (C2). A solution of chromium(VI) oxide (64.6 g, 0.646 mol) in water (90 mL) was cooled to −5° C. and treated drop-wise with concentrated sulfuric acid (56 mL). This was diluted with additional water (40 mL), and then added drop-wise to a cold (−5° C.) solution of C1 (100 g, 0.43 mol) in acetone (4.5 L). The reaction mixture was stirred at 20° C. for 3 hours, then filtered through a pad of Celite®. Concentration of the filtrate provided a residue, which was washed with hexane to provide C2. Yield: 80 g, 0.325 mol, 76%. $^1$H NMR (400 MHz, DMSO-$d_6$) δ 4.97 (s, 2H), 6.93 (s, 1H), 7.34-7.42 (m, 5H), 8.37 (s, 1H).

Scheme 1

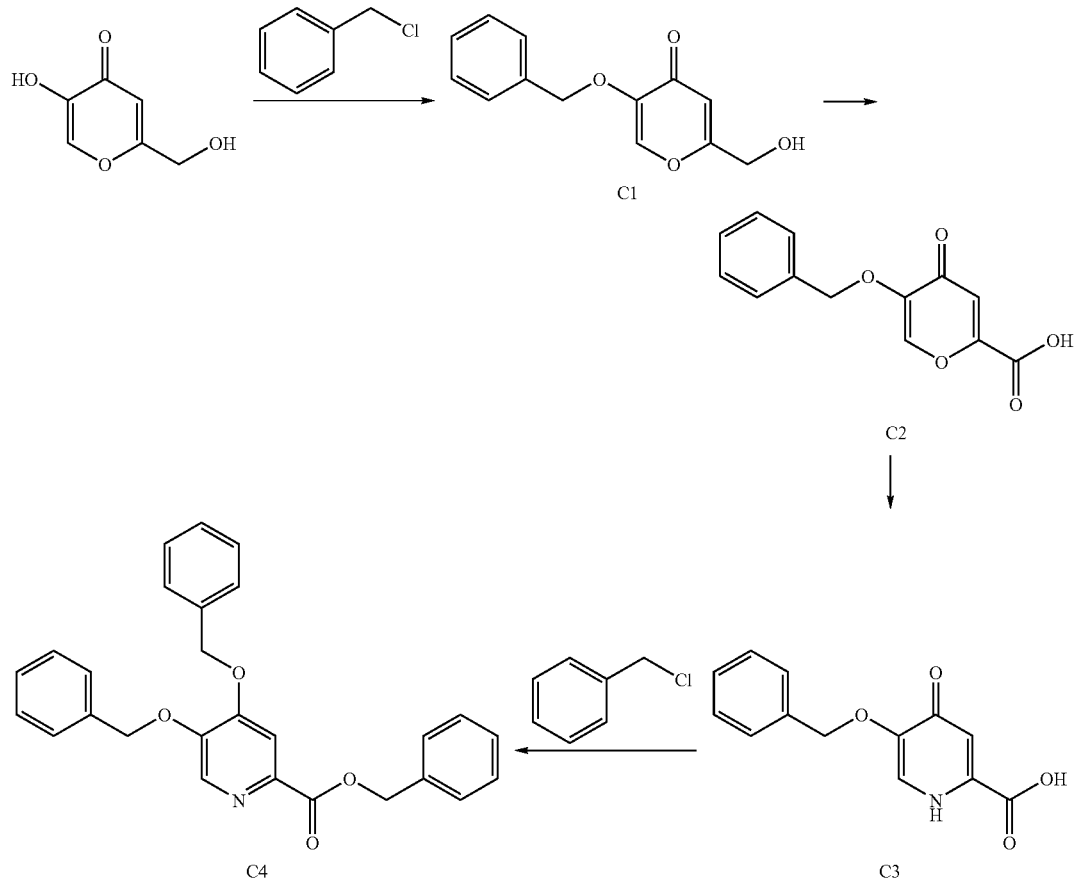

C. Preparation of 5-(benzyloxy)-4-oxo-1,4-dihydropyridine-2-carboxylic acid (C3). A mixture of C2 (100 g, 0.406 mol) and aqueous ammonium hydroxide solution (25%, 1 L) was stirred in an autoclave for 1 hour, and then heated at 83° C. for 7 hours at atmospheric pressure. After cooling slowly over about 18 hours, the reaction mixture was acidified to pH 3 with concentrated hydrochloric acid. The resulting precipitate was collected by filtration, washed with water, and dissolved in saturated aqueous sodium bicarbonate solution. The solution was washed with dichloromethane, then acidified with concentrated hydrochloride acid. The resulting solid was collected by filtration, washed with water and dried at 50° C. to provide C3. Yield: 85 g, 0.347 mol, 85%. $^1$H NMR (400 MHz, DMSO-$d_6$) δ 5.17 (s, 2H), 7.17 (br s, 1H), 7.33-7.49 (m, 7H).

D. Preparation of C4. Benzyl chloride (105.6 mL, 0.918 mol) was added to a solution of C3 (90 g, 0.367 mol) in dimethylformamide (1.25 L). Potassium carbonate (124.8 g, 0.903 mol) was added, and the mixture was stirred at 80° C. for 16 hours. After cooling to room temperature, the reaction was treated with ice water, and the resulting solid was collected by filtration and purified by silica gel chromatography to afford C4: Yield: 50 g, 0.118 mol, 32%. MS m/z 426 (M+1). $^1$H NMR (400 MHz, DMSO-$d_6$) δ 5.32 (s, 6H), 7.33-7.46 (m, 15H), 7.76 (s, 1H), 8.37 (s, 1H).

Scheme 2

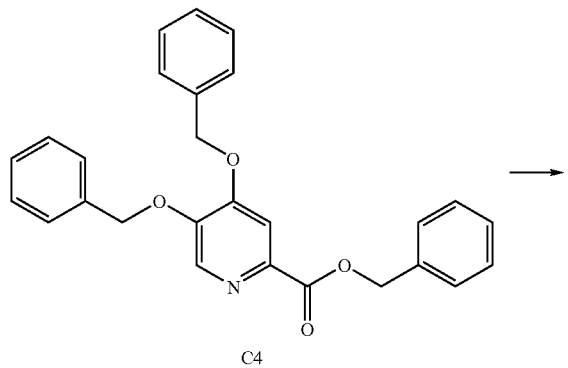

C4

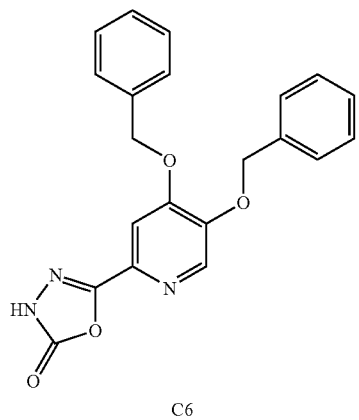

C6

Step 2. Preparation of 5-(4,5-bis(benzyloxy)pyridin-2-yl)-1,3,4-oxadiazol-2(3H)-one (C6)

A. Preparation of 4,5-bis(benzyloxy)pyridine-2-carbohydrazide (C5). Hydrazine monohydrate (47.5 mL, 978 mmol) was added drop-wise over 10 minutes to a suspension of C4 (20 g, 47.0 mmol) in methanol (100 mL). The resulting mixture was heated to 65° C. for 2 hours, then cooled to room temperature and filtered under vacuum. The collected solids were washed with methanol to provide C5 as a white solid. Yield: 15.4 g, 44.1 mmol, 94%. LCMS m/z 350.1 (M+1). $^1$H NMR (400 MHz, DMSO-$d_6$) δ 4.47 (d, J=4.6 Hz, 2H), 5.30 (s, 2H), 5.32 (s, 2H), 7.31-7.48 (m, 10H), 7.67 (s, 1H), 8.23 (s, 1H), 9.65 (t, J=4.5 Hz, 1H).

B. Preparation of 5-[4,5-bis(benzyloxy)pyridin-2-yl]-1,3,4-oxadiazol-2(3H)-one (C6). Carbonyl diimidazole (97%, 2.87 g, 17.2 mmol) was added to a suspension of C5 (5.00 g, 14.3 mmol) in tetrahydrofuran (75 mL). The reaction mixture was stirred at room temperature for 3 hours, during which time the white suspension became a homogeneous solution, and then a white suspension. The solid was collected by filtration and washed with tetrahydrofuran (3×5 mL) to provide C6 as a white solid. Yield: 4.92 g, 13.1 mmol, 92%. LCMS m/z 376.1 (M+1). $^1$H NMR (400 MHz, DMSO-$d_6$) δ 5.31 (s, 2H), 5.33 (s, 2H), 7.32-7.48 (m, 10H), 7.56 (s, 1H), 8.38 (s, 1H), 12.64 (br s, 1H).

Scheme 3

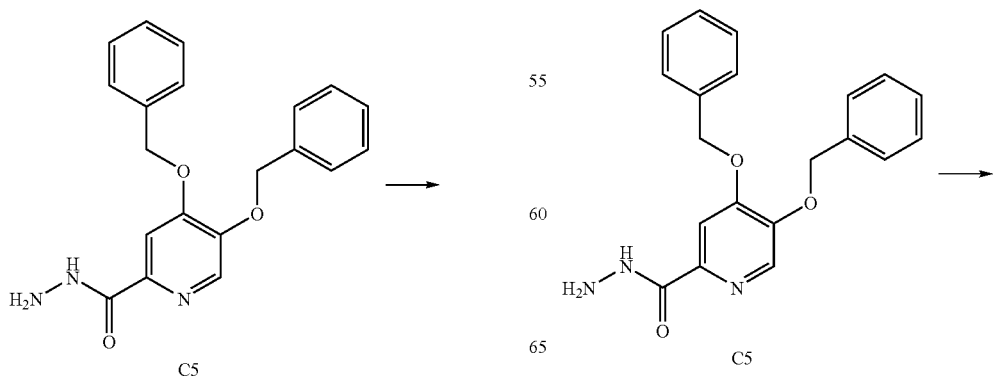

C5        C5

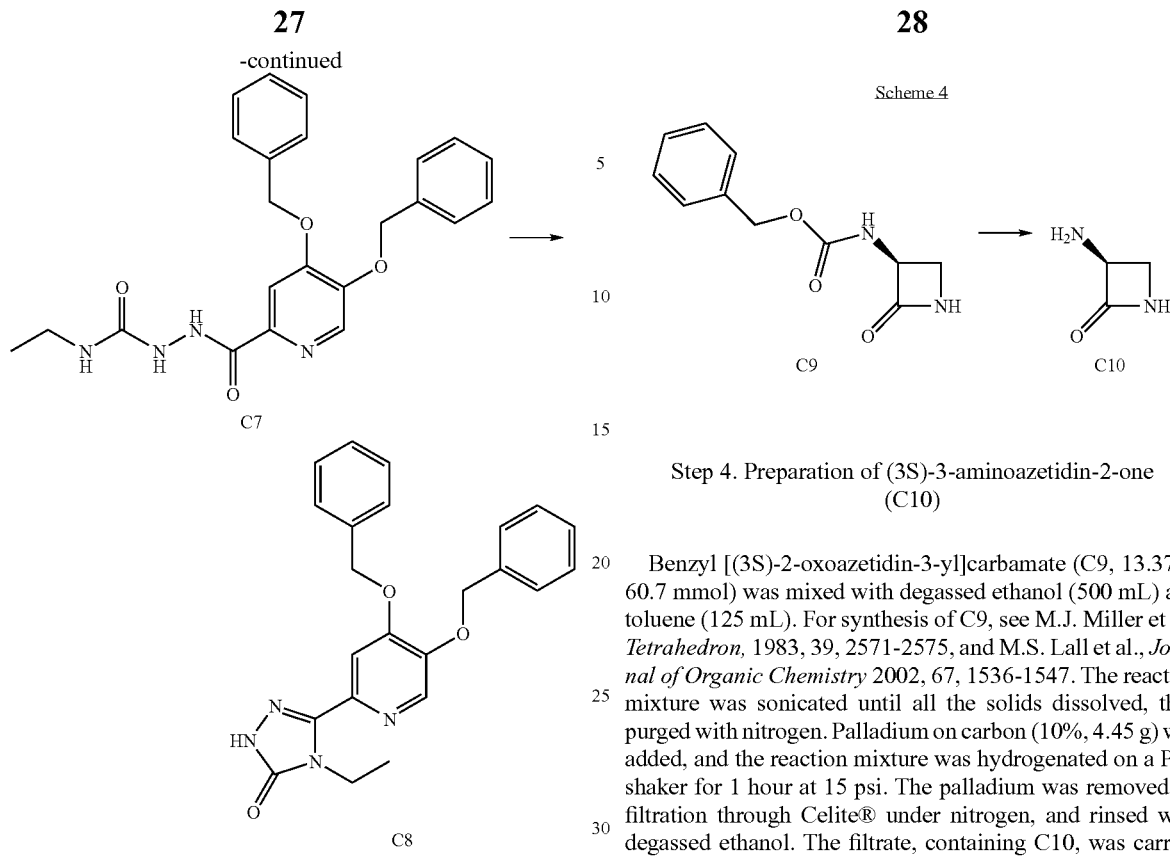

Step 3. Preparation of 5-(4,5-bis(benzyloxy)pyridin-2-yl)-4-ethyl-2H-1,2,4-triazol-3(4H)-one (C8)

A. Preparation of 1-(3,4-bis(benzyloxy)picolinoyl)-4-ethylsemicarbazide (C7). To a solution of C5 (0.75 g/0.215 mol) in 5 mL N,N-dimethylformamide at 5° C. was added slowly a solution of 229 mg (3.22 mmol) of ethylisocyanate in 5 mL of tetrahydrofuran and the resulting mixture stirred at room temperature for 2 hours, at which point, the reaction mixture was transferred to a solution containing 0.161 g (0.0032 mol) hydrazine monohydrate in 10 mL of tetrahydrofuran at a rate such to maintain a temperature less than 15° C. Once added, the resulting mixture stirred at room temperature for 1 hour, at which point the mixture was poured into 50 mL of ice-water forming a precipitate, which was collected by filtration and dried in vacuo affording C7 as a white solid. LCMS m/z 421 (M+1). $^1$H NMR (400 MHz, CDCL3-$d_6$) δ 1.25 (t, J=6.2 Hz, 3H), 4.25 (br. d, 2H), 5.24 (br. s, 4H), 7.31-7.46 (m, 10H), 7.55 (br. s, 1H), 8.18 (s, 1H).

B. Preparation of 5-(4,5-bis(benzyloxy)pyridin-2-yl)-4-ethyl-2H-1,2,4-triazol-3(4H)-one (C8) (Cyclization Method 1). To a stirred solution of 0.42 g (0.999 mmol) of C7 was added 8 equivalents (0.448 g/7.99 mmol) of potassium hydroxide dissolved in 2 mL of water and the resulting mixture heated to reflux for 24 hours at which point the reaction mixture was concentrated to dryness in vacuo. The crude product was then purified by column chromatography (silicagel, 3 to 5% methanol in ethylacetate producing 0.683 g (46%) of compound C8. LCMS m/z 403.3 (M+1). $^1$H NMR (400 MHz, CDCL3-$d_6$) δ 1.26 (t, J=7.3 Hz, 3H), 4.26 (q, J=6.6 Hz, 2H), 5.24 (s, 4H), 7.29-7.47 (m, 10H), 7.57 (s, 1H), 8.16 (s, 1H), 9.86 (br. s, 1H).

Step 4. Preparation of (3S)-3-aminoazetidin-2-one (C10)

Benzyl [(3S)-2-oxoazetidin-3-yl]carbamate (C9, 13.37 g, 60.7 mmol) was mixed with degassed ethanol (500 mL) and toluene (125 mL). For synthesis of C9, see M.J. Miller et al., *Tetrahedron*, 1983, 39, 2571-2575, and M.S. Lall et al., *Journal of Organic Chemistry* 2002, 67, 1536-1547. The reaction mixture was sonicated until all the solids dissolved, then purged with nitrogen. Palladium on carbon (10%, 4.45 g) was added, and the reaction mixture was hydrogenated on a Parr shaker for 1 hour at 15 psi. The palladium was removed by filtration through Celite® under nitrogen, and rinsed with degassed ethanol. The filtrate, containing C10, was carried directly into the coupling reaction with C12, Step 4B. Yield: assumed quantitative. Material from a similar experiment was concentrated to dryness to obtain NMR data: $^1$H NMR (400 MHz, DMSO-$d_6$) δ 2.12 (br s, 2H), 2.78 (dd, J=5.1, 2.3 Hz, 1H), 3.31 (dd, J=5.3, 5.3 Hz, 1H), 3.97 (m, 1H), 7.69 (br s, 1H).

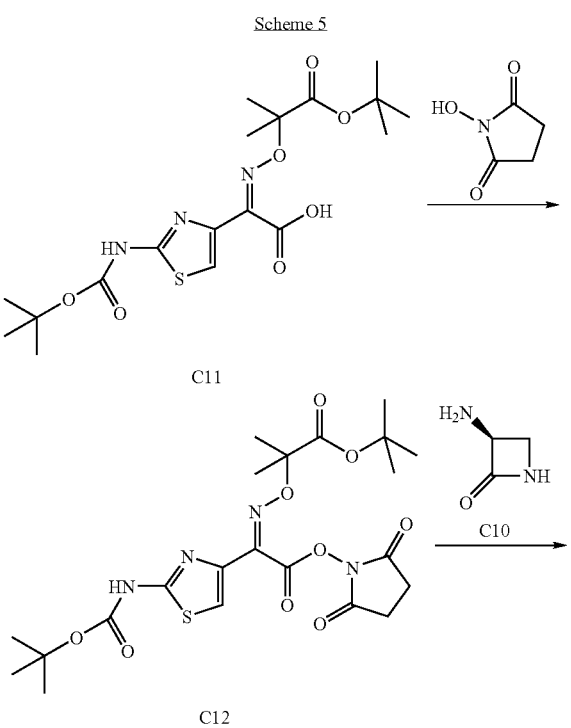

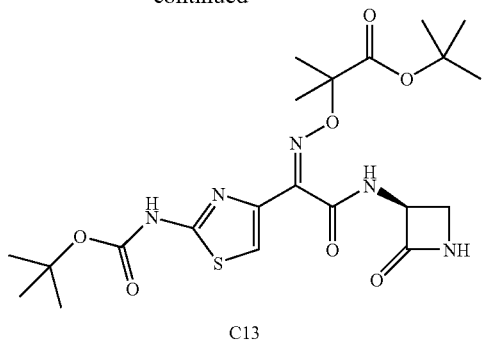

C13

Step 5. Preparation of tert-butyl 2-({[(1Z)-1-{2-[(tert-butoxycarbonyl)amino]-1,3-thiazol-4-yl}-2-oxo-2-{[(3S)-2-oxoazetidin-3-yl]amino}ethylidene]amino}oxy)-2-methylpropanoate (C13)

A. Preparation of tert-butyl 2-[({(1Z)-1-{2-[(tert-butoxycarbonyl)amino]-1,3-thiazol-4-yl}-2-[(2,5-dioxopyrrolidin-1-yl)oxy]-2-oxoethylidene}amino)oxy]-2-methylpropanoate (C12). 1-Hydroxypyrrolidine-2,5-dione (N-hydroxysuccinimide, 8.84 g, 76.8 mmol) was added to a suspension of (2Z)-{2-[(tert-butoxycarbonyl)amino]-1,3-thiazol-4-yl}[(2-tert-butoxy-1,1-dimethyl-2-oxoethoxy)imino]acetic acid (C11, 30 g, 70 mmol) in dichloromethane (400 mL). For synthesis of C11, see K. Yamawaki et al., *Bioorganic and Medicinal Chemistry* 2007, 15, 6716-6732. The mixture was cooled to 0° C., N,N'-dicyclohexylcarbodiimide (97%, 15.6 g, 73.3 mmol) was added, and the reaction was stirred at 0° C. for 30 minutes and then at room temperature for 3 hours. The mixture was filtered through Celite® and concentrated in vacuo to afford C12 as a white solid. Yield: 36.17 g, 68.7 mmol, 98%. LCMS m/z 527.2 (M+1). $^1$H NMR (400 MHz, CDCl$_3$) δ 1.43 (s, 9H), 1.54 (s, 9H), 1.61 (s, 6H), 2.91 (br s, 4H), 7.50 (s, 1H), 8.31 (br s, 1H).

B. Preparation of C13. A solution of C10 (5.23 g, 60.7 mmol) in ethanol/toluene (900 mL, solution obtained in Step 4) was treated with compound C12 (26.6 g, 50.6 mmol), and the reaction mixture was slowly concentrated under reduced pressure, over the course of an hour, to one-third of its original volume. The resulting suspension was stirred at 35° C. under nitrogen for about 18 hours. Removal of solvent in vacuo afforded a crude product, which was dried under vacuum for 30 minutes. The resulting solids were partitioned between 1:1 ethyl acetate/tetrahydrofuran (1 L) and aqueous sodium bicarbonate solution (500 mL). Additional water was required to dissolve solids observed during the separation. The aqueous layer was extracted with 1:1 ethyl acetate/tetrahydrofuran (2×300 mL), and the combined organic layers were filtered and concentrated in vacuo. The crude solid was triturated with 3:2 ethyl acetate/heptane (60 mL) for 30 minutes, and the solids were collected by filtration, rinsing with heptane, to provide C13 as a white solid. Yield: 22.08 g, 44.4 mmol, 88%. LCMS m/z 498.6 (M+1). $^1$H NMR (400 MHz, CD$_3$OD) δ 1.47 (s, 9H), 1.52 (s, 6H), 1.54 (s, 9H), 3.39 (dd, J=5.7, 2.5 Hz, 1H), 3.65 (dd, J=5.5, 5.5 Hz, 1H), 5.10 (dd, J=5.3, 2.5 Hz, 1H), 7.34 (s, 1H).

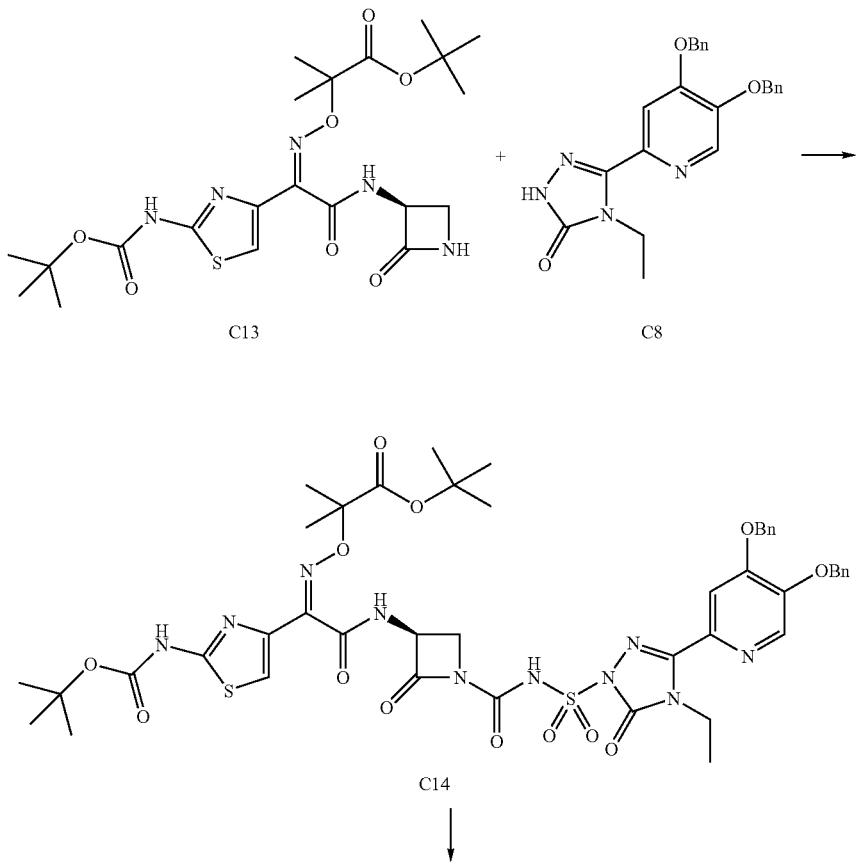

Scheme 6

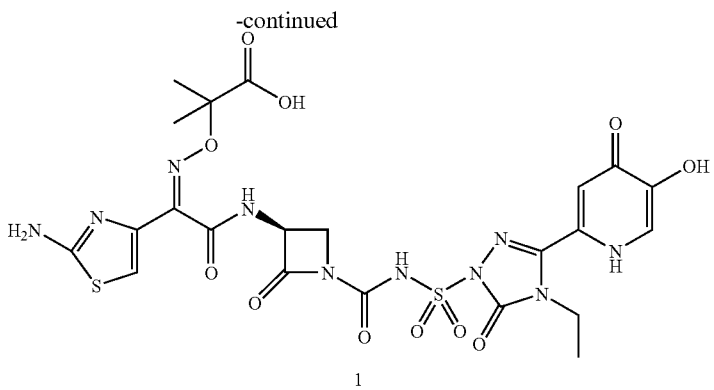

Step 6. Preparation of Preparation of 2-({[(1E)-1-(2-amino-1,3-thiazol-4-yl)-2-{[(3S)-1-({[4-ethyl-3-(5-hydroxy-4-oxo-1,4-dihydropyridin-2-yl)-5-oxo-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid (1).

A. Preparation of C14 (Coupling Method 1). To a stirred solution of C8 (180 mg/0.45 mmol) in 3 mL of tetrahydrofuran was added 6.0 equivalents of N-trimethylsilyl-N-methyltrifluoroacetamide (MSTFA, Aldrich ampoule) forming a pale yellow solution, which stirred at room temperature for 45 minutes. The mixture was then concentrated under reduced pressure and heated under vacuum (high vac) at 45° C. for 1 hour. Separately, to 0.223 g (0.45 mmol) of C13 dissolved in 4 mL dichloromethane and cooled to 0° C. was added 0.082 g (0.58 mmol/0.051 mL) of chlorosulfonylisocyanate and the resulting solution stirred at 0° C. for 30 minutes. At this point, tetrahydrofuran (3 mL) was added to the adduct of C8 and the resulting solution introduced to the CSI reaction via cannula. The resulting solution stirred at 0° C. for 1 hour then brought to room temperature and concentrated under reduced pressure. The crude material was cleaned up by column chromatography (silica-gel, 45 to 60% ethylacetated in heptane) affording 332 mg of C14 in a mixture that was carried forward without additional purification. LCMS m/z 1003.2 (M−1).

B. Preparation of compound 1. In a Parr bottle was placed 0.190 g (0.19 mmol) of C14 dissolved in 20 mL of methanol and the solution degassed with nitrogen gas. Palladium-black (0.063 g) was then added and mixture agitated under an atmosphere of 13 psi hydrogen at room temperature for 40 min (reaction complete by LCMS). The reaction mixture was then filtered through Celite® and concentrated to dryness in vacuo. The material was then carried on crude by dissolving in 10 mL of dichloromethane. To this solution was then added 10 mL of trifluoroacetic acid and the resulting mixture stirred at room temperature for 2 hours, at which time the reaction mixture was concentrated in vacuo. The crude product (1) was then purified by preparative HPLC (Symmetry C8, 3 to 23% acetonitrile in water with 0.1% formic acid modifier). Approximately 5 mg of 1 were collected following concentration to dryness in vacuo. LCMS m/z 669.4 (M+1). $^1$H NMR (400 MHz, CD$_3$OD) δ 1.01.2 (m, 6H), 1.3-1.5 (br. s, 5H), 3.97 (d, J=6.8 Hz, 2H), 4.88 (br. s, 1H), 6.81 (s, 1H), 7.32 (s, 1H), 7.99 (s, 1H), 9.05 (d, J=4.2 Hz, 1H).

Example 2

Preparation of 2-({[(1Z)-1-(2-amino-1,3-thiazol-4-yl)-2-({(3S)-1-[({4-[2-(dimethylamino)ethyl]-3-(5-hydroxy-4-oxo-1,4-dihydropyridin-2-yl)-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid (2)

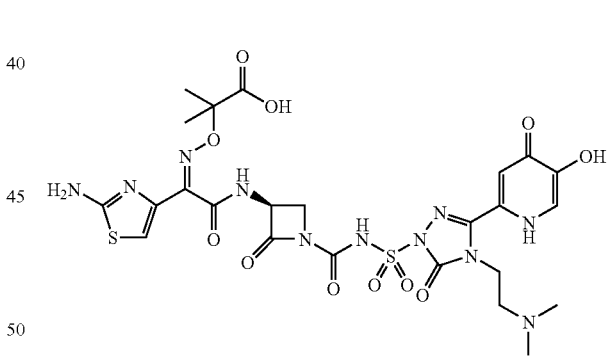

Compound 2 was prepared by the procedures depicted in scheme 7 and outlined in detail below.

Scheme 7
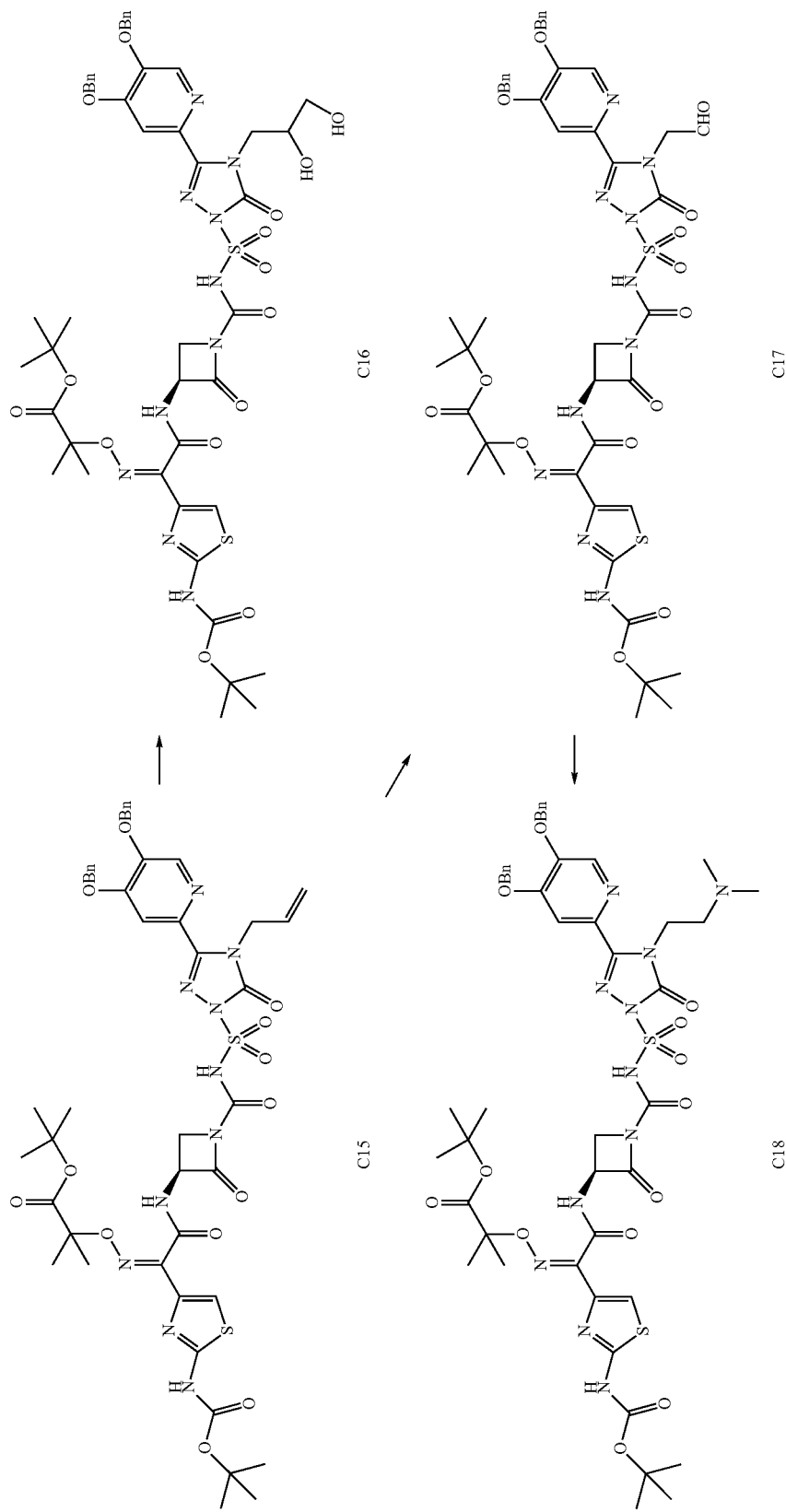

Step 1. Preparation of 2-({[(1Z)-1-(2-amino-1,3-thiazol-4-yl)-2-({(3S)-1-[({4-[2-(dimethylamino)ethyl]-3-(5-hydroxy-4-oxo-1,4-dihydropyridin-2-yl)-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid (2) and Diasteriomeric Diol Mixture (Example 10)

A. Preparation of C16. Compound C15 was prepared in an analogous manner to C14 in example 1 using coupling method 1. LCMS m/z 991.8 (M+1). $^1$H NMR (400 MHz, DMSO-$d_6$) δ 1.33-1.39 (m, 9H), 1.41-1.45 (br. s, 6H), 3.32-3.38 (m, 1H), 6.67 (t, J=8.2 Hz, 1H), 4.67 (m, 1H), 4.85-4.92 (m, 1H), 4.98 (d, J=5.8 Hz, 1H), 5.26 (d, J=9.3 Hz, 2H), 5.73-5.86 (m, 1H), 7.27-7.49 (m, 10H), 7.58 (s, 1H), 8.31 (s, 1H), 8.99 (d, J=9.34 Hz, 1H). To a stirred solution of C15 (0.30 g/0.3 mmol) in 5 mL of 9:1 acetone/water was added 0.138 g (1.18 mmol) N-methylmorpholine-N-oxide (NMO) followed by 0.746 g (0.09 mmol) of osmium tetroxide and the resulting mixture stirred 16 hours at room temperature. Another addition of NMO and osmium tetroxide were then added and mixture stirred an additional 24 hours, at which time the reaction was complete by LCMS. The reaction was filtered through Celite®, concentrated in vacuo then purified by column chromatography (silica; 30 to 100% ethylacetate in heptane then switched to 3 to 7% methanol in dichloromethane collecting 0.302 g of C16. LCMS m/z 1051.3 (M+1). $^1$H NMR (400 MHz, DMSO-$d_6$) δ 1.33-1.38 (m, 9H), 1.42 (s, 6H), 3.20-3.26 (m, 2H), 3.31-3.37 (m, 1H), 3.58-3.69 (m, 2H), 3.94-4.11 (m, 2H), 4.49-4.58 (m, 1H), 4.89 (br. s, 1H), 4.94 (dd, J=5.4 Hz, J=10.1 Hz, 1H), 5.24-5.29 (m, 4H), 7.27-7.48 (m, 10H), 7.52 (s, 1H), 8.31 (s, 1H), 8.98 (d, J=8.7 Hz, 1H). This material was then deprotected in an analogous manner to that described for C14 for preparing compound 1 in example 1 in order to prepare example 10.

B. Preparation of C17. In a flame dry flask was placed C15 (0.486 g, 0.48 mmol) dissolved in 8 mL of 3:1 dioxane/water and to this mixture was then added sodium periodate (0.311 g, 1.43 mmol) and osmium tetroxide (0.025 g, 0.003 mmol) and the resulting mixture stirred for 16 hours at room temperature (reaction complete by LCMS). The reaction mixture was then partitioned between saturated sodium bicarbonate and ethylacetate. The organic layer was washed with saturated brine, dried over sodium sulfate, filtered and concentrated to dryness in vacuo. The crude product was then purified by column chromatography (silica-gel, 30 to 100% ethylacetate in heptane then switched to 3 to 7% methanol in dichloromethane collecting 0.230 g of C17, which appears by $^1$H NMR to exist as a hydrate. LCMS m/z 1019.9 (M+1). $^1$H NMR (400 MHz, CD$_3$OD) δ 1.38-1.56 (m, 24H), 3.72 (t, J=4.7 Hz, 1H), 3.84 (t, J=4.1 Hz, 1H), 3.89-3.56 (m, 1H), 4.16-4.22 (m, 2H), 4.45 (t, J=5.3 Hz, 1H), 4.72-4.78 (m, 1H), 5.00-5.09 (m, 1H), 5.19-5.29 (m, 4H), 7.19-7.49 (m, 10H), 7.77 (s, 1H), 8.11 (s, 1H), 8.22 (d, J=9.4 Hz, 1H).

C. Preparation of C18 and compound 2. To a stirred solution of C17 (1.22 g, 1.20 mmol) in 10 mL tetrahydrofuran was added dimethylamine (0.098 g, 1.2 mmol) and 3 equivalents of glacial acetic acid (0.215 mL, 3.59 mmol) and the resulting solution stirred at room temperature for 2 hours. Sodium triacetoxyborohydride (0.532 g, 2.51 mmol) was then added and the resulting mixture stirred at room temperature for 18 hours. The reaction mixture was partitioned between saturated sodium bicarbonate and ethylacetate, the organic layer washed with saturated brine, dried over sodium sulfate, filtered and concentrated to dryness in vacuo. The crude product was purified by column chromatography (silica-gel, 30 to 100% ethylacetate in heptane then switched to 5 to 10% methanol in dichloromethane) collecting 0.340 g of C18. LCMS m/z 1048.9 (M+1). $^1$H NMR (400 MHz, CD$_3$OD) δ 1.38-1.54 (m, 24H), 2.44 (s, 1H), 2.85 (s, 6H), 3.40 (br. s, 1H), 3.71-3.77 (m, 1H), 3.90 (t, J=6.0 Hz, 1H), 4.46 (br. s, 2H), 5.03 (s, 2H), 5.18-5.26 (m, 4H), 7.20-7.35 (m, 9H), 7.40 (d, J=7.0 Hz, 2H), 7.65 (s, 1H), 8.21 (s, 1H). Compound 2 was then prepared from C18 by deprotection and HPLC purification in an analogous manner to that described for compound 1 of Example 1. LCMS m/z 712.5 (M+1). $^1$H NMR (400 MHz, DMSO-$d_6$) δ 1.39 (s, 6H), 2.50 (s, 6H), 3.30-3.45 (m, assumed 3H, obscured by water peak), 3.68 (m, 1H), 4.37 (m, 2H), 6.70 (s, 1H), 7.31 (br s, 2H), 7.42 (s, 1H), 8.03 (s, 1H), 8.98 (d, J=7.0 Hz, 1H), 9.99 (br s, 1H), 10.88 (br s, 1H).

Example 3

Preparation of 2-({[(1Z)-1-(2-amino-1,3-thiazol-4-yl)-2-({(3S)-1-[({4-[(2R)-2,3-dihydroxypropyl]-3-(5-hydroxy-4-oxo-1,4-dihydropyridin-2-yl)-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid, disodium salt (3)

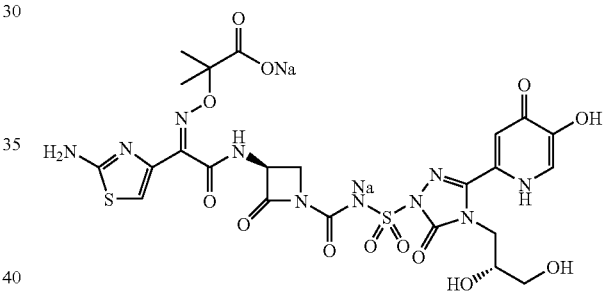

Compound 3 was prepared by the procedures depicted in Schemes 8 to 10 and described in detail below.

Scheme 8

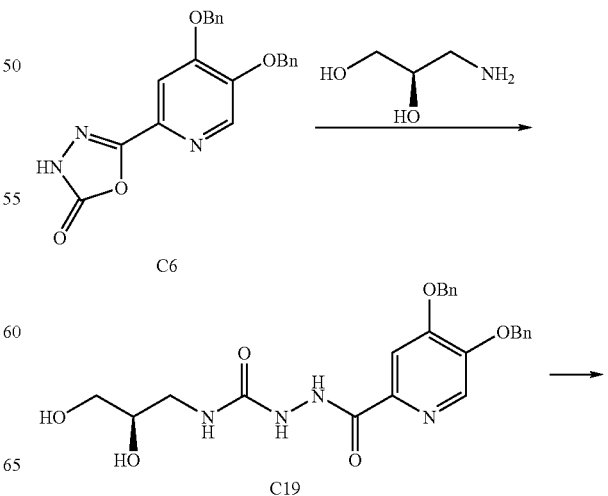

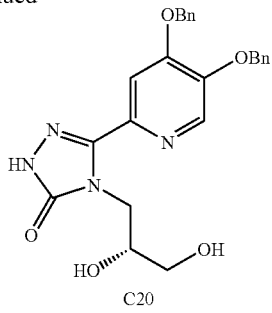

Step 1. Preparation of 5-[4,5-bis(benzyloxy)pyridin-2-yl]-4-[(2R)-2,3-dihydroxypropyl]-2,4-dihydro-3H-1,2,4-triazol-3-one (C20)

A. Preparation of 2-{[4,5-bis(benzyloxy)pyridin-2-yl]carbonyl}-N-[(2R)-2,3-dihydroxypropyl]hydrazinecarboxamide (C19). (2R)-3-Aminopropane-1,2-diol (0.291 g, 3.19 mmol) was added to a suspension of C6 (1.0 g, 2.66 mmol) in tetrahydrofuran (50 mL), and the mixture was heated to 60° C. for 20 hours. After cooling to room temperature, the suspension was filtered, and the solid was washed with tetrahydrofuran (3×5 mL) to afford C19 as a white solid. Yield: 1.07 g, 2.29 mmol, 86%. LCMS m/z 467.2 (M+1). $^1$H NMR (400 MHz, DMSO-$d_6$) δ 2.93 (m, 1H), 3.19 (m, 1H), 3.27 (m, 2H), 3.44 (m, 1H), 4.53 (t, J=5.8 Hz, 1H), 4.77 (d, J=4.8 Hz, 1H), 5.33 (s, 4H), 6.31 (t, J=5.5 Hz, 1H), 7.31-7.48 (m, 10H), 7.69 (s, 1H), 8.01 (br s, 1H), 8.28 (s, 1H), 10.04 (br s, 1H).

B. Preparation of C20. A solution of C19 (3.00 g, 6.43 mmol) in aqueous potassium hydroxide (1.6 M, 40.2 mL, 64.3 mmol) was heated at 100° C. for 13 hours, after which it was cooled to 0° C., diluted with water (100 mL) and acidified to pH 7 with concentrated hydrochloric acid. The resulting solid was filtered and washed with water (3×10 mL) to afford C20, contaminated with about 30% of the hydrolysis product 4,5-bis(benzyloxy)pyridine-2-carboxylic acid. Yield: 2.66 g, <5.93 mmol, <92%. LCMS m/z 449.2 (M+1) and 336.1 (M+1 for the hydrolysis product). $^1$H NMR (400 MHz, DMSO-$d_6$) δ 3.28 (m, 2H), 3.70 (m, 1H), 4.05 (dd, half of ABX pattern, J=13.7, 5.0 Hz, 1H), 4.12 (dd, half of ABX pattern, J=13.7, 8.0 Hz, 1H), 4.61 (v br s, 1H), 5.01 (br s, 1H), 5.28 (s, 2H), 5.31 (s, 2H), 7.32-7.48 (m, 10H), 7.58 (s, 1H), 8.32 (s, 1H), 12.03 (br s, 1H). Selected peaks for hydrolysis product: 5.29 (s), 7.70 (s), 8.28 (s).

Scheme 9

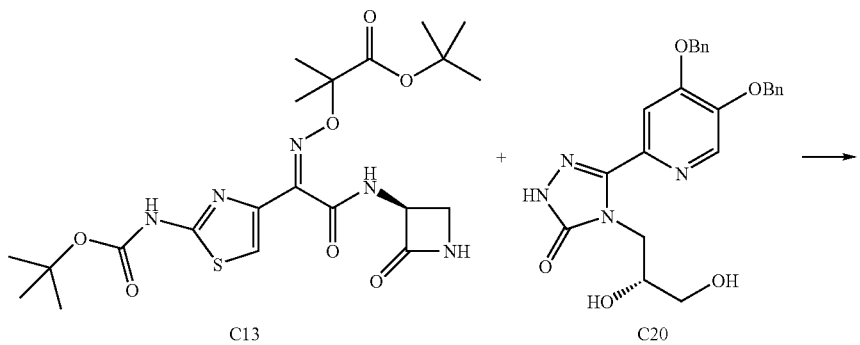

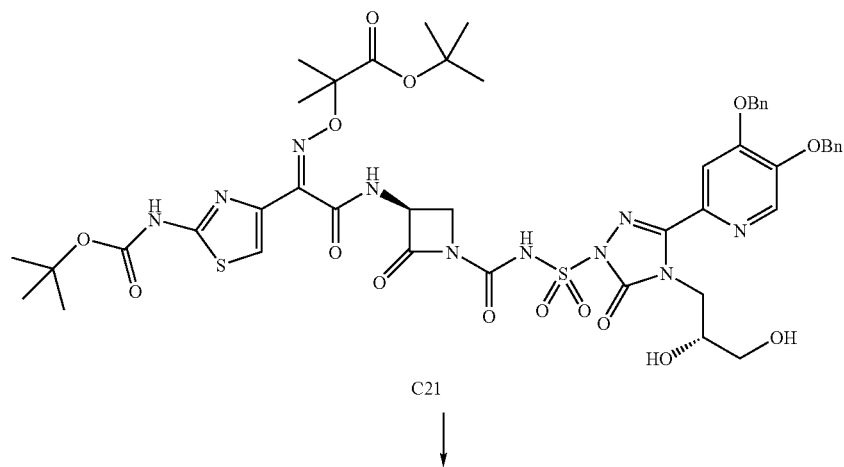

C21

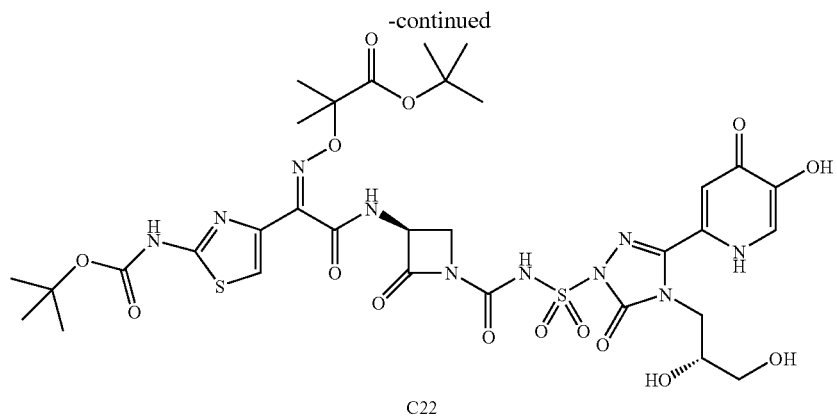

C22

Step 2. Preparation of tert-butyl 2-({[(1Z)-1-{2-[(tert-butoxycarbonyl)amino]-1,3-thiazol-4-yl}-2-({(3S)-1-[({4-[(2R)-2,3-dihydroxypropyl]-3-(5-hydroxy-4-oxo-1,4-dihydropyridin-2-yl)-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoate (C22)

A. Preparation of tert-butyl 2-({[(1Z)-2-({(3S)-1-[({3-[4,5-bis(benzyloxy)pyridin-2-yl]-4-[(2R)-2,3-dihydroxypropyl]-5-oxo-4,5-dihydro-1H-1,2,4-triazol-1-yl}sulfonyl)carbamoyl]-2-oxoazetidin-3-yl}amino)-1-{2-[(tert-butoxycarbonyl)amino]-1,3-thiazol-4-yl}-2-oxoethylidene]amino}oxy)-2-methylpropanoate (C21). A mixture of C20 (4.00 g, 8.92 mmol) in tetrahydrofuran (35 mL) was treated with 2,2,2-trifluoro-N-methyl-N-(trimethylsilyl)acetamide (MSTFA, 98%, 10.2 mL, 53.7 mmol). After 45 minutes of stirring, the light yellow milky mixture was concentrated in vacuo at 60° C. for 1 hour, then dried under vacuum at 60° C. for 1.5 hours. In a separate flask, a suspension of C13 (4.88 g, 9.81 mmol) in dichloromethane (32 mL) was cooled to 0° C., treated drop-wise with isocyanatosulfuryl chloride (chlorosulfonyl isocyanate, 95%, 0.929 mL, 10.7 mmol) and allowed to stir for 30 minutes under ice-cooling. The material derived from C20 was dissolved in tetrahydrofuran (8 mL), cooled to 0° C. The ice-cooled C13-containing reaction mixture was then transferred into this solution via cannula. After stirring at 0° C. for 1 hour, then at room temperature for 1.5 hours, the reaction mixture was quenched with methanol (5 mL), stirred for 10 minutes and concentrated in vacuo. The residue was purified by silica gel chromatography (Gradient: 40-100% ethyl acetate in heptane, then 0-12% methanol in ethyl acetate) to afford C21 as a solid. Yield: 3.85 g, 3.66 mmol, 41%. LCMS m/z 1051.4 (M+1). $^1$H NMR (400 MHz, DMSO-$d_6$) δ 1.38 (s, 9H), 1.39 (s, 6H), 1.46 (s, 9H), 3.3 (obscured by HOD signal), 3.66 (m, 1H), 3.70 (dd, J=6.3, 6.3 Hz, 1H), 4.00-4.13 (m, 2H), 4.56 (m, 1H), 4.93 (m, 2H), 5.29 (s, 2H), 5.30 (s, 2H), 7.25 (s, 1H), 7.31-7.50 (m, 10H), 7.57 (s, 1H), 8.35 (s, 1H), 9.02 (d, J=8.5 Hz, 1H), 11.84 (br s, 1H).

B. Preparation of C22. A solution of C21 (0.460 g, 0.438 mmol) in tetrahydrofuran (10 mL) and acetic acid (0.1 mL) was degassed and flushed with nitrogen (3×) and treated with Pd black (134 mg). The mixture was hydrogenated using a Parr shaker under 36 psi hydrogen at room temperature for 4 hours (reaction complete by LCMS). The sample was filtered through acid washed cellulose powder and washed with THF to give a pale red filtrate, which was concentrated to dryness in vacuo affording 0.382 g (100%) as a red solid. LCMS m/z 871.8 (M+1). $^1$H NMR (500 MHz, DMSO-$d_6$) δ 1.39 (s, 9H), 1.40 (s, 6H), 1.46 (s, 9H), 3.29 (m, 2H), 3.39 (dd, J=6.3, 3.3 Hz, 1H), 3.65 (HOD lump obscures signal), 3.71 (m, 1H, estimated), 3.94 (m, 2H, estimated), 4.92 (m, 1H), 7.26 (s, 1H), 7.39 (s, 1H), 8.02 (s, 1H), 9.01 (d, J=8.0 Hz, 1H), 11.82 (br s, 1H).

Scheme 10

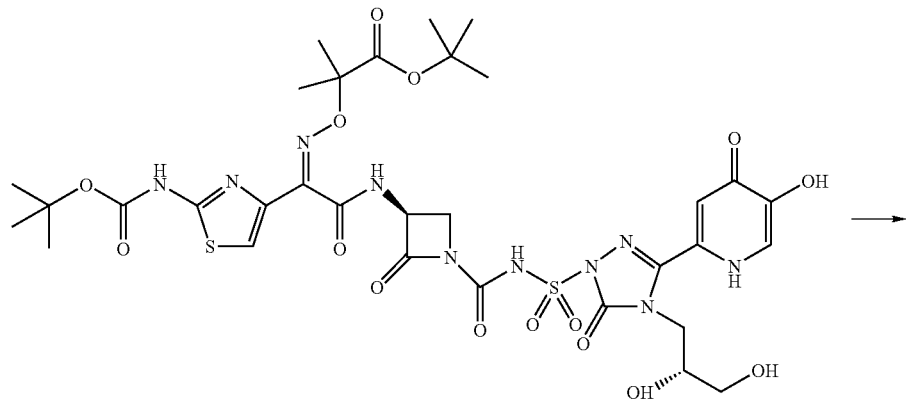

C22

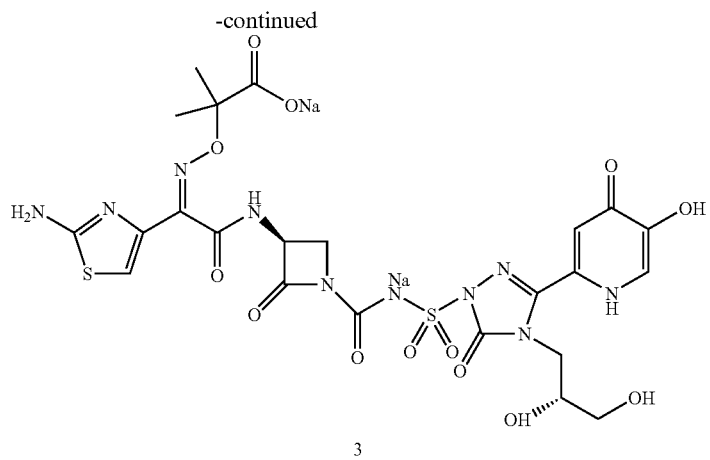

3

Step 3. Preparation of 2-({[(1Z)-1-(2-amino-1,3-thiazol-4-yl)-2-({(3S)-1-[({4-[(2R)-2,3-dihydroxypropyl]-3-(5-hydroxy-4-oxo-1,4-dihydropyridin-2-yl)-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid, disodium salt (3)

A. Preparation of compound 3. Trifluoroacetic acid (13 mL) was added to a cooled (0° C.) solution of C22 (2.54 g, 2.91 mmol) in 13 mL of dichloromethane. The reaction mixture was stirred at room temperature for 2 hours and then transferred slowly via a teflon cannula to another round bottom flask containing 186 mL of a 2:1 mixture of heptane/methyl-t-butyl ether (MTBE) resulting in a fine precipitate. The solids were collected by filtration, washed with heptane/MTBE (2:1) and dried in vacuo affording 1.82 g (88%) of the trifluoroacetic acid salt of 3 as a rose colored solid. A portion of this material (2.42 g) was then purified by reverse phase chromatography using an Isco Rf Chromatography system employing a RediSep® Rf C18 column (130 g), loading the crude trifluoroacetic acid salt as a solution in dimethylsulfoxide (1.5 mL) in two batches. The gradient was 5% to 30% water (0.1% Formic acid)/acetonitrile (0.1% Formic acid). The product came off the column at 15-18% acetonitrile. The fractions were pooled and the solvent was removed under reduced pressure affording 0.847 g (35%) of material as a white solid. The solid was sonicated in methanol (4 times) and solvent was removed (done to remove formic acid). The $^1$H NMR confirms the free-form product with a minimal amount of formic acid. LCMS m/z 715.0 (M+1). $^1$H NMR (500 MHz, DMSO-$d_6$) δ 1.42 (s, 3H), 1.43 (s, 3H), 3.28 (m, 2H), 3.38 (dd, J=6.3, 3.4 Hz, 1H), 3.65 (m, 1H), 3.70 (m, 1H), 3.95 (br d, J=6.5 Hz, 2H), 4.91 (m, 1H), 6.79 (s, 1H), 7.36 (s, 1H), 8.01 (s, 1H), 9.03 (d, J=8.3 Hz, 1H). To a slurry of 1.20 g (1.65 mmol) of the free-form acid in 30 mL of deionized water at 0° C. was slowly added 0.277 g (3.30 mmol) of sodium bicarbonate dissolved in 6 mL of deionized water (solids completely dissolve upon addition of the sodium bicarbonate solution). The resulting solution was then frozen and lyophilized affording 1.12 g of the disodium salt as a light pink lyophile. LCMS m/z 715.6 (M+1). $^1$H NMR (500 MHz, D$_2$O) δ 1.31 (s, 3H), 1.32 (s, 3H), 3.44 (dd, ½ABX, J=12.1 Hz, 4.8 Hz, 1H), 3.48 (dd, ½ABX, J=11.8 Hz, 4.0 Hz, 1H), 3.65 (dd, J=7.3 Hz, 3.3 Hz, 1H), 3.73-3.92 (m, 3H), 4.90 (dd, J=3.2 Hz, 3.2 Hz, 1H), 6.79 (s, 1H), 6.97 (s, 1H), 7.72 (s, 1H).

Example 4

Preparation of 2-({[(1Z)-2-{[(3S)-1-({[4-(2-amino-2-oxoethyl)-3-(5-hydroxy-4-oxo-1,4-dihydropyridin-2-yl)-5-oxo-4,5-dihydro-1H-1,2,4-triazol-1-yl]sulfonyl}carbamoyl)-2-oxoazetidin-3-yl]amino}-1-(2-amino-1,3-thiazol-4-yl)-2-oxoethylidene]amino}oxy)-2-methylpropanoic acid, disodium salt (4)

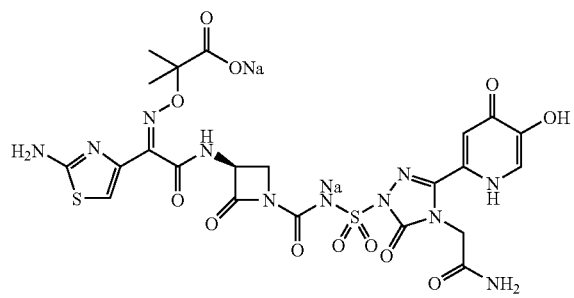

4

Compound 4 was prepared by the procedures depicted in Schemes 11 to 13 and described in detail below.

Scheme 11

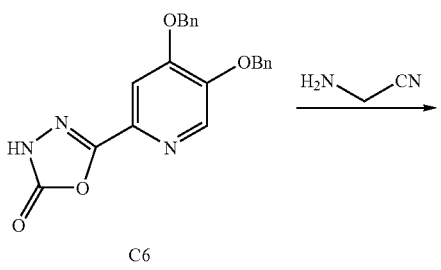

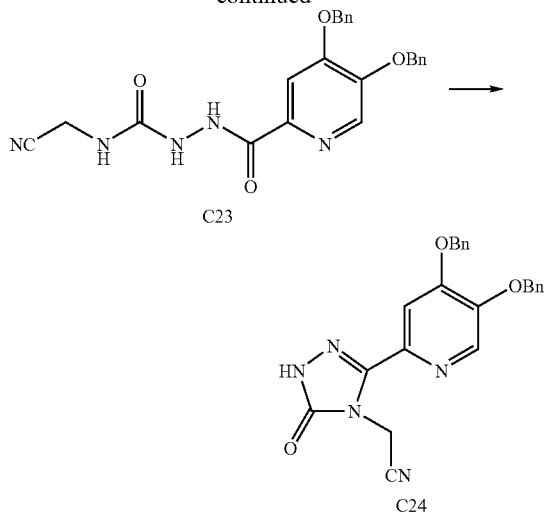

Step 1. Preparation of {3-[4,5-bis(benzyloxy)pyridin-2-yl]-5-oxo-1,5-dihydro-4H-1,2,4-triazol-4-yl}acetonitrile (C24)

A. Preparation of 2-{[4,5-bis(benzyloxy)pyridin-2-yl]carbonyl}-N-(cyanomethyl)hydrazinecarboxamide (C23). Aminoacetonitrile (0.11 g, 1.92 mmol) and triethylamine (0.162 g, 1.60 mmol) were added drop-wise over one minute to a suspension of C6 (0.60 g, 1.6 mmol) in tetrahydrofuran (5 mL), and the mixture was heated to 55° C. for 20 hours. Additional aminoacetonitrile (0.108 g, 1.92 mmol) and triethylamine (0.162 g, 1.60 mmol) were added and heating was continued at 55° C. for 20 hours. After being cooled to 0° C. with an ice-bath, the suspension was filtered, and the solid was washed with tetrahydrofuran, and dried under vacuum to afford C23 as a solid. Yield: 0.550 g, 1.27 mmol, 79%. LCMS m/z 430.3 (M−1). $^1$H NMR (400 MHz, DMSO-$d_6$) δ 4.00 (d, J=5.5 Hz, 2H), 5.33 (s, 2H), 5.34 (s, 2H), 7.30-7.48 (m, 10H), 7.70 (s, 1H), 8.27 (s, 1H), 8.38 (br s, 1H), 10.18 (br s, 1H).

B. Preparation of C24 (Cyclization Method 2). 2,2,2-Trifluoro-N-methyl-N-(trimethylsilyl)acetamide (MSTFA, 98%, 8 mL, 37 mmol) and C23 (0.310 g, 0.728 mmol), were combined in a microwave tube and heated to 150° C. for 15 minutes. This process was repeated six times for a combined total of 2.20 g of C23 employed. The reactions were combined and concentrated in vacuo, and the residue was purified by silica gel chromatography (Gradient: 30-50% ethyl acetate in heptane) to afford C24 as a solid. Yield: 1.1 g, 2.66 mmol, 52%. LCMS m/z 414.2 (M+1). $^1$H NMR (400 MHz, DMSO-$d_6$) δ 5.17 (s, 2H), 5.32 (s, 2H), 5.34 (s, 2H), 7.29-7.50 (m, 10H), 7.64 (s, 1H), 8.36 (s, 1H), 12.34 (s, 1H).

Scheme 12

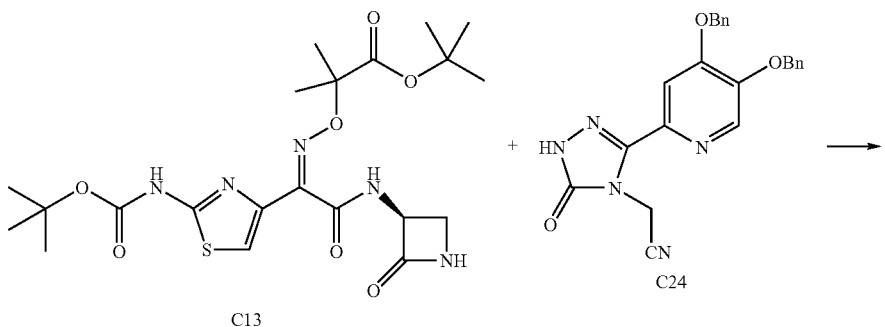

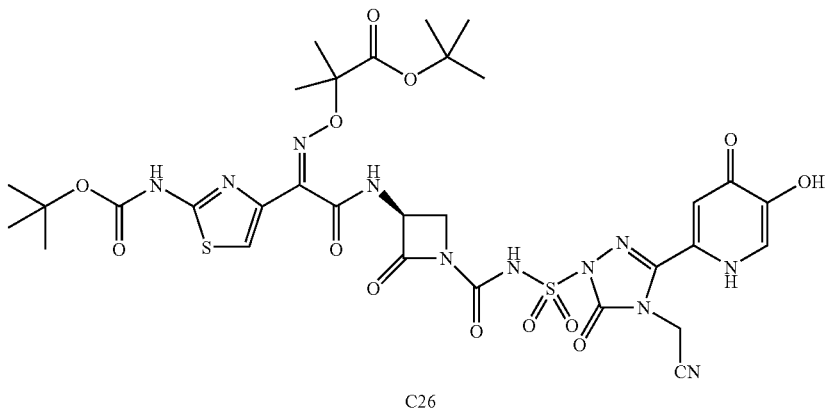

C26

Step 2. Preparation of tert-butyl 2-({[(1Z)-1-{2-[(tert-butoxycarbonyl)amino]-1,3-thiazol-4-yl}-2-{[(3S)-1-({[4-(cyanomethyl)-3-(5-hydroxy-4-oxo-1,4-dihydropyridin-2-yl)-5-oxo-4,5-dihydro-1H-1,2,4-triazol-1-yl]sulfonyl}carbamoyl)-2-oxoazetidin-3-yl]amino}-2-oxoethylidene]amino}oxy)-2-methylpropanoate (C26)

A. Preparation of tert-butyl 2-({[(1Z)-2-({(3S)-1-[({3-[4,5-bis(benzyloxy)pyridin-2-yl]-4-(cyanomethyl)-5-oxo-4,5-dihydro-1H-1,2,4-triazol-1-yl}sulfonyl)carbamoyl]-2-oxoazetidin-3-yl}amino)-1-{2-[(tert-butoxycarbonyl)amino]-1,3-thiazol-4-yl}-2-oxoethylidene]amino}oxy)-2-methylpropanoate (C25). Compound C25 was prepared according to the general procedure for the synthesis of C21 in Example 3, except that C24 was used in place of C20. The crude material was purified by silica gel chromatography (Gradient: 35-75% ethyl acetate in heptane) to afford C25. Yield: 1.64 g, 1.61 mmol, 21%. This material was used in the next step without further purification. LCMS m/z 1016.5 (M+1).

B. Compound C26. Compound. C26 was prepared according to the general procedure for the synthesis of C22 in Example 3, except that C25 was used in place of C21, and the reaction was hydrogenated at 25 psi for 1.5 hours to afford C19 as a brown solid. Yield: 0.635 g, 0.759 mmol, 98%. LCMS m/z 836.3 (M+1).

Scheme 13

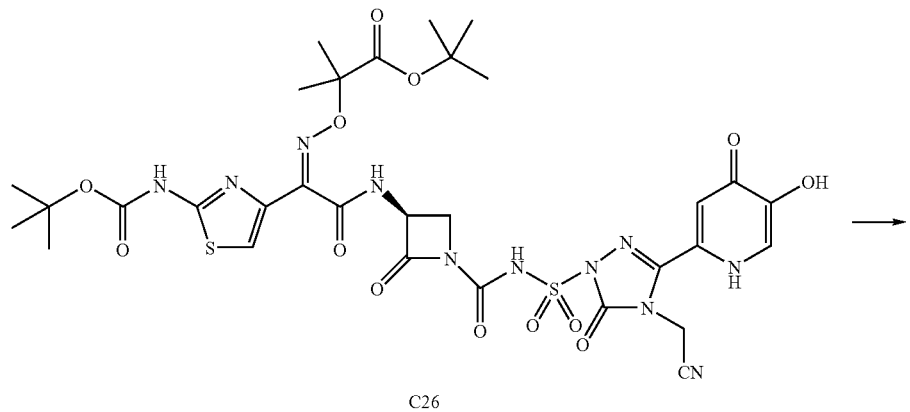

C26

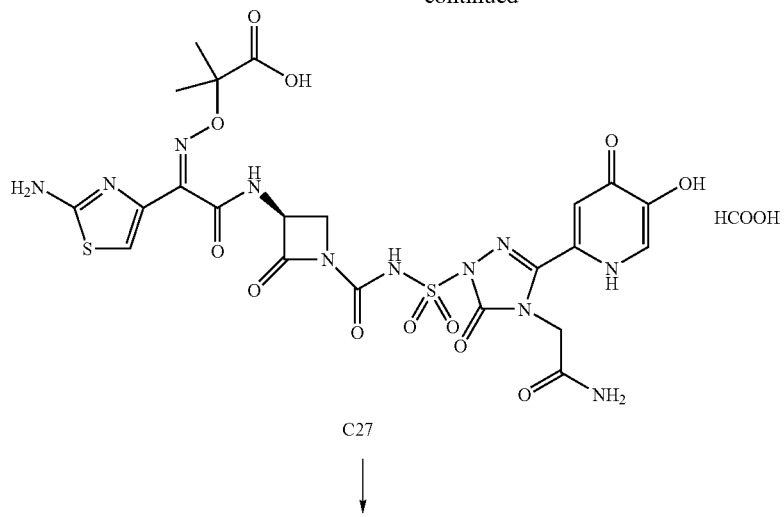

C27

↓

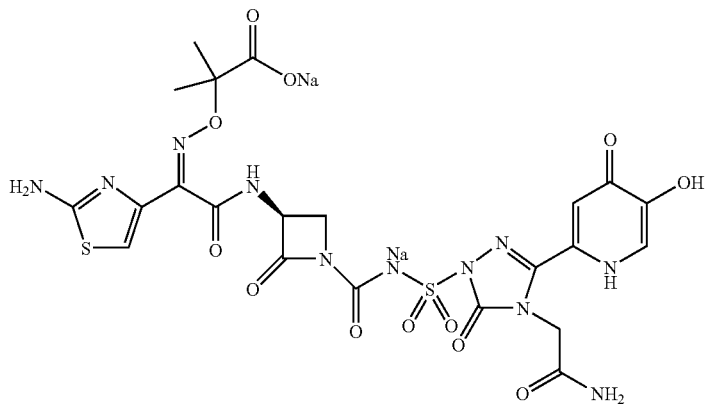

4

Step 3. Preparation of 4

A. Preparation of 2-({[(1Z)-2-{[(3S)-1-({[4-(2-amino-2-oxoethyl)-3-(5-hydroxy-4-oxo-1,4-dihydropyridin-2-yl)-5-oxo-4,5-dihydro-1H-1,2,4-triazol-1-yl]sulfonyl}carbamoyl)-2-oxoazetidin-3-yl]amino}-1-(2-amino-1,3-thiazol-4-yl)-2-oxoethylidene]amino}oxy)-2-methylpropanoic acid (C27). Compound C27 was prepared according to the general procedure for the synthesis of 3 in Example 3, except that C26 was used in place of C22. Also, the crude trifluoroacetic acid salt of compound 4 was generated by evaporation of the trifluoroacetic acid/dichloromethane solution as opposed to using the precipitation technique employed in example 3. The crude product was dissolved in dimethyl sulfoxide to a concentration of 100 mg/mL, filtered, and purified by preparative HPLC (column: Waters Symmetry C8, 5 μm, 30×50 mm; Solvent A: 0.1% aqueous formic acid; Solvent B: 0.1% formic acid in acetonitrile. Gradient: 3% to 22% B). The fractions that pertained to the desired product were combined, cooled to −78° C. and lyophilized to provide C27 as a pink solid. Yield: 0.078 g, 0.11 mmol, 12%. LCMS m/z 698.9 (M+1). $^1$H NMR (400 MHz, DMSO-$d_6$) δ 1.38 (br s, 6H), 3.33 (m, 1H), 3.65 (m, 1H), 4.61 (s, 2H), 4.88 (m, 1H), 6.74 (br s, 1H), 7.03 (br s, 1H), 7.30 (s, 1H), 7.89 (s, 1H), 8.99 (d, J=7.42 Hz, 1H).

B. Preparation of 4. A solution of C27 (78 mg, 0.11 mmol) in a mixture of acetonitrile (5 mL) and water (45 mL) was cooled to 0° C. and sodium bicarbonate (18.8 mg, 0.224 mmol) was added. The mixture was vigorously stirred for ten minutes at 0° C. The suspension was then cooled to −78° C. (using a dry ice/acetone bath) and lyophilized to afford 4 as a pink solid. Yield: 0.079 g, 0.106 mmol, 95%. $^1$H NMR (400 MHz, DMSO-$d_6$) δ 1.42 (s, 3H), 1.50 (s, 3H), 3-3.5 ppm obscured by water peak, 3.78 (m, 1H), 4.57 (d, J=16.4 Hz, 1H), 4.72 (d, J=16.4 Hz, 1H), 5.15 (m, 1H), 6.78 (s, 1H), 6.99 (br. s, 1H), 7.18 (br s, 3H), 7.38 (br s, 1H), 7.41 (s, 1H), 7.81 (s, 1H).

Example 5

Preparation of 2-({[(1Z)-1-(2-amino-1,3-thiazol-4-yl)-2-({(3S)-1-[({-4-[(2S)-2,3-dihydroxypropyl]-3-(5-hydroxy-4-oxo-1,4-dihydropyridin-2-yl)-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid, disodium salt (5)

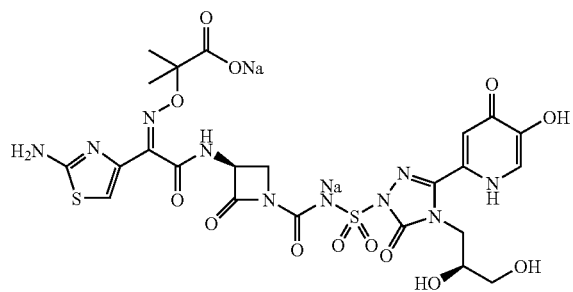

Compound 5 was prepared by the procedures depicted in Schemes 14 to 16 and described in detail below.

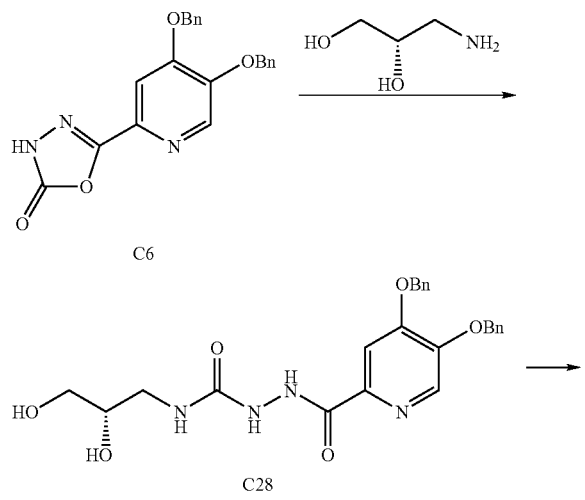

Step 1. Preparation of 5-[4,5-bis(benzyloxy)pyridin-2-yl]-4-[(2S)-2,3-dihydroxypropyl]-2,4-dihydro-3H-1,2,4-triazol-3-one (C29)

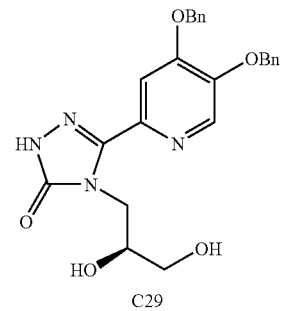

A. Preparation of 2-{[4,5-bis(benzyloxy)pyridin-2-yl]carbonyl}-N-[(2S)-2,3-dihydroxypropyl]hydrazinecarboxamide (C28). Compound C28 was prepared according to the general procedure for the synthesis of C19 in Example 3, except that (2S)-3-aminopropane-1,2-diol was used in place of (2R)-3-aminopropane-1,2-diol. Compound C28 was obtained as a yellow solid. Additional product was obtained by removing the solvent from the filtrate in vacuo to afford a yellow solid (8.58 g), which was slurried in tetrahydrofuran (50 mL), heated to reflux and then filtered to afford a second crop of C28. The combined yield for C28 was 16.73 g, 35.88 mmol, 90%. LCMS m/z 467.2 (M+1). $^1$H NMR (500 MHz, DMSO-$d_5$) δ 2.91 (m, 1H), 3.20 (m, 1H), 3.28 (m, 2H), 3.44 (m, 1H), 5.31 (s, 2H), 5.32 (s, 2H), 6.49 (m, 1H), 7.31-7.48 (m, 10H), 7.69 (s, 1H), 8.25 (s, 1H), B. Preparation of C29. Compound C29 was prepared according to the general procedure for the synthesis of C20 in Example 3, except that C28 was used in place of C19. The crude product was heated with methanol (100 mL), the hot mixture was filtered, and the filtrate concentrated to 20 mL. The resulting solid was collected by filtration to afford C29. Yield: 150 mg, 0.334 mmol, 22%. LCMS m/z 449.2 (M+1). NMR (400 MHz, DMSO-$d_6$) δ 3.28 (m, 2H), 3.70 (m, 1H), 4.09 (t, J=5.8 Hz, 1H), 5.01 (d, J=5.4 Hz, 1H), 5.27 (s, 2H), 5.31 (s, 2H), 7.32-7.49 (m, 10H), 7.58 (s, 1H), 8.32 (s, 1H), 12.03 (br s, 1H).

Scheme 15
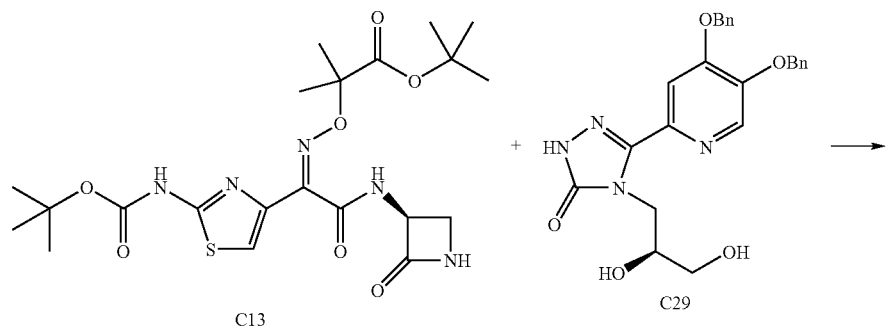
C13 + C29 →
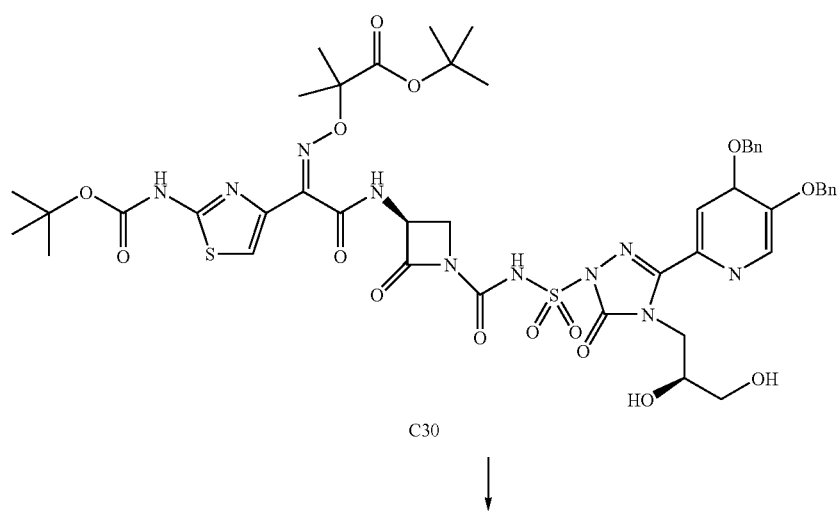
C30
↓
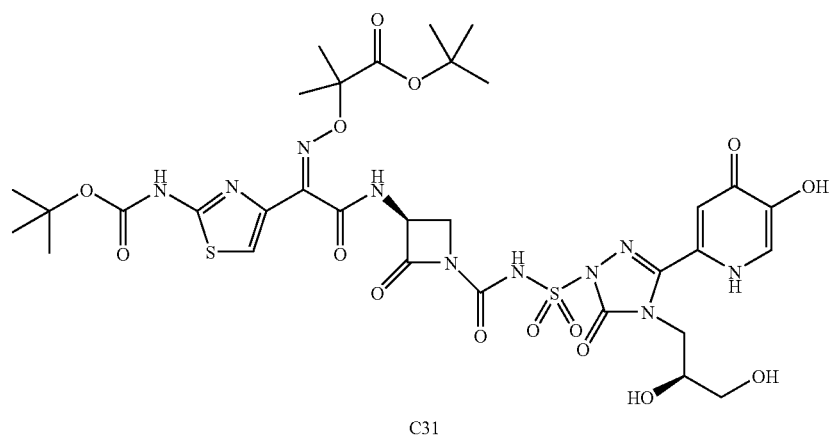
C31

Step 2. Preparation of tert-butyl 2-({[(1Z)-1-{2-[(tert-butoxycarbonyl)amino]-1,3-thiazol-4-yl}-2-({(3S)-1-[({4-[(2S)-2,3-dihydroxypropyl]-3-(5-hydroxy-4-oxo-1,4-dihydropyridin-2-yl)-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoate (C31)

A. Preparation of tert-butyl 2-({[(1Z)-2-({(3S)-1-[({3-[4,5-bis(benzyloxy)pyridin-2-yl]-4-[(2S)-2,3-dihydroxypropyl]-5-oxo-4,5-dihydro-1H-1,2,4-triazol-1-yl}sulfonyl)carbamoyl]-2-oxoazetidin-3-yl}amino)-1-{2-[(tert-butoxycarbonyl)amino]-1,3-thiazol-4-yl}-2-oxoethylidene]amino}oxy)-2-methylpropanoate (C30). Compound C30 was prepared according to the general procedure for the synthesis of C21 in Example 3, except that C29 was used in place of C20. After the reaction was quenched with methanol and concentrated in vacuo, the residue was purified by silica gel chromatography (Gradient: 25-100% ethyl acetate in heptane, then 0-7% methanol in ethyl acetate) to afford C30 as a solid. Yield: 5.41 g, 5.14 mmol, 53%. LCMS m/z 1051.7 (M+1). $^1$H NMR (400 MHz, DMSO-$d_6$) δ 1.38 (s, 9H), 1.40 (s, 3H), 1.40 (s, 3H), 1.46 (s, 9H), 3.28 (m, 2H), 3.39 (dd, J=6.1, 3.2 Hz, 1H), 3.68 (m, 2H), 4.03 (m, 1H), 4.11 (m, 1H), 4.92 (m, 1H), 5.28 (s, 2H), 5.30 (s, 2H), 7.25 (s, 1H), 7.31-7.50 (m, 10H), 7.58 (s, 1H), 8.35 (s, 1H), 9.00 (d, J=8.3 Hz, 1H).

B. Preparation of C31. Compound C31 was prepared according to the general procedure for the synthesis of C22 in Example 3, except that C30 was used in place of C21, and the reaction was hydrogenated at 25 psi for 1.5 hour to afford C31 as a red solid. Yield: 3.49 g, 4.00 mmol, 95%. LCMS m/z 871.6 (M+1).

Scheme 16

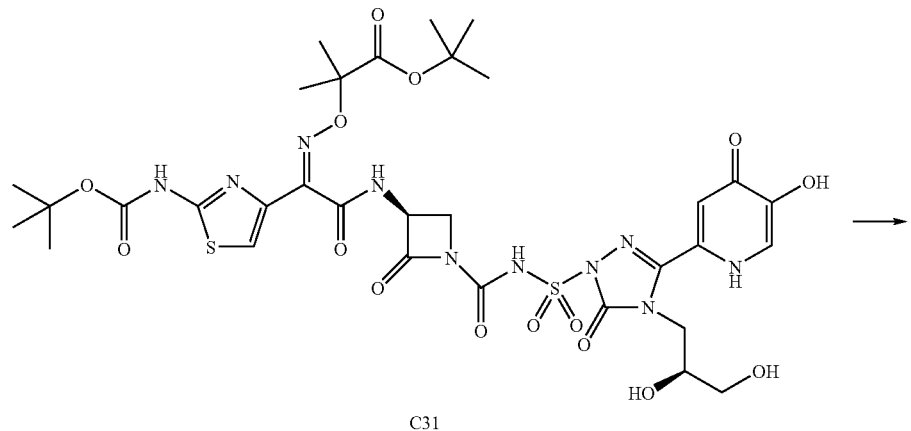

C31

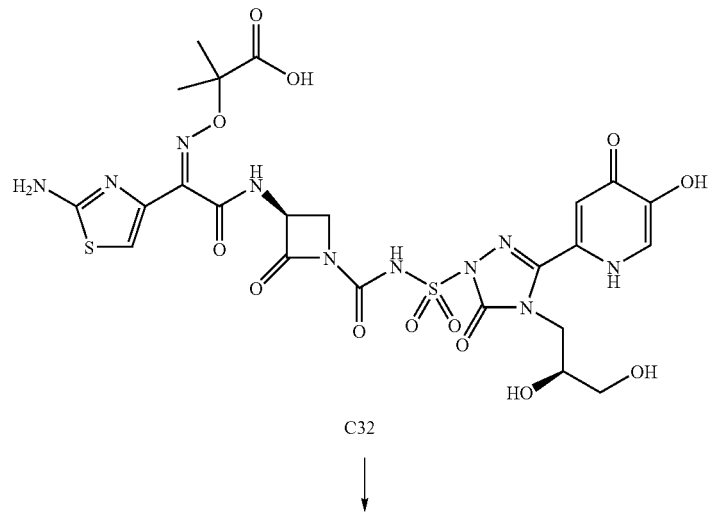

C32

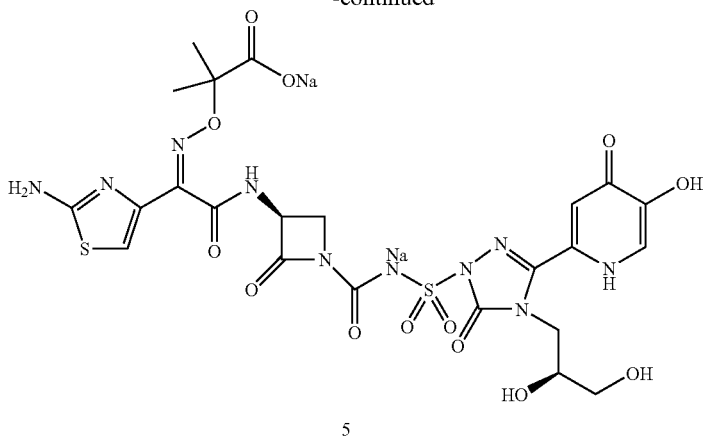

5

Step 3. Preparation of 2-({[(1Z)-1-(2-amino-1,3-thiazol-4-yl)-2-({(3S)-1-[({-4-[(2S)-2,3-dihydroxypropyl]-3-(5-hydroxy-4-oxo-1,4-dihydropyridin-2-yl)-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid, disodium salt (5)

A. Preparation of 2-({[(1Z)-1-(2-amino-1,3-thiazol-4-yl)-2-({(3S)-1[({4-[(2S)-2,3-dihydroxypropyl]-3-(5-hydroxy-4-oxo-1,4-dihydropyridin-2-yl)-5-oxo-4,5-dihydro-1H-1,2,4-triazol-1-yl}sulfonyl)carbamoyl]-2-oxoazetidin-3-yl}amino-2-oxoethylidene]amino}oxy)-2methylpropanoic acid C32. Compound C32 was prepared according to the general procedure for the synthesis of 3 in Example 3, except that C31 was used in place of C22. The crude product was dissolved in dimethyl sulfoxide to a concentration of 100 mg/mL, filtered, and purified by preparative HPLC (column: Waters® Symmetry C8, 5 μm, 30×50 mm; Solvent A: 0.1% aqueous formic acid; Solvent B: 0.1% formic acid in acetonitrile. Gradient: 3% to 23% B). The fractions that pertained to the desired product were concentrated in vacuo, keeping the water bath <30° C., to provide a solid. This solid was dissolved in a mixture of acetonitrile (10 mL) and water (100 mL), cooled to −78° C. and lyophilized to provide C32 as a pink solid. Yield: 0.155 g, 0.217 mmol, 9%. LCMS m/z 715.2 (M+1). $^1$H NMR (500 MHz, DMSO-$d_6$) δ 1.42 (s, 3H), 1.43 (s, 3H), 3.27 (m, 2H), 3.37 (dd, J=6.1, 3.1 Hz, 1H), 3.65 (m, 1H), 3.70 (m, 1H), 3.95 (m, 2H), 4.91 (m, 1H), 6.81 (s, 1H), 7.37 (s, 1H), 8.01 (s, 1H), 9.04 (d, J=8.3 Hz, 1H). HPLC analysis: Hewlett Packard 1100; Column: Waters® Symmetry C8, 5μM, 4.6×50 mm; Flow rate 1.2 mL/min; Solvent A: 0.1% aqueous formic acid; Solvent B: 0.1% formic acid in acetonitrile; Gradient: 5% to 100% B over 6 minutes; Injection volume: 15 uL; Detection: 254 nm; Retention time: 3.46 min.

B. Preparation of compound 5. Compound 5 was prepared according to the general procedure for the synthesis of 4 in Example 4, except that C32 was used in place of C27, to afford 5 as a pink solid. Yield: 0.155 g, 0.204 mmol, 97%. LCMS m/z 715.2 (M+1). $^1$H NMR (500 MHz, D$_2$O) δ 1.40 (s, 3H), 1.42 (s, 3H), 3.49 (dd, half of an ABX pattern, J=12.2, 4.9 Hz, 1H), 3.57 (dd, half of an ABX pattern J=12.2, 3.7 Hz, 1H), 3.74 (m, 1H), 3.88 (m, 1H), 3.98 (m, 3H), 5.03 (m, 1H), 6.90 (s, 1H), 7.02 (s, 1H), 7.80 (s, 1H). HPLC analysis: Hewlett Packard 1100; Column: Waters® Symmetry C8, 5 μM, 4.6×50 mm; Flow rate 1.2 mL/min; Solvent A: 0.1% aqueous formic acid; Solvent B: 0.1% formic acid in acetonitrile; Gradient: 5% to 100% B over 6 minutes; Injection volume: 15 uL; Detection: 254 nm; Retention time: 3.44 min.

Example 6

Preparation of 2-({[(1Z)-1-(2-amino-1,3-thiazol-4-yl)-2-({(3S)-1-[({3-(5-hydroxy-4-oxo-1,4-dihydropyridin-2-yl)-4-[(2R)-2-hydroxypropyl]-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid, disodium salt (6)

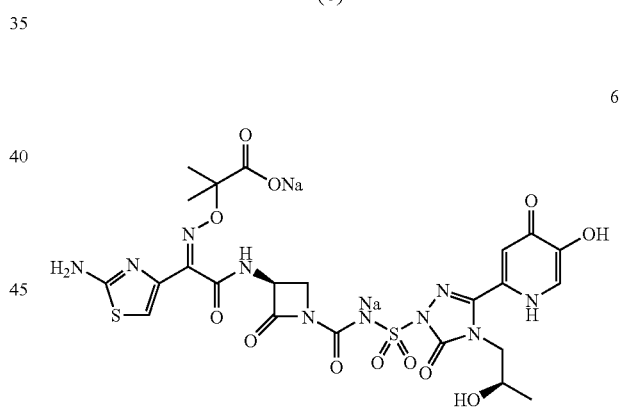

6

Compound 6 was prepared by the procedures depicted in Schemes 17 to 19 and described in detail below.

Scheme 17

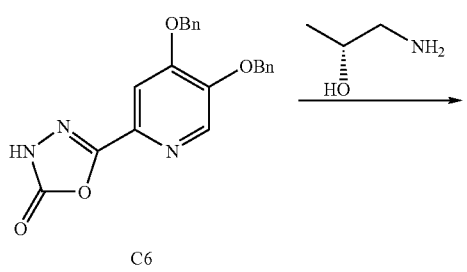

C6

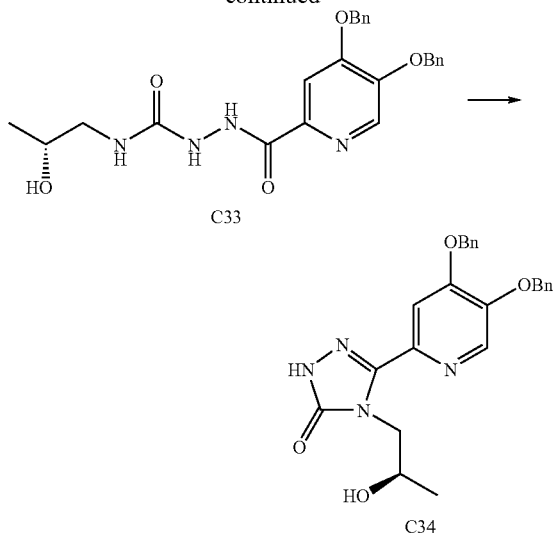

Step 1. Preparation of 5-[4,5-bis(benzyloxy)pyridin-2-yl]-4-[(2R)-2-hydroxypropyl]-2,4-dihydro-3H-1,2,4-triazol-3-one (C34)

A. Preparation of 2-{[4,5-bis(benzyloxy)pyridin-2-yl]carbonyl}-N-[(2R)-2-hydroxypropyl]hydrazinecarboxamide (C33). Compound C33 was prepared according to the general procedure for the synthesis of C19 in Example 3, except that (2R)-1-aminopropan-2-ol was used in place of (2R)-3-aminopropane-1,2-diol, and the reaction was heated for 60 hours, to provide C33 as a white solid. Yield: 4.54 g, 10.1 mmol, 84%. LCMS m/z 451.2 (M+1). $^1$H NMR (400 MHz, DMSO-$d_6$) δ 1.00 (d, J=6.2 Hz, 3H), 2.91 (m, 1H), 3.01 (m, 1H), 3.61 (m, 1H), 4.64 (d, J=4.7 Hz, 1H), 5.33 (br s, 4H), 6.28 (dd, J=5.8 Hz, 1H), 7.31-7.49 (m, 10H), 7.69 (s, 1H), 7.93 (br s, 1H), 8.28 (s, 1H), 9.97 (br s, 1H).

B. Preparation of C34. Compound C34 was prepared according to the general procedure for the synthesis of C20 in Example 3, except that C33 was used in place of C19. After the solid was filtered, it was recrystallized from methanol (250 mL) to obtain two combined crops of C34. Yield: 36.5 g, 84.4 mmol, 74%. LCMS m/z 433.6 (M+1). $^1$H NMR (400 MHz, DMSO-$d_6$) δ 0.98 (d, J=6.3 Hz, 3H), 3.81 (m, 1H), 3.96 (dd, half of an ABX pattern, J=13.3, 5.3 Hz, 1H), 4.05 (dd, half of an ABX pattern, J=13.3, 7.4 Hz, 1H), 4.84 (d, J=5.1 Hz, 1H), 5.28 (s, 2H), 5.31 (s, 2H), 7.32-7.49 (m, 10H), 7.59 (s, 1H), 8.32 (s, 1H), 11.96 (br s, 1H).

Scheme 18

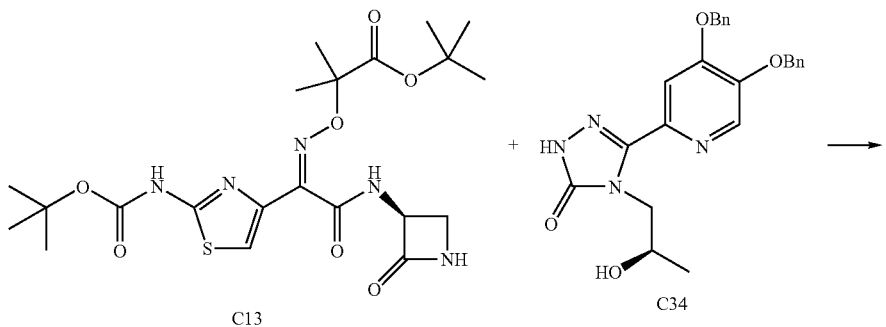

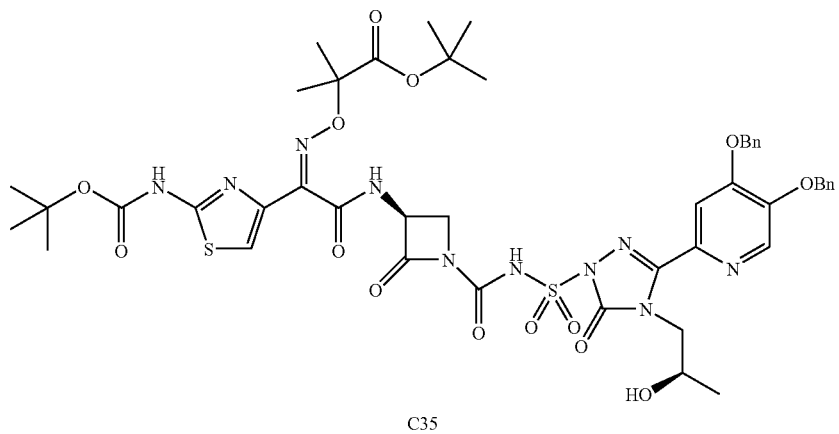

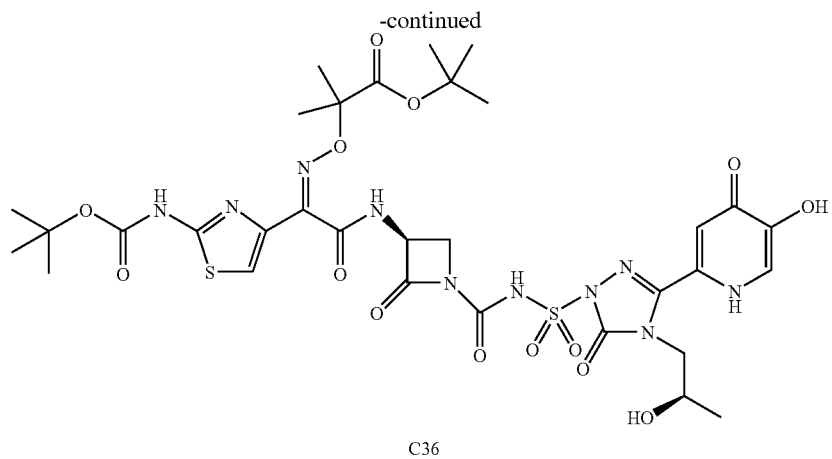

Step 2. Preparation of tert-butyl 2-({[(1Z)-1-{2-[(tert-butoxycarbonyl)amino]-1,3-thiazol-4-yl}-2-({(3S)-1-[({3-(5-hydroxy-4-oxo-1,4-dihydropyridin-2-yl)-4-[(2R)-2-hydroxypropyl]-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoate (C36)

A. Preparation of tert-butyl 2-({[(1Z)-2-({(3S)-1-[({3-[4,5-bis(benzyloxy)pyridin-2-yl]-4-[(2R)-2-hydroxypropyl]-5-oxo-4,5-dihydro-1H-1,2,4-triazol-1-yl}sulfonyl)carbamoyl]-2-oxoazetidin-3-yl}amino)-1-{2-[(tert-butoxycarbonyl)amino]-1,3-thiazol-4-yl}-2-oxoethylidene]amino}oxy)-2-methylpropanoate (C35). A suspension of C34 (1 g, 2.31 mmol) in 1,1,1,3,3,3,-hexamethyldisilazane (2.54 mL, 11.6 mmol) was treated with trimethylsilyl chloride (0.002 mL, 0.012 mmol), and the mixture was heated at 140° C. for 2 hours. The yellow solution was then cooled to room temperature and concentrated in vacuo to afford a yellow gum. In a separate flask, a suspension of C13 (1.15 g, 2.31 mmol) in dichloromethane (2 mL) under nitrogen at 0° C. was treated with carbonylsulfamoyl chloride (0.211 mL, 2.31 mmol) and stirred for 1.5 hours at 0° C. The mixture became a homogenous solution. The material derived from C34 was treated with dichloromethane (2 mL), and the resulting yellow solution was cooled to −40° C. and stirred under nitrogen. The ice-cooled C13-containing reaction mixture was transferred into this solution via syringe. The mixture was stirred at −40° C. for 30 minutes, warmed to room temperature over 1 hour and stirred for 2 hour at room temperature. The mixture was quenched by the addition of methanol (5 mL), the solvent was removed in vacuo, and the crude material was purified by silica gel chromatography (Gradient: 0-3% methanol in ethyl acetate) to afford C35 as a solid. Yield: 1.42 g, 1.37 mmol, 59%. LCMS m/z 1035.7 (M+1) $^1$H NMR (400 MHz, DMSO-$d_6$) δ 0.95 (d, J=5.8 Hz, 3H), 1.33-1.43 (m, 15H), 1.46 (s, 9H), 3.40 (m, 1H), 3.71 (m, 1H), 3.77 (m, 1H), 3.95 (m, 1H), 4.06 (m, 1H), 4.84 (d, J=5.1 Hz, 1H), 5.29 (s, 2H), 5.31 (s, 2H), 7.25 (s, 1H), 7.31-7.51 (m, 10H), 7.60 (s, 1H), 8.36 (s, 1H), 9.02 (d, J=8.3 Hz, 1H), 11.85 (br s, 1H).

B. Preparation of C36. Compound C36 was prepared according to the general procedure for the synthesis of C22 in Example 3, except that C35 was used in place of C21, and the reaction was hydrogenated at 25 psi for 1.5 hour, to afford C36 as a red solid. Yield: 3.84 g, 4.49 mmol, 88%. LCMS m/z 853.0 (M−1).

Scheme 19

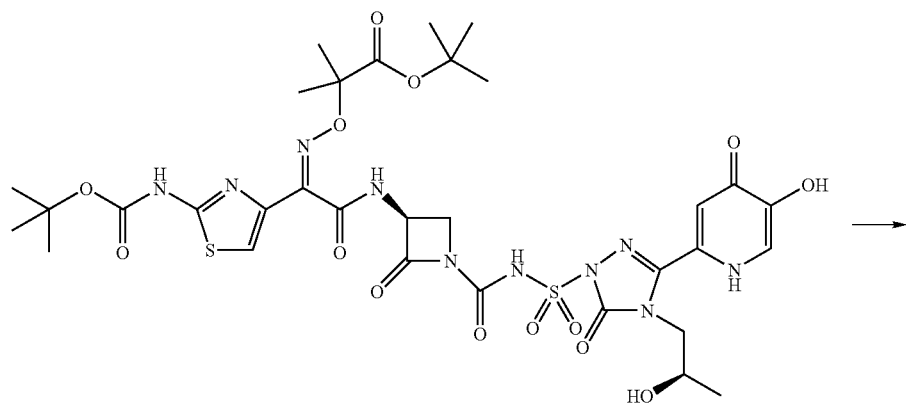

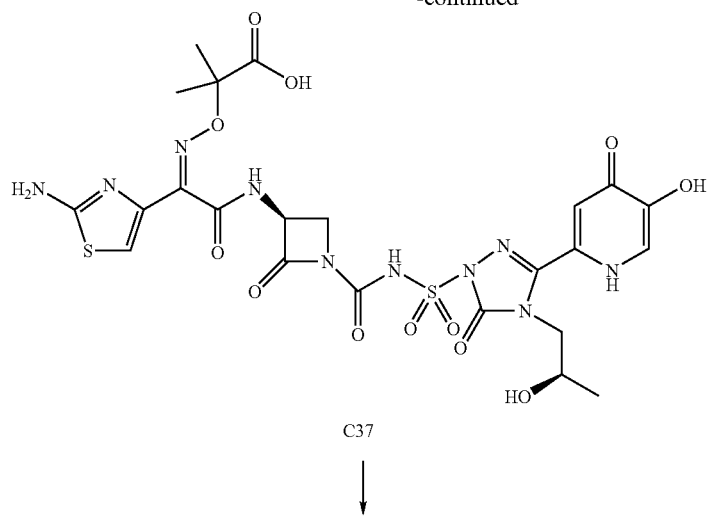

C37

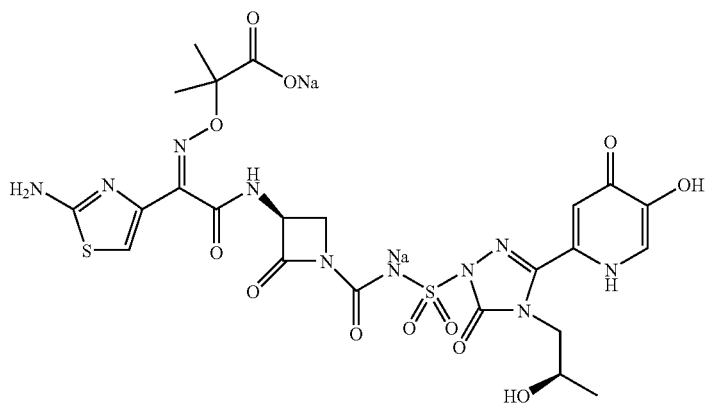

6

Step 3. Preparation of 2-({[(1Z)-1-(2-amino-1,3-thiazol-4-yl)-2-({(3S)-1-[({3-(5-hydroxy-4-oxo-1,4-dihydropyridin-2-yl)-4-[(2R)-2-hydroxypropyl]-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid, disodium salt (6)

A. Preparation of 2-({[(1Z)-1-(2-amino-1,3-thiazol-4-yl)-2-({(3S)-1-[({3-(5-hydroxy-4-oxo-1,4-dihydropyridin-2-yl)-4-[(2R)-2-hydroxypropyl]-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid C37. Compound C37 was prepared according to the general procedure for the synthesis of 3 in Example 3, except that C36 was used in place of C22. The crude product was dissolved in dimethyl sulfoxide to a concentration of 100 mg/mL, filtered, and purified by preparative HPLC (column: Waters® Symmetry C8, 5 µm, 30×50 mm; Solvent A: 0.1% aqueous formic acid; Solvent B: 0.1% formic acid in acetonitrile; Gradient: 6% to 26% B). The fractions that pertained to the desired product were concentrated in vacuo to provide a solid, which was dissolved in a mixture of acetonitrile (10 mL) and water (100 mL), cooled to −78° C. and lyophilized to provide C37 as a pink solid. Yield: 0.130 g, 0.186 mmol, 15%. LCMS m/z 699.0 (M+1). $^1$H NMR (500 MHz, DMSO-$d_6$) δ 0.97 (d, J=6.1 Hz, 3H), 1.43 (s, 3H), 1.43 (s, 3H), 3.38 (dd, J=6.3, 3.2 Hz, 1H), 3.69 (dd, J=6.1, 6.1 Hz, 1H), 3.78 (m, 1H), 3.86 (m, 1H), 4.91 (m, 1H), 6.83 (s, 1H), 7.39 (s, 1H), 8.02 (s, 1H), 9.08 (d, J=8.3 Hz, 1H).

B. Preparation of 6. Compound 6 was prepared according to the general procedure for the synthesis of 4 in Example 4, except that C37 was used in place of C27, and that the starting material C37 was dissolved in methanol (20 mL), sonicated for five minutes, and concentrated in vacuo. This process was repeated three times before the reaction was run. Compound 6 was obtained as a pink solid. Yield: 0.150 g, 0.202 mmol, 96%. LCMS m/z 699.8 (M+1). $^1$H NMR (400 MHz, DMSO-$d_6$) δ 0.95 (d, J=5.3 Hz, 3H), 1.41 (s, 3H), 1.49 (s, 3H), 3.30-3.40 (m, 1H, assumed; obscured by water peak) 3.82 (m, 1H), 3.97 (m, 3H), 5.11 (m, 1H), 6.78 (s, 1H), 7.19 (br s, 1H), 7.36 (s, 1H), 7.88 (s, 1H).

Example 7

Preparation of 2-({[(1Z)-1-(2-amino-1,3-thiazol-4-yl)-2-({(3S)-1-[({(3-(5-hydroxy-4-oxo-1,4-dihydro-pyridin-2-yl)-4-[(2S)-2-hydroxypropyl]-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid, disodium salt (7)

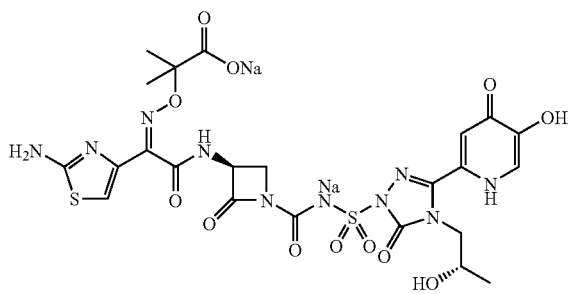

Compound 7 was prepared by the procedures depicted in Schemes 20 to 22 and described in detail below.

Scheme 20

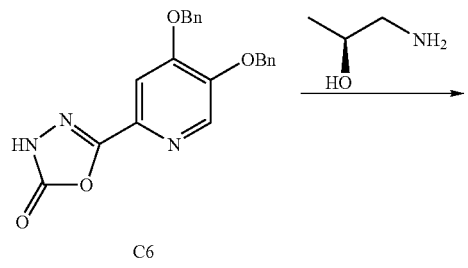

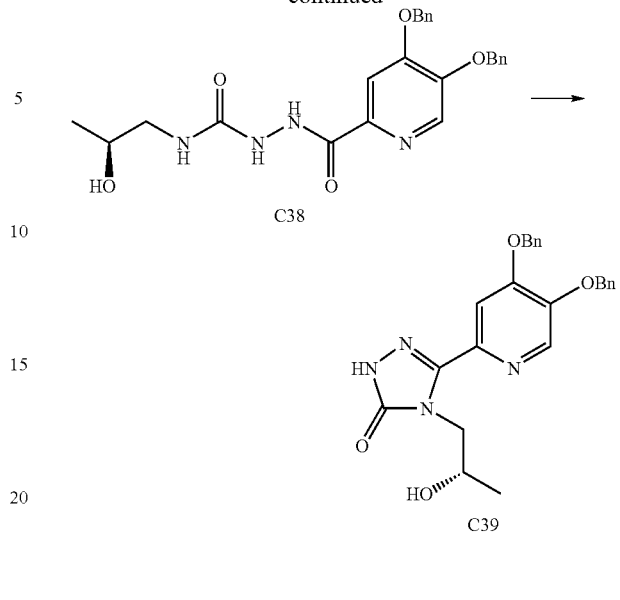

Step 1. Preparation of 5-[4,5-bis(benzyloxy)pyridin-2-yl]-4-[(2S)-2-hydroxypropyl]-2,4-dihydro-3H-1,2,4-triazol-3-one (C39)

A. Preparation of 2-{[4,5-bis(benzyloxy)pyridin-2-yl]carbonyl}-N-[(2S)-2-hydroxypropyl]hydrazinecarboxamide (C38). Compound C38 was prepared according to the general procedure for the synthesis of C19 in Example 3, except that (2S)-1-aminopropan-2-ol was used in place of (2R)-3-aminopropane-1,2-diol, and the reaction was heated for 12 hours, to provide C38 as a white solid. Yield: 12.56 g, 27.88 mmol, 87%. LCMS m/z 451.6 (M+1). $^1$H NMR (400 MHz, DMSO-$d_6$) δ 1.00 (d, J=6.2 Hz, 3H), 2.91 (m, 1H), 3.01 (m, 1H), 3.61 (m, 1H), 4.65 (d, J=4.7 Hz, 1H), 5.33 (s, 4H), 6.28 (dd, J=5.8 Hz, 1H), 7.31-7.49 (m, 10H), 7.69 (s, 1H), 7.93 (br s, 1H), 8.28 (s, 1H), 9.99 (br s, 1H).

B. Preparation of C39. Compound C39 was prepared according to the general procedure for the synthesis of C20 in Example 3, except that C38 was used in place of C19 and the reaction was heated for 18 hours to afford C39 as a red solid. Yield: 4.25 g, 9.82 mmol, 95%. LCMS m/z 433.3 (M+1). $^1$H NMR (400 MHz, DMSO-$d_6$) δ 0.98 (d, J=6.3 Hz, 3H), 3.85 (m, 1H), 3.98 (m, 1H), 4.07 (m, 1H), 5.28 (s, 2H), 5.31 (s, 2H), 7.31-7.49 (m, 11H), 7.60 (s, 1H), 8.32 (s, 1H).

Scheme 21

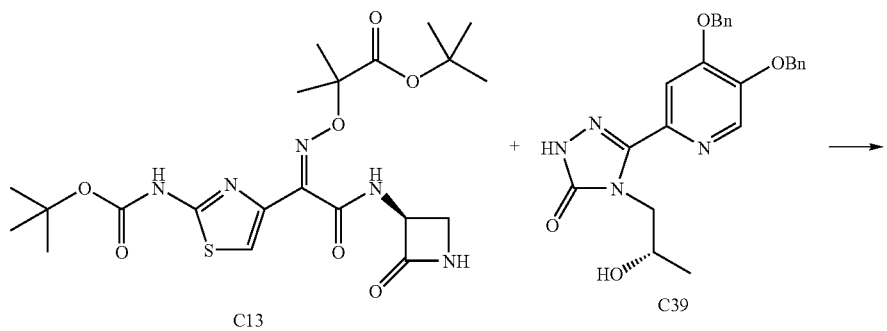

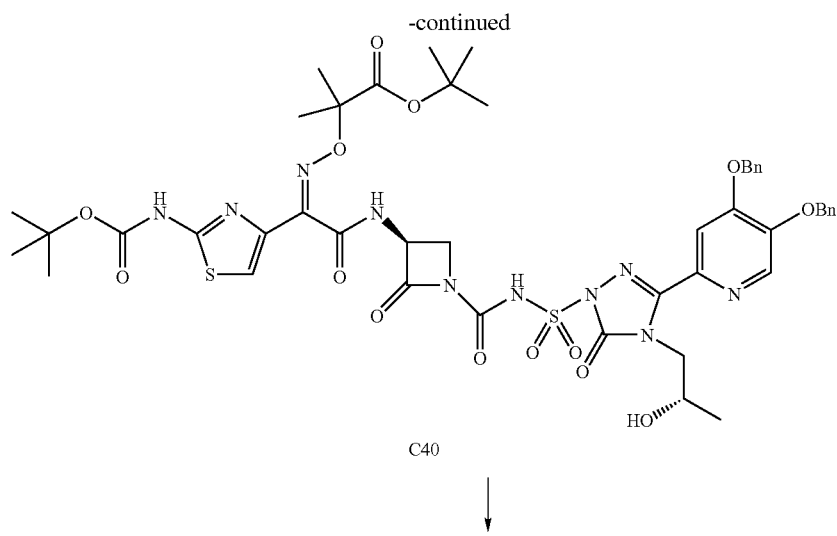

C40

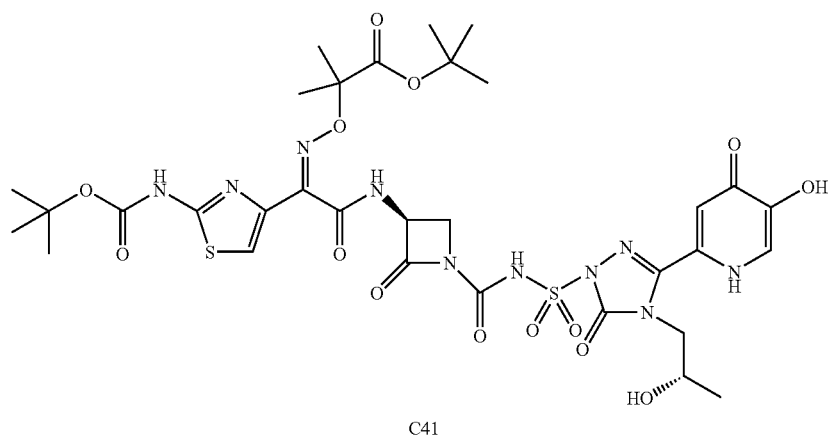

C41

Step 2. Preparation of tert-butyl 2-({[(1Z)-1-{2-[(tert-butoxycarbonyl)amino]-1,3-thiazol-4-yl}-2-({(3S)-1-[({3-(5-hydroxy-4-oxo-1,4-dihydropyridin-2-yl)-4-[(2S)-2-hydroxypropyl]-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoate (C41)

A. Preparation of tert-butyl 2-({[(1Z)-2-({(3S)-1-[({3-[4,5-bis(benzyloxy)pyridin-2-yl]-4-[(2S)-2-hydroxypropyl]-5-oxo-4,5-dihydro-1H-1,2,4-triazol-1-yl}sulfonyl)carbamoyl]-2-oxoazetidin-3-yl}amino)-1-{2-[(tert-butoxycarbonyl)amino]-1,3-thiazol-4-yl}-2-oxoethylidene]amino}oxy)-2-methylpropanoate (C40). Compound C40 was prepared according to the general procedure for the synthesis of C35 in Example 6, except that C39 was used in place of C34. After the mixture was quenched by the addition of methanol (3 mL), the solvent was removed in vacuo and the crude material was purified by silica gel chromatography (Gradient: 0-3% methanol in ethyl acetate) to afford C40' as a yellow solid. Yield: 0.71 g, 0.685 mmol, 44%. LCMS m/z 1035.6 (M+1). $^1$H NMR (400 MHz, DMSO-$d_6$) δ 0.96 (d, J=6.2 Hz, 3H), 1.38-1.47 (m, assumed 24H), 3.40 (dd, J=6.2, 3.1 Hz, 1H), 3.71 (m, 1H), 3.78 (m, 1H), 3.95 (m, 1H), 4.07 (m, 1H), 4.83 (d, J=5.5 Hz, 1H), 4.91 (m, 1H), 5.29 (s, 2H), 5.31 (s, 2H), 7.25 (s, 1H), 7.31-7.51 (m, 10H), 7.60 (s, 1H), 8.36 (s, 1H), 9.01 (d, J=8.6 Hz, 1H), 11.82 (br s, 1H).

B. Preparation of C41. Compound C41 was prepared according to the general procedure for the synthesis of C22 in Example 3, except that C40 was used in place of C21, and the reaction was hydrogenated at 30 psi for 1 hour. Additionally, in this case filtration was carried out through a 1 cm bed of iron-free Celite® (Celite® was pre-washed with 1N aqueous hydrochloric acid, then with deionized water, then with acetone, and then dried). Compound C41 was obtained as a red solid. Yield: 0.630 g, 0.7 mmol, 100%. LCMS m/z 855.1 (M−1).

Scheme 22

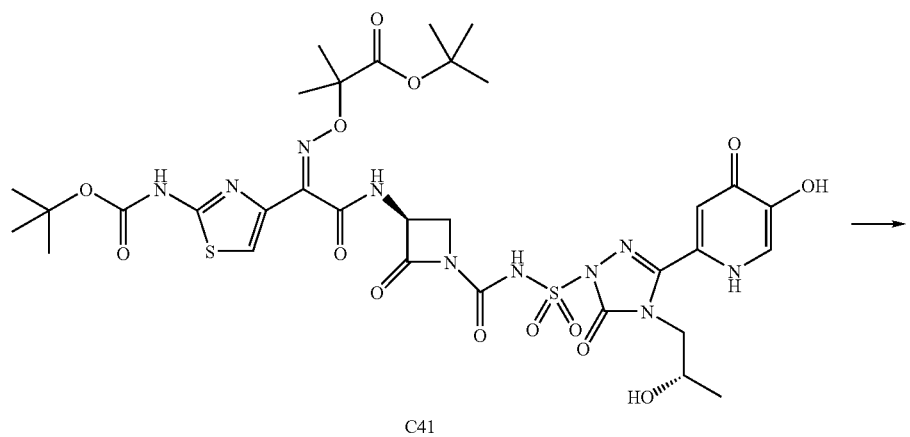

C41

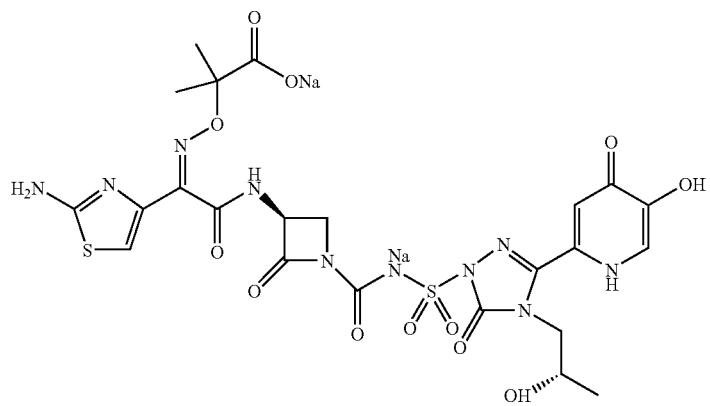

7

Step 3. Preparation 2-({[(1Z)-1-(2-amino-1,3-thiazol-4-yl)-2-({(3S)-1[({3-(5-hydroxy-4-oxo-1,4-dihydropyridin-2-yl)-4-[(2S)-2-hydroxypropyl]-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid, disodium salt (7). A solution of C41 (0.630 g, 0.76 mmol) in dichloromethane (0.5 mL) was cooled to 0° C. and treated with trifluoroacetic acid (3.4 mL). The mixture was warmed to room temperature and stirred for 18 hours; the reaction mixture was then slowly added drop-wise to a stirring solution of methyl-tert-butyl ether (10 mL) and heptane (20 mL). The resulting solid was filtered, dried in vacuo, dissolved into dimethyl sulfoxide (1 mL) and purified via reverse phase chromatography (RediSep® RF $C_{18}$ Column, 65 g; Solvent A: 0.1% aqueous formic acid; Solvent B: 0.1% formic acid in acetonitrile; Gradient: 5% to 25%B). The fractions that pertained to the desired product were concentrated in vacuo to provide a solid. The solid was sonicated in methanol and the solvent was removed (this was carried out 4 times) to give free form material as a white solid. Yield: 0.103 g, 0.147 mmol, 19%. LCMS m/z 699.0 (M+1). $^1$H NMR (500 MHz, DMSO-$d_6$) δ 0.95 (d, J=6.1 Hz, 3H), 1.43 (s, 3H), 1.44 (s, 3H), 3.38 (dd, J=6.5, 3.3 Hz, 1H), 3.70 (dd, J=6.1, 6.1 Hz, 1H), 3.77 (m, 1H), 3.86 (m, 2H), 4.91 (m, 1H), 6.82 (s, 1H), 7.38 (s, 1H), 8.02 (s, 1H), 9.06 (d, J=8.8 Hz, 1H). Combined batches of free form (0.676 g, 0.92 mmol) were placed round bottom flask with 10 mL of deionized water. The suspension was cooled to 0° C. in an ice bath and to this mixture added (dropwise) a solution of 0.154 g of sodium bicarbonate in 1.0 mL of water. The suspension was stirred until all the solids were dissolved. The solution was then frozen and lyophilized affording 0.680 g of compound 7 as a light pink solid. LCMS m/z 699.6 (M+1). $^1$H NMR (500 MHz, $D_2$O-$d_6$) δ 1.01(d, J=8.5 Hz, 3H), 1.32 (d, J=6.0 Hz, 6H), 3.61 -3.70 (m, 2.5H), 3.77 (dd, ½ABX, J=18.5 Hz, 4.0 Hz, 0.5H), 3.88 (t, J=8.0 Hz, 1H), 4.90 (dd,J=7.5 Hz, 4.5 Hz, 1H), 6.80 (s, 1H), 6.93 (s, 1H), 7.71 (s, 1H).

Example 8
Preparation of 2-({[(1Z)-1-(2-amino-1,3-thiazol-4-yl)-2-({(3S)-1-[({4-1[1,5-dimethyl-1H-pyrazol-3-yl)methyl]-3-(5-hydroxy-4-oxo-1,4-dihydropyridin-2-yl)-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid (8)
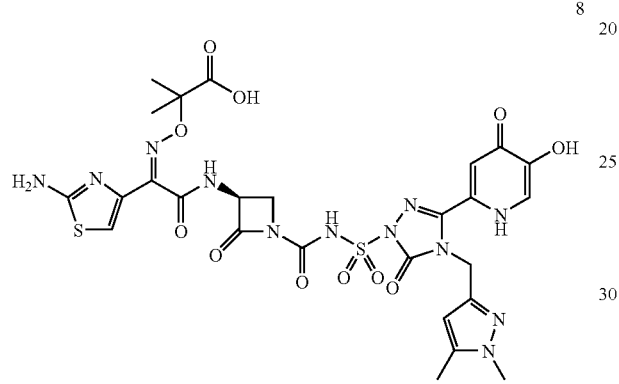
Compound 8 was prepared by the procedures depicted in scheme 23 and outlined in detail below.
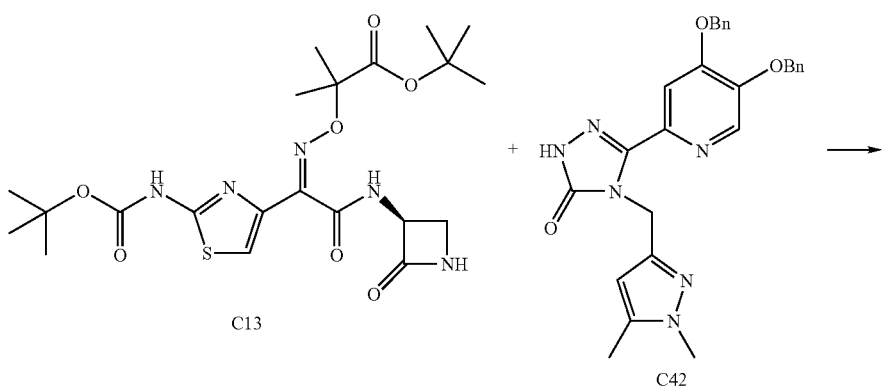

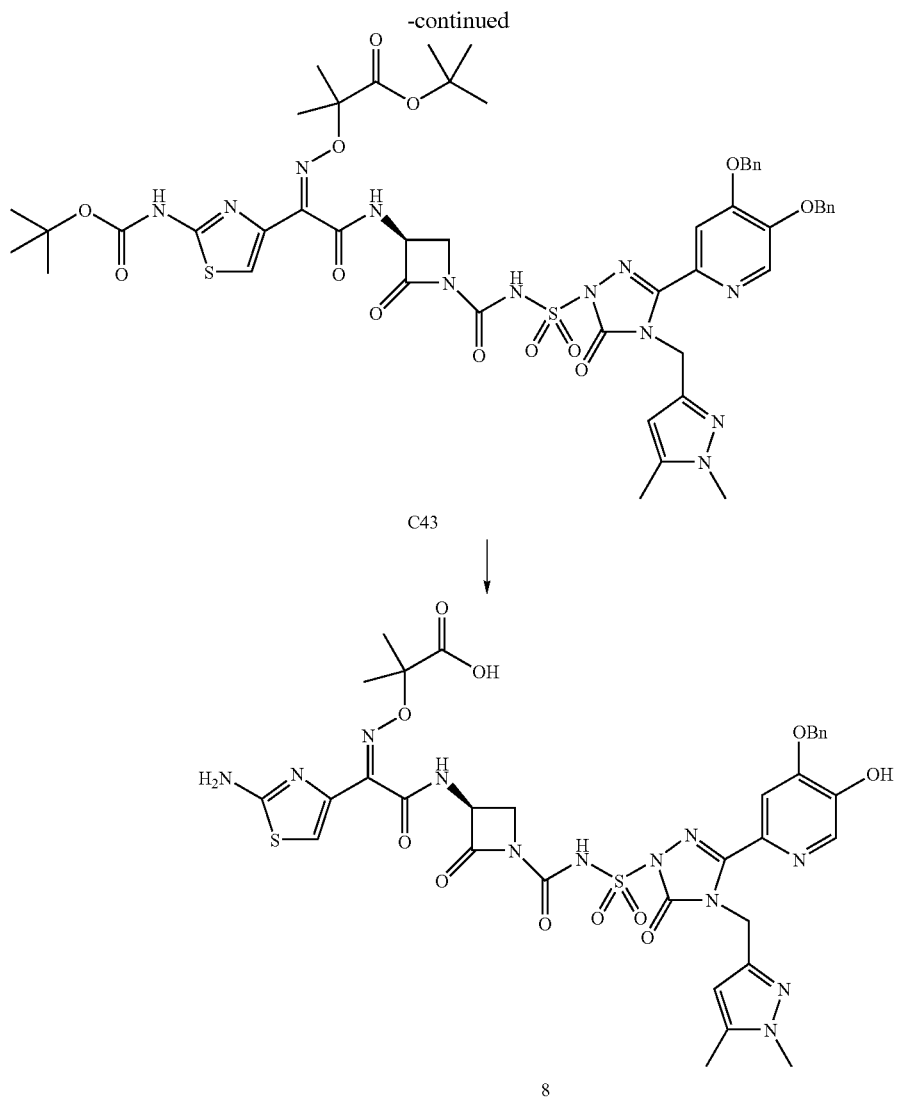

A. Preparation of C43 (Coupling Method 2). Compound C42 was prepared in an analogous manner to that described for the preparation of C8 in Example 1 affording 0.67 g (0.72 mmol) of triazalone C42 as a white solid. LCMS m/z 483.4 (M+1). A suspension of C42 (0.100 g, 0.207 mmol) in hexamethyldisilazide (0.227 mL, 1.04 mmol) under nitrogen at 23° C. was treated with trimethylsilylchloride (one drop, 0.13 uL, 0.001 mmol). The mixture was heated at 140° C. for 2 hours; upon heating the reaction became a clear brown solution. The mixture was cooled to room temperature and held under high vacuum for 1 hour producing a brown glass-like material. Separately, a suspension of C13 (0.103 g, 0.207 mmol) in dichloromethane (0.1 mL) under nitrogen at 0° C. was treated with chlorosulfonylisocyanate (0.019 mL, 0.207 mmol) and stirred until the mixture became homogeneous (approximately 5 minutes). The solution was stirred for 1.5 hours at 0° C. The silylated triazolinone (0.207 mmol) was treated with DCM (0.2 mL), the brown solution was cooled to −40° C. and stirred under nitrogen. The prepared sulfamoyl chloride solution (0.1 mL, 0.207 mmol) was then transferred via syringe to the complex prepared from C42 and the mixture stirred at −40° C. for 30 minutes, warmed to room temperature over 1 hour and stirred for 2 hours at room temperature. The mixture was quenched by the addition of methanol (0.5 mL), the solvent was removed in vacuo and the crude material purified by column chromatography (silica-gel, 5% methanol in dichloromethane) to give 0.050 g (22%) of C43. LCMS m/z 1085.1 (M+1). $^1$H NMR (400 MHz, DMSO-d$_6$) δ 1.34-1.48 (m, 24H), 2.06-2.10 (m, 1H), 2.25-2.28 (m, 1H), 3.40-3.44 (m, 1H), 3.55 (s, 1H), 4.92 (br. s, 1H), 5.20-5.63 (m, 4H), 5.56-5.63 (m, 1H), 7.25 (d, J=4.9 Hz, 1H), 7.28-7.50 (m, 10H), 7.58 (s, 1H), 8.33 (s, 1H), 9.01 (br. s, 2H).

B. Preparation of 2-({[(1Z)-1-(2-amino-1,3-thiazol-4-yl)-2-({(3S)-1-[({4-[(1,5-dimethyl-1H-pyrazol-3-yl)methyl]-3-(5-hydroxy-4-oxo-1,4-dihydropyridin-2-yl)-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid (8). Compound C43 was deprotected and HPLC purified in an analogous manner to that described for compound 1 in Example 1 affording 0.015 g (9%) of compound 8 as a pink solid. LCMS m/z 748.9 (M+1). $^1$H NMR (500 MHz, DMSO-d$_6$) δ 1.41 (s, 3H), 1.41 (s, 3H), 2.39 (s, 1H), 3.55 (s, 3H), 3.67 (m, 1H), 3.91 (dd, J=6.3, 6.3 Hz, 1H), 5.05 (m, 1H), 5.58 (s, 2H), 6.73 (s, 1H), 7.26 (s, 1H), 7.34 (br s, 1H), 7.80 (s, 1H), 9.10 (d, J=8.0 Hz, 1H), 11.85 (s, 1H).

Additional Examples 9-30 are shown below in Table A and were prepared analogously to the Examples above using either cyclization method 1 (described in Example 1, step 3B) or cyclization method 2 (described in Example 4, step 1B), in combination with either coupling method 1 (described in Example 1, step 6A) or coupling method 2 (described in Example 4, step 1B).

TABLE A

| Ex. No. | Cyclization Method, Coupling Method | Structure | IUPAC Name | $^1$H NMR 400 MHz, DMSO-$d_6$ (unless otherwise indicated); Observed MS Ion (m/z) |
|---|---|---|---|---|
| 9 | 1, 1 | 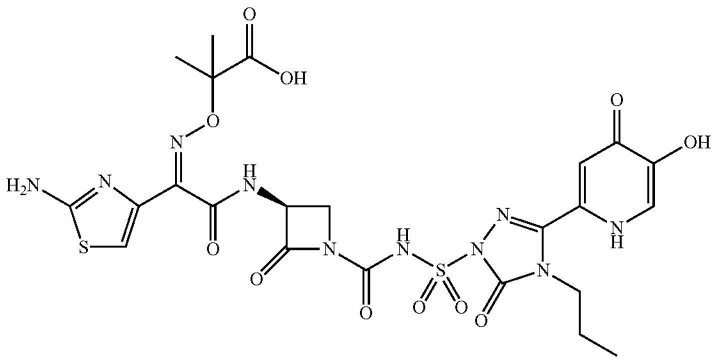 | 2-{[(1Z)-1-(2-amino-1,3-thiazol-4-yl)-2-{[(3S)-1-({[3-(5-hydroxy-4-oxo-1,4-dihydropyridin-2-yl)-5-oxo-4-propyl-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid | 0.76 (t, J = 7.5 Hz, 3H), 1.42 (br s, 6H), 1.51 (m, 2H), 3.37 (dd, J = 6.2, 3.3 Hz, 1H), 3.69 (dd, J = 6.6, 6.6 Hz, 1H), 3.94 (t, J = 7.5 Hz, 2H), 4.91 (m, 1H), 6.81 (s, 1H), 7.34 (s, 1H), 8.01 (s, 1H), 9.06 (d, J = 7.9 Hz, 1H) |
| 10 | 1, 1 | | 2-{[(1Z)-1-(2-amino-1,3-thiazol-4-yl)-2-{[(3S)-1-({[4-(2,3-dihydroxypropyl)-3-(5-hydroxy-4-oxo-1,4-dihydropyridin-2-yl)-5-oxo-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid | 1.43 (s, 6H), 3.28 (m, 2H), 3.38 (m, 1H), 3.65 (m, 1H), 3.70 (dd, J = 6.2, 6.2 Hz, 1H), 3.93 (m, 2H), 4.91 (m, 1H), 6.82 (s, 1H), 7.38 (s, 1H), 8.02 (s, 1H), 9.06 (d, J = 7.9 Hz, 1H); 715.5 (M + 1) | ns TABLE A-continued

| Ex. No. | Cyclization Method, Coupling Method | Structure | IUPAC Name | 1H NMR 400 MHz, DMSO-d6 (unless otherwise indicated); Observed MS Ion (m/z) |
|---|---|---|---|---|
| 11 | 1, 1 | 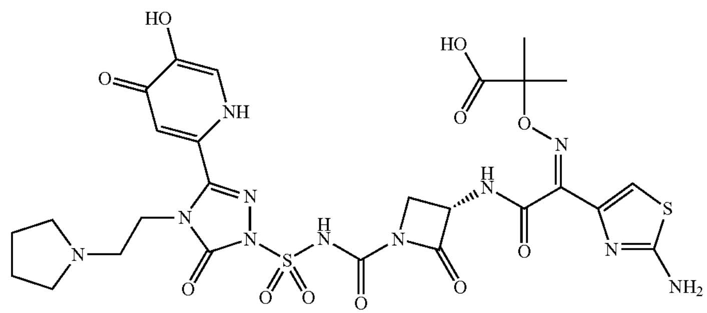 | 2-{[(1Z)-1-(2-amino-1,3-thiazol-4-yl)-2-{[(3S)-1-({[3-(5-hydroxy-4-oxo-1,4-dihydropyridin-2-yl)-5-oxo-4-(2-pyrrolidin-1-ylethyl)-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid | Selected peaks: 1.38 (s, 3H), 1.39 (s, 3H), 1.78 (m, 2H), 1.89 (m, 2H), 3.15-3.36 (m, assumed 7H, obscured by water peak), 3.58 (m, 2H), 4.13 (m, 1H), 5.68 (br s, 1H), 6.06 (br s, 1H), 6.86 (s, 1H), 7.30 (br s, 2H), 8.85 (br s, 1H); 736.1 (M − 1) |
| 12 | 1, 1 | 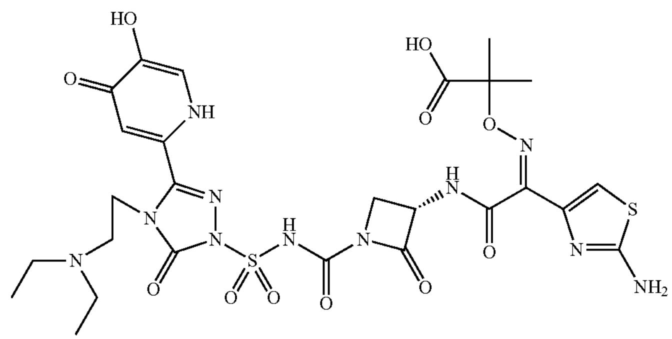 | 2-{[(1Z)-1-(2-amino-1,3-thiazol-4-yl)-2-{[(3S)-1-({[4-[2-(diethylamino)ethyl]-3-(5-hydroxy-4-oxo-1,4-dihydropyridin-2-yl)-5-oxo-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid | (MeOD) Selected peaks: 1.27-1.35 (m, assumed 6H), 1.55 (s, 3H), 1.56 (s, 3H), 3.39 (m, 4H), 3.59 (dd, J = 6.6, 6.6 Hz, 1H), 3.66 (t, J = 5.4 Hz, 2H), 3.92 (dd, J = 6.6, 6.6 Hz, 1H), 4.51 (t, J = 5.4 Hz, 2H), 5.34 (m, 1H), 6.89 (s, 1H), 7.50 (s, 1H), 8.05 (s, 1H); 740.5 (M + 1) |
| 13 | 2, 1 | 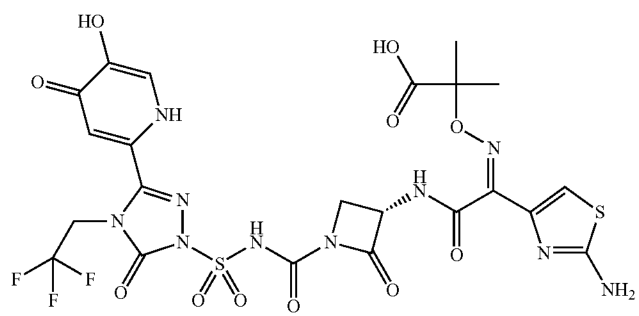 | 2-{[(1Z)-1-(2-amino-1,3-thiazol-4-yl)-2-{[(3S)-1-({[3-(5-hydroxy-4-oxo-1,4-dihydropyridin-2-yl)-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid | 1.41 (s, 3H), 1.41 (s, 3H), 3.36 (dd, J = 6.2, 3.2 Hz, 1H), 3.69 (dd, J = 6.2, 6.2 Hz, 1H), 4.91 (m, 1H), 5.11 (m, 2H), 6.76 (m, 1H), 7.37 (s, 1H), 8.00 (s, 1H), 9.01 (d, J = 8.3 Hz, 1H); 723.1 (M + 1) |

TABLE A-continued

| Ex. No. | Cyclization Method, Coupling Method | Structure | IUPAC Name | $^1$H NMR 400 MHz, DMSO-$d_6$ (unless otherwise indicated); Observed MS Ion (m/z) |
|---|---|---|---|---|
| 14 | 2, 2 | 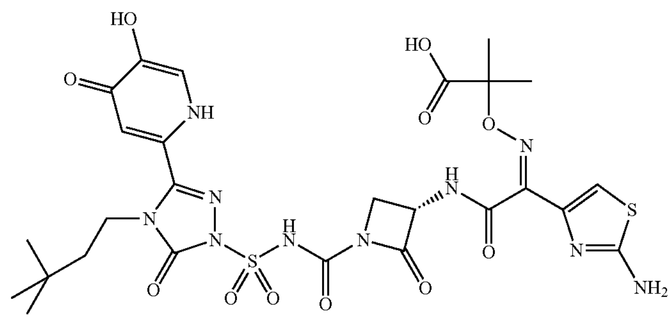 | 2-{[(1Z)-1-(2-amino-1,3-thiazol-4-yl)-2-{[(3S)-1-({[4-(3,3-dimethylbutyl)-3-(5-hydroxy-4-oxo-1,4-dihydropyridin-2-yl)-5-oxo-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid | 0.89 (s, 9H), 1.40 (m, 2H), 1.43 (s, 3H), 1.43 (s, 3H), 3.37 (dd, J = 6.4, 3.1 Hz, 1H), 3.70 (dd, J = 6.4, 6.4 Hz, 1H), 4.01 (m, 2H), 4.92 (m, 1H), 6.80 (s, 1H), 7.99 (s, 1H), 9.05 (br d, J = 8.8 Hz, 1H); 725.2 (M + 1) |
| 15 | 1, 2 | 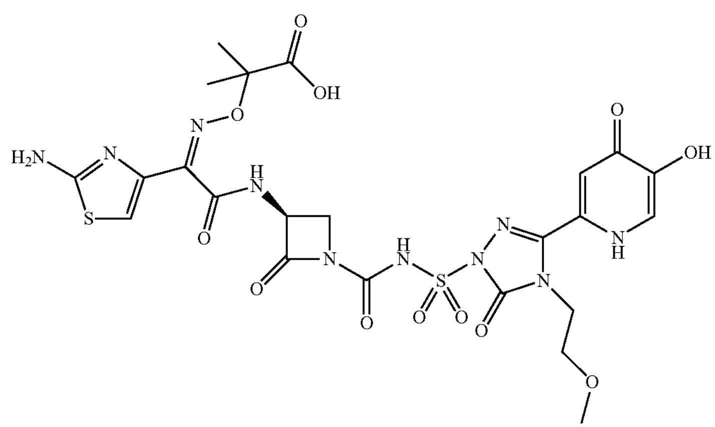 | 2-{[(1Z)-1-(2-amino-1,3-thiazol-4-yl)-2-{[(3S)-1-({[3-(5-hydroxy-4-oxo-1,4-dihydropyridin-2-yl)-4-(2-methoxyethyl)-5-oxo-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid, disodium salt | 1.42 (s, 3H), 1.50 (s, 3H), 3.16 (s, 3H), 3.32 (HOD, obscures region), 3.48 (m, 2H), 3.78 (dd, J = 6.3, 6.3 Hz, 1H), 4.18 (m, 2H), 5.14 (m, 1H), 6.79 (s, 1H), 7.19 (br s, 2H), 7.40 (s, 1H), 7.88 (s, 1H); 699.2 (M + 1) |

TABLE A-continued

| Ex. No. | Cyclization Method, Coupling Method | Structure | IUPAC Name | 1H NMR 400 MHz, DMSO-d6 (unless otherwise indicated); Observed MS Ion (m/z) |
|---|---|---|---|---|
| 16 | 1, 2 | 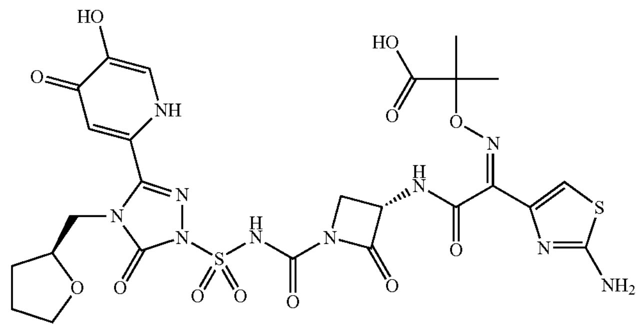 | 2-{[(1Z)-1-(2-amino-1,3-thiazol-4-yl)-2-({(3S)-1-[({3-(5-hydroxy-4-oxo-1,4-dihydropyridin-2-yl)-5-oxo-4-[(2S)-tetrahydrofuran-2-ylmethyl]-4,5-dihydro-1H-1,2,4-triazol-1-yl]sulfonyl}carbamoyl]-2-oxoazetidin-3-yl}amino)-2-oxoethylidene]amino}oxy)-2-methylpropanoic acid | Selected peaks: 1.42 (br s, 6H), 3.38 (m, 1 H), 3.48 (t, J = 5.1, 2 H), 3.70 (dd, J = 6.2, 6.2, 2H), 3.97 (m, 2H), 4.13 (m, 1 H), 4.92 (m, 1H), 6.82 (s, 1H), 7.35 (s, 1 H), 8.01 (s, 1H), 9.04 (d, J = 8.0 Hz, 1H); 725.2 (M + 1) |
| 17 | 1, 2 | 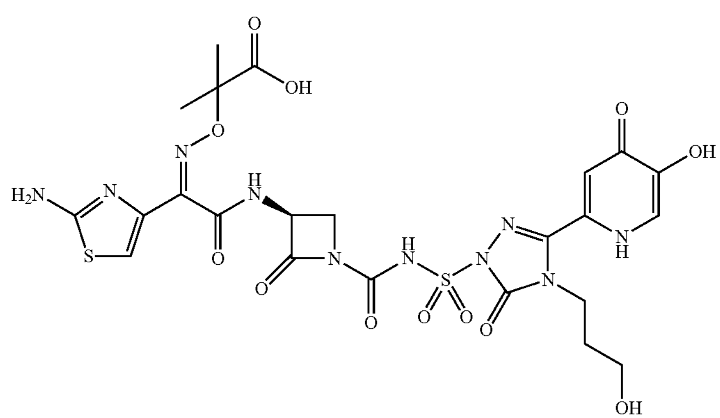 | 2-{[(1Z)-1-(2-amino-1,3-thiazol-4-yl)-2-{[(3S)-1-({[3-(5-hydroxy-4-oxo-1,4-dihydropyridin-2-yl)-4-(3-hydroxypropyl)-5-oxo-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid | (500 MHz) 1.44 (s, 3H), 1.44 (s, 3H), 1.67 (m, 2H), 3.35 (t, J = 6.3 Hz, 2H), 3.38 (dd, J = 6.5, 3.3 Hz, 1H), 3.70 (dd, J = 6.4, 6.4 Hz, 1H), 4.01 (m, 2H), 4.92 (m, 1H), 6.84 (s, 1H), 7.35 (s, 1H), 8.01 (s, 1H), 9.07 (d, J = 8.5 Hz, 1H); 699.0 (M + 1) |

TABLE A-continued

| Ex. No. | Cyclization Method, Coupling Method | Structure | IUPAC Name | 1H NMR 400 MHz, DMSO-d6 (unless otherwise indicated); Observed MS Ion (m/z) |
|---|---|---|---|---|
| 18 | 1, 2 | 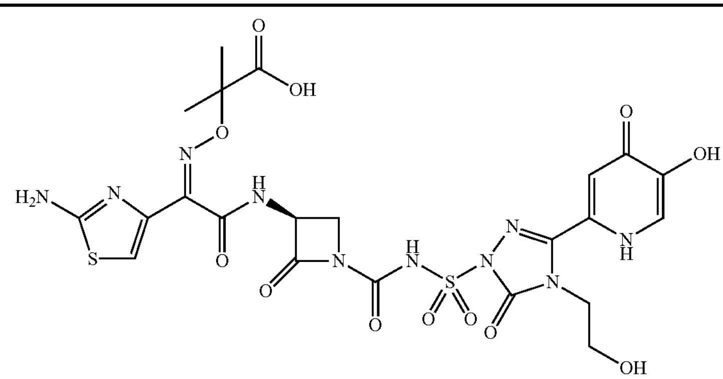 | 2-{[(1Z)-1-(2-amino-1,3-thiazol-4-yl)-2-[(3S)-1-({[4-(2-hydroxyethyl)-3-(5-hydroxy-4-oxo-1,4-dihydropyridin-2-yl)-5-oxo-4,5-dihydro-1H-1,2,4-triazol-1-yl]sulfonyl}carbamoyl)-2-oxoazetidin-3-yl]amino]-2-oxoethylidene]amino}oxy)-2-methylpropanoic acid | (500 MHz) 1.40 (s, 3H), 1.41 (s, 3H), 3.29-3.38 (m, assumed 4H, obscured by water peak), 3.47 (m, 1H), 4.08 (dd, J = 6.3, 6.3, 1H), 4.89 (m, 1H), 6.54 (s, 1H), 6.71 (s, 1H), 7.31 (m, 2H), 8.00 (s, 1H), 9.06 (m, 1H); 685.0 (M + 1) |
| 19 | 1, 2 | 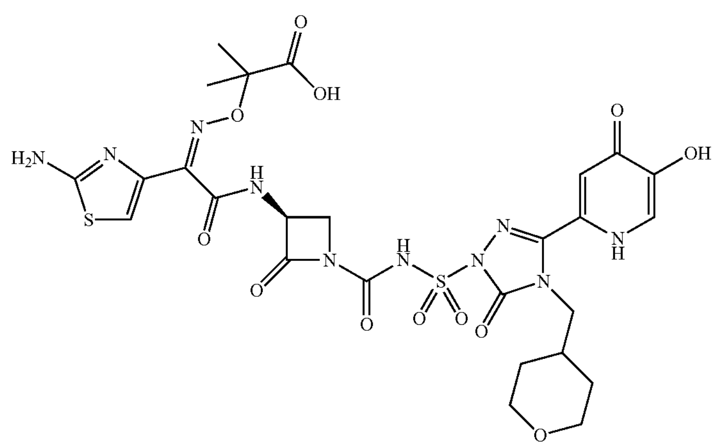 | 2-{[(1Z)-1-(2-amino-1,3-thiazol-4-yl)-2-{[(3S)-1-({[3-(5-hydroxy-4-oxo-1,4-dihydropyridin-2-yl)-5-oxo-4-(tetrahydro-2H-pyran-4-ylmethyl)-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid | 1.11 (m, 2H), 1.39 (m, 2H), 1.42 (s, 3H), 1.43 (s, 3H), 1.84 (m, 1H), 3.15 (m, 2H), 3.36 (dd, J = 6.4, 3.5 Hz, 1H), 3.68 (dd, J = 6.2, 6.2 Hz, 1H), 3.75 (br d, J = 10 Hz, 2H), 3.97 (d, J = 6.8 Hz, 2H), 4.91 (m, 1H), 6.79 (s, 1H), 7.36 (s, 1H), 8.01 (s, 1H), 9.02 (d, J = 8.4 Hz, 1H); 739.2 (M + 1) |

TABLE A-continued

| Ex. No. | Cyclization Method, Coupling Method | Structure | IUPAC Name | 1H NMR 400 MHz, DMSO-d6 (unless otherwise indicated); Observed MS Ion (m/z) |
|---|---|---|---|---|
| 20 | 1, 2 | 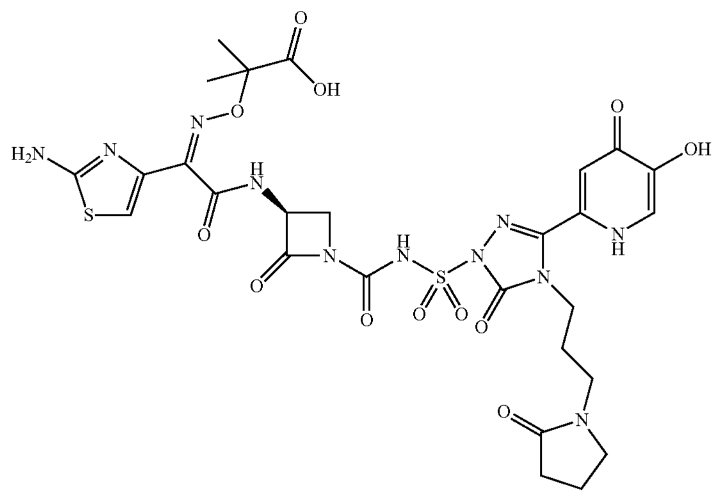 | 2-{[(1Z)-1-(2-amino-1,3-thiazol-4-yl)-2-({(3S)-1-[({3-(5-hydroxy-4-oxo-1,4-dihydropyridin-2-yl)-5-oxo-4-[3-(2-oxopyrrolidin-1-yl)propyl]-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid | 1.44 (s, 6H), 1.74 (m, 2H), 1.91 (m, 2H), 2.19 (t, J = 8.1 Hz, 2H), 3.17 (t, J = 6.9 Hz, 2H), 3.31 (t, J = 6.9 Hz, 2H), 3.37 (dd, J = 6.6, 3.3 Hz, 1H), 3.70 (dd, J = 6.2, 6.2 Hz, 1H), 3.94 (m, 2H), 4.92 (m, 1H), 6.84 (s, 1H), 7.36 (s, 1H), 8.01 (s, 1H), 9.05 (d, J = 8.8 Hz, 1H); 766.2 (M + 1) |
| 21 | 1, 2 | 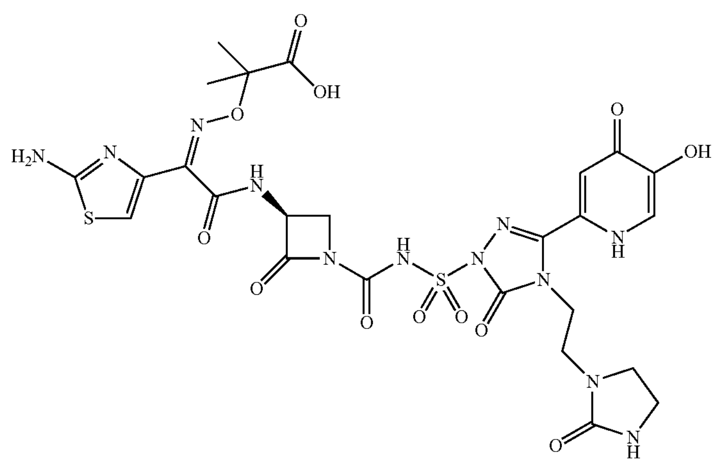 | 2-{[(1Z)-1-(2-amino-1,3-thiazol-4-yl)-2-({(3S)-1-[({3-(5-hydroxy-4-oxo-1,4-dihydropyridin-2-yl)-5-oxo-4-[2-(2-oxoimidazolidin-1-yl)ethyl]-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid | Product peaks: 1.41 (s, 3H), 1.41 (s, 3H), 3.29-3.56 (m, assumed 4H, obscured by water peak), 3.77 (m, 1H), 3.82 (m, 2H), 4.15 (t, J = 6.6, 2H), 5.00 (m, 1H), 6.72 (s, 1H), 7.32 (s, 1H), 8.01 (s, 1H), 8.99 (d, J = 8.2 Hz, 1H); 753.2 (M + 1) |

TABLE A-continued

| Ex. No. | Cyclization Method, Coupling Method | Structure | IUPAC Name | ¹H NMR 400 MHz, DMSO-d₆ (unless otherwise indicated); Observed MS Ion (m/z) |
|---|---|---|---|---|
| 22 | 1, 2 | 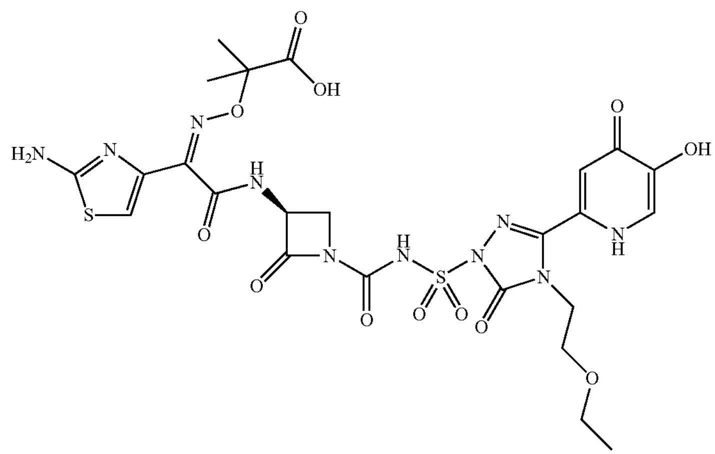 | 2-{[(1Z)-1-(2-amino-1,3-thiazol-4-yl)-2-[[(3S)-1-({[4-(2-ethoxyethyl)-3-(5-hydroxy-4-oxo-1,4-dihydropyridin-2-yl)-5-oxo-4,5-dihydro-1H-1,2,4-triazol-1-yl]sulfonyl}carbamoyl)-2-oxoazetidin-3-yl]amino]-2-oxoethylidene]amino}oxy)-2-methylpropanoic acid | 0.93 (t, J = 6.9 Hz, 3H), 1.44 (s, 6H), 3.31 (q, J = 6.9 Hz, 2H), 3.37 (m, 1H), 3.46 (t, J = 5.7 Hz, 2H), 3.70 (dd, J = 5.9, 5.9 Hz, 1H), 4.14 (m, 2H), 4.92 (m, 1H), 6.82 (s, 1H), 7.36 (s, 1H), 8.01 (s, 1H), 9.04 (d, J = 8.6 Hz, 1H); 713.2 (M+1) |
| 23 | 1, 2 | 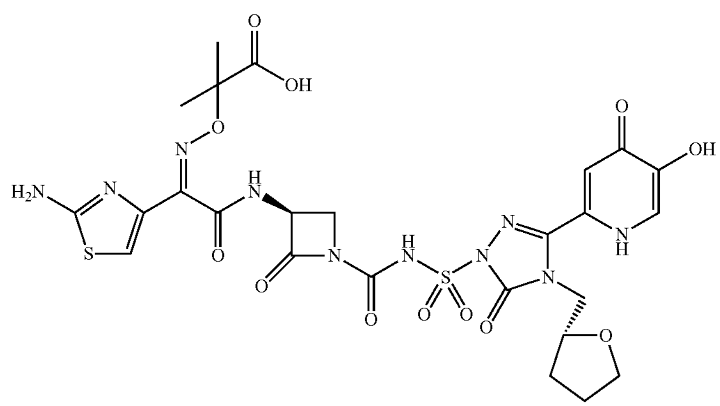 | 2-{[(1Z)-1-(2-amino-1,3-thiazol-4-yl)-2-({(3S)-1-[({3-(5-hydroxy-4-oxo-1,4-dihydropyridin-2-yl)-4-[(2R)-tetrahydrofuran-2-ylmethyl]-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid | Selected peaks: 1.42 (br s, 6H), 3.36 (m, 1 H), 3.48 (t, J = 5.3 Hz, 2 H), 3.70 (dd, J = 6.2, 6.2 Hz, 1H), 3.97 (m, 2H), 4.14 (m, 1 H), 4.91 (m, 1 H), 6.78 (br s, 1 H), 7.34 (s, 1H), 8.01 (s, 1H), 9.02 (d, J = 7.8 Hz, 1H) |

TABLE A-continued

| Ex. No. | Cyclization Method, Coupling Method | Structure | IUPAC Name | 1H NMR 400 MHz, DMSO-d6 (unless otherwise indicated); Observed MS Ion (m/z) |
|---|---|---|---|---|
| 24 | 2, 2 | 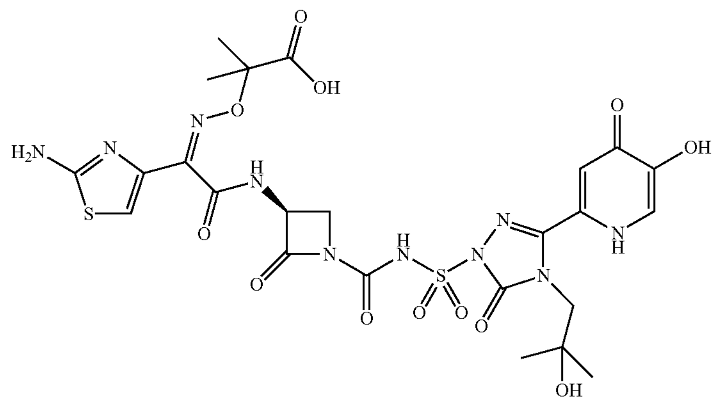 | 2-{[(1Z)-1-(2-amino-1,3-thiazol-4-yl)-2-{[(3S)-1-({[4-(2-hydroxy-2-methylpropyl)-3-(5-hydroxy-4-oxo-1,4-dihydropyridin-2-yl)-5-oxo-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid | 1.00 (s, 6H), 1.42 (s, 6H), 3.37 (m, 1H), 3.69 (dd, J = 6.2, 6.2 Hz, 1H), 3.96 (s, 2H), 4.91 (m, 1H), 6.75 (s, 1H), 7.31 (s, 1H), 7.98 (s, 1H), 8.98 (d, J = 8.6 Hz, 1H); 713.2 (M + 1) |
| 25 | 1, 2 | 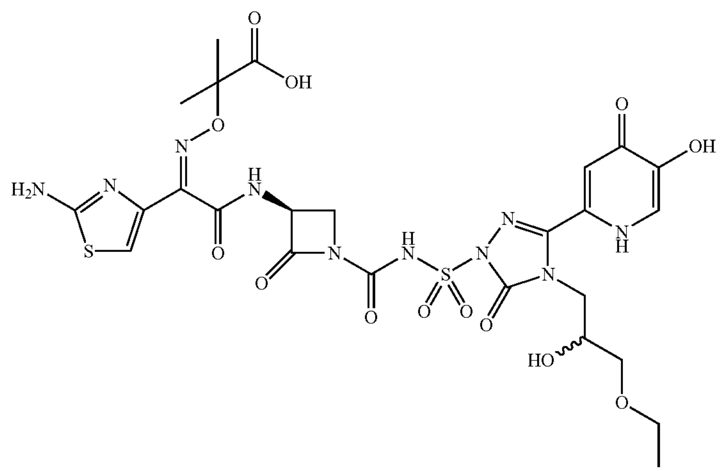 | 2-{[(1Z)-1-(2-amino-1,3-thiazol-4-yl)-2-{[(3S)-1-({[4-(3-ethoxy-2-hydroxypropyl)-3-(5-hydroxy-4-oxo-1,4-dihydropyridin-2-yl)-5-oxo-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid | 1.05 (t, J = 6.9 Hz, 3H), 1.43 (s, 3H), 1.43 (s, 3H), 3.25 (d, J = 5.3 Hz, 2H), 3.36 (q, J = 6.9 Hz, 2H), 3.39 (m, 1H), 3.70 (dd, J = 6.2, 6.2 Hz, 1H), 3.79 (m, 1H), 3.97 (m, 2H), 4.91 (m, 1H), 6.80 (s, 1H), 7.36 (s, 1H), 8.00 (s, 1H), 9.03 (d, J = 8.4 Hz, 1H); 743.2 (M + 1) |

TABLE A-continued

| Ex. No. | Cyclization Method, Coupling Method | Structure | IUPAC Name | 1H NMR 400 MHz, DMSO-d6 (unless otherwise indicated); Observed MS Ion (m/z) |
|---|---|---|---|---|
| 26 | 1, 2 | 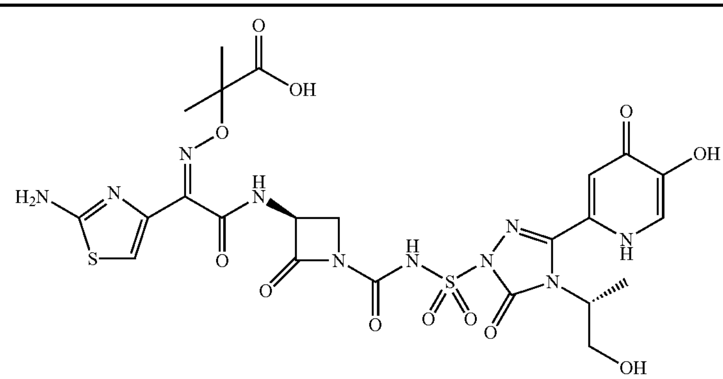 | 2-{[{(1Z)-1-(2-amino-1,3-thiazol-4-yl)-2-{(3S)-1-[{4-[(1R)-1-methylethyl]-3-(5-hydroxy-4-oxo-1,4-dihydropyridin-2-yl)-5-oxo-4,5-dihydro-1H-1,2,4-triazol-1-yl]sulfonyl}carbamoyl]-2-oxoazetidin-3-yl]amino}-2-oxoethylidene]amino}oxy)-2-methylpropanoic acid | (500 MHz) 1.35 (d, J = 6.8 Hz, 3H), 1.43 (s, 3H), 1.44 (s, 3H), 3.39 (dd, J = 6.3, 3.2 Hz, 1H), 3.50 (dd, J = 10.9, 5.5 Hz, 1H), 3.71 (dd, J = 6.3, 6.3 Hz, 1H), 3.82 (dd, J = 10.9, 8.9 Hz, 1H), 4.65 (m, 1H), 4.92 (m, 1H), 6.83 (s, 1H), 7.32 (s, 1H), 8.04 (s, 1H), 9.07 (d, J = 8.3 Hz, 1H); 699.0 (M + 1) |
| 27 | 1, 2 | 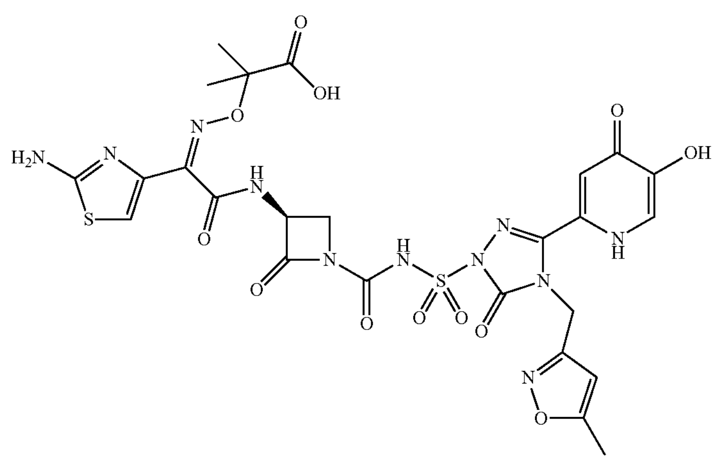 | 2-{[{(1Z)-1-(2-amino-1,3-thiazol-4-yl)-2-{(3S)-1-[{3-(5-hydroxy-4-oxo-1,4-dihydropyridin-2-yl)-4-[(5-methylisoxazol-3-yl)methyl]-5-oxo-4,5-dihydro-1H-1,2,4-triazol-1-yl]sulfonyl}carbamoyl]-2-oxoazetidin-3-yl]amino}-2-oxoethylidene]amino}oxy)-2-methylpropanoic acid | 1.42 (s, 6H), 2.30 (s, 3H), 3.38 (m, 1H), 3.42-3.74 (m, assume 1 H, obscured by water peak), 4.92 (m, 1H), 5.35 (s, 2H), 6.05 (s, 1H), 6.78 (s, 1H), 7.35 (s, 1H), 7.93 (s, 1H), 9.01 (d, J = 8.0 Hz, 1H); 736.1 (M + 1) |

TABLE A-continued

| Ex. No. | Cyclization Method, Coupling Method | Structure | IUPAC Name | $^1$H NMR 400 MHz, DMSO-$d_6$ (unless otherwise indicated); Observed MS Ion (m/z) |
|---|---|---|---|---|
| 28 | 2, 2 | 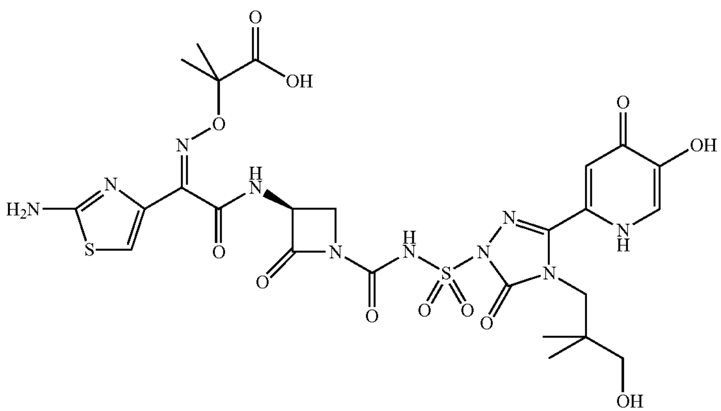 | 2-{[(1Z)-1-(2-amino-1,3-thiazol-4-yl)-2-{[(3S)-1-({[4-(3-hydroxy-2,2-dimethylpropyl)-3-(5-hydroxy-4-oxo-1,4-dihydropyridin-2-yl)-5-oxo-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid | 0.58 (s, 6H), 1.43 (s, 3H), 1.44 (s, 3H), 2.97 (s, 2H), 3.38 (dd, J = 6.3, 3.2 Hz, 1H), 3.70 (dd, J = 6.3, 6.3 Hz, 1H), 4.05 (s, 2H), 4.92 (m, 1H), 6.83 (s, 1H), 7.28 (s, 1H), 8.02 (s, 1H), 9.05 (d, J = 8.4 Hz, 1H); 726.9 (M + 1) |
| 29 | 1, 1 | 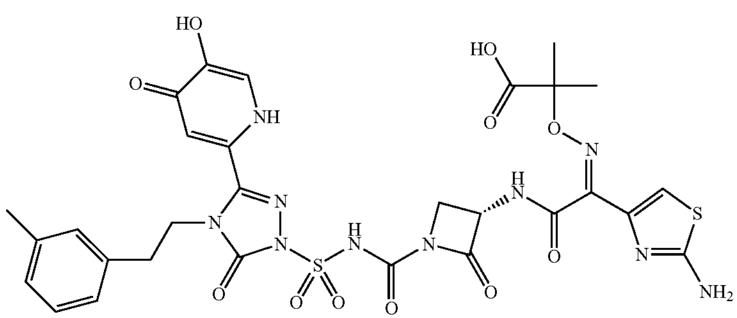 | 2-{[(1Z)-1-(2-amino-1,3-thiazol-4-yl)-2-({(3S)-1-[({3-(5-hydroxy-4-oxo-1,4-dihydropyridin-2-yl)-4-[2-(3-methylphenyl)ethyl]-5-oxo-4,5-dihydro-1H-1,2,4-triazol-1-yl}sulfonyl)carbamoyl]-2-oxoazetidin-3-yl}amino)-2-oxoethylidene]amino}oxy)-2-methylpropanoic acid | Selected peaks: 1.40 (s, 9H), 2.74 (t, J = 7.5 Hz, 2H), 4.13 (t, J = 8.1 Hz, 2H), 4.86-4.92 (m, 1H), 6.78-6.95 (m, 3H), 7.07 (t, J = 7.8 Hz, 1H), 7.12 (s, 1H), 8.01 (s, 1H), 9.05 (d, J = 7.8 Hz, 1H); 759.2 (M + 1) |

TABLE A-continued

| Ex. No. | Cyclization Method, Coupling Method | Structure | IUPAC Name | $^1$H NMR 400 MHz, DMSO-$d_6$ (unless otherwise indicated); Observed MS Ion (m/z) |
|---|---|---|---|---|
| 30 | 2, 2 | 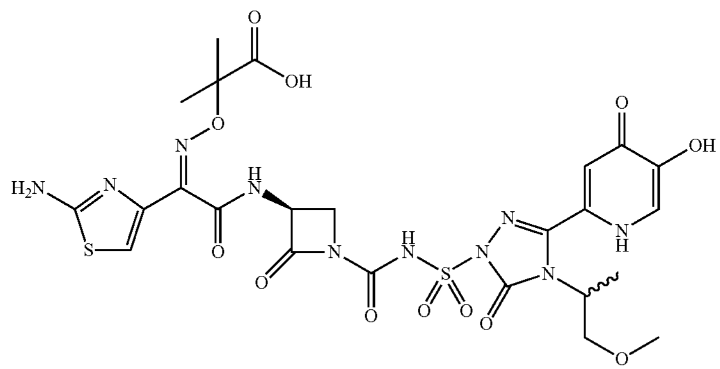 | 2-{[{(1Z)-1-(2-amino-1,3-thiazol-4-yl)-2-{[(3S)-1-({[3-(5-hydroxy-4-oxo-1,4-dihydropyridin-2-yl)-4-(2-methoxy-1-methylethyl)-5-oxo-4,5-dihydro-1H-1,2,4-triazol-1-yl]sulfonyl}carbamoyl)-2-oxoazetidin-3-yl]amino}-2-oxoethylidene]amino}oxy)-2-methylpropanoic acid | 1.36 (d, J = 6.5 Hz, 3H), 1.44 (d, J = 3.0 Hz, 6H), 3.38 (dd, J = 6.1 Hz, 3.0 Hz, 1H), 3.41 (dd, J = 10.0 Hz, 5.6 Hz, 1H), 3.71 (t, J = 6.5 Hz, 2H), 3.86 (t, J = 10.0 Hz, 2H), 4.90-4.95 (m, 1H), 5.03 (br. s, 1H), 6.83 (s, 1H), 7.29 (s, 1H), 8.03 (s, 1H), 9.08 (d, J = 8.7 Hz, 1H); 713.2 (M + 1) |

Biological Properties

In some embodiments, compounds of the invention exhibit a targeted and effective activity against bacteria. Compounds of the invention can therefore be used, e.g., for treating and/or preventing a variety of diseases caused by pathogenic bacteria in human beings and animals.

Table 1 below shows in vitro MIC data for specified strains of *Pseudomonas aeruginosa, Klebsiella pneumonia,* and *Acinetobacter baumanii*. Culture collection strain 1045-06 is resistant to several classes of known antimicrobial agents including carbapenems, aminoglycosides and fluoroquinolones, while strains 1000-02 and 3167 are resistant to cephalosporins. Strain PA0200 is a derivative of laboratory strain PAO1 that lacks a functional MexAB-oprM efflux pump. The compounds listed are highly active against all three of these screening strains demonstrating their broad activity against gram-negative bacterial pathogens.

TABLE 1

MIC of Examples 1-30

| Ex. No. | MIC *Pseudomonas aeruginosa* 1045-06 (mg/mL) | MIC *Klebsiella pneumoniae* 1000-02 (mg/mL) | MIC *Acinetobacter baumanii* 3167 (mg/mL) | MIC *Pseudomonas aeruginosa* PA0200 Mex AB-oprM KO (mg/mL) |
|---|---|---|---|---|
| 1 | N.T. | N.T. | N.T. | <0.0625 |
| 2 | N.T. | N.T. | N.T. | 0.188[1] |
| 3 | 0.5 | 0.5 | 0.5 | N.T. |
| 4 | 0.5 | 1 | 1 | N.T. |
| 5 | 0.25 | 0.5 | 0.5 | N.T. |
| 6 | 0.25 | 0.5 | 1 | N.T. |
| 7 | 0.25 | 0.25 | 1 | N.T. |
| 8 | 32 | 8 | >64.0 | N.T. |
| 9 | N.T. | N.T. | N.T. | <0.0625 |
| 10 | N.T. | N.T. | N.T. | 0.25[1] |
| 11 | N.T. | N.T. | N.T. | 16 |
| 12 | 2 | 2 | 16 | N.T. |
| 13 | 0.25 | 0.25 | 16 | N.T. |
| 14 | 0.5 | 0.06 | 2 | N.T. |
| 15 | 0.5 | 0.5 | 4 | N.T. |
| 16 | 0.5 | 0.5 | 2 | N.T. |
| 17 | 0.25 | 0.25 | 1 | N.T. |
| 18 | 2 | 1 | 8 | N.T. |
| 19 | 0.5 | 0.25 | 2 | N.T. |
| 20 | 0.5 | 0.25 | 2 | N.T. |
| 21 | 4 | 32 | >64.0 | N.T. |
| 22 | 0.5 | 0.5 | 2 | N.T. |
| 23 | 0.5 | 0.25 | 1 | N.T. |
| 24 | 0.5 | 0.25 | 2 | N.T. |
| 25 | 0.5 | 0.5 | 4 | N.T. |
| 26 | 0.5 | 0.125 | 2 | N.T. |
| 27 | 1 | 1 | 2 | N.T. |
| 28 | 2 | 0.5 | 4 | N.T. |
| 29 | 2 | 0.5 | >64 | N.T. |
| 30 | 0.5 | 8 | 1 | N.T. |

N.T. = Not Tested
[1] Value represents average 2 MIC determinations

Table 2 below shows several compounds of the invention compared to cefipime (a cephalosporin antibiotic indicated to treat bacterial infections caused from *Pseudomonas aeruginosa*), imipenem (a carbapenem antibiotic used to treat infections caused by *P. aeruginosa*) and Comparative Example A (example 23 in EP 0281289, published Sep. 7, 1988).

TABLE 2

In vitro and In Vivo Comparison Against *P. aeruginosa*

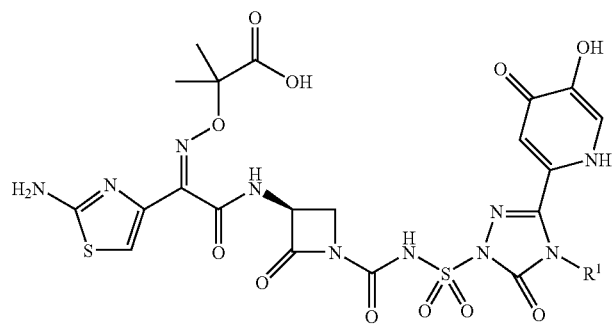

| Compound | Structure (R[1]) | Pa 1091-05 MIC (mg/mL) | RTI PD50 vs. Pa 1091-05 (mg/kg) (95% confidence interval) | Pa MIC90[2] |
|---|---|---|---|---|
| Cefepime | — | 2 | 22 | 64 |
| Imipenem | — | 0.5 | 1.04 | >64 |
| Comparative Example A | —CH₃ | 0.5 | >150[1] | 1 |
| Example 15 | 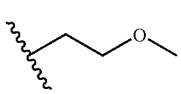 | 0.5 | >70.8 | 1 |

TABLE 2-continued

In vitro and In Vivo Comparison Against *P. aeruginosa*

| Compound | Structure (R¹) | Pa 1091-05 MIC (mg/mL) | RTI PD$_{50}$ vs. Pa 1091-05 (mg/kg) (95% confidence interval) | Pa MIC90[2] |
|---|---|---|---|---|
| Example 6 | (S)-2-hydroxypropyl (methyl branch) | 0.125 | 32.7 (23.7-42.0) | 1 |
| Example 7 | (R)-2-hydroxypropyl | 0.125 | 15.7 (8.45-22.96) | 1 |
| Example 3 | 2,3-dihydroxypropyl | 0.125 | 20.6 (8.7-32.52) | 1 |
| Example 5 | 2,3-dihydroxypropyl (epimer) | 0.125 | 18.6 (8.94-28.29) | 1 |
| Example 4 | -CH$_2$C(O)NH$_2$ | 0.125 | 25.0 (24.8-25.2) | 1 |

[1]Data are from a previous experiment
[2]91 clinical isolate

Table 2 shows the results for compounds of the invention which were evaluated for efficacy in the murine respiratory tract infection model against *P. aeruginosa* 1091-05. For this model, C3H/HeN mice were immunosuppressed with cyclophosphamide given orally at 150 mg/kg and 100 mg/kg on days −4 and −1 relative to challenge, respectively. Mice were anesthetized with isoflurane (5% in oxygen) and the bacterial inoculum was given to each mouse via intranasal instillation in a 40 μL volume (~2.8×10³ cfu per mouse). Mice were dosed with compound administered via subcutaneous injection beginning at four hours post-challenge, and continuing for two days of BID therapy. Lethalities were followed over ten days and the 50% protective doses (PD$_{50}$s) were determined. include interpretative comment on The known monocarbam prototype Comparative Example A (example 23b in EP 0281289, published Sep. 7, 1988) typically has a PD$_{50}$ of ≧100 mg/kg in this model. However, the exemplified monocarbams of the present invention were evaluated in this model and many demonstrated better efficacy than Comparative Example A, for example, Example 4 (25.0 mg/kg), Example 6 (32.7 mg/kg), Example 5 (18.6 mg/kg), Example 3 (20.6 mg/kg), and Example 7 (15.7 mg/kg).

PD$_{50}$ is a measure of the ability of a compound to protect mice from a lethal infection. Hence, a lower value in this study is indicative of improved efficacy. Since the 95% confidence intervals (the range that predicts where the actual value will lie with 95% confidence) calculated for the compounds Example 3, Example 6, Example 4, Example 7 and Example 5 do not overlap with the PD$_{50}$ value determined for Comparative Example A, it can be concluded that these compounds are significantly more efficacious relative to Comparative Example A.

This result was unexpected given the similar MICs against the pathogen used (*P. aeruginosa* 1091-05). Importantly, performance in these pre-clinical in vivo models is predictive of outcomes of clinical efficacy against these types of infections.

The invention claimed is:

1. A compound of formula (I),

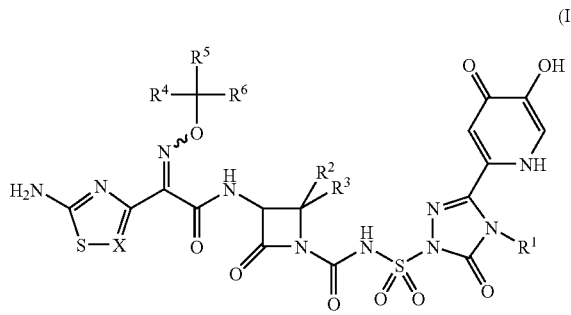

or pharmaceutically acceptable salt thereof; wherein
$R^1$ is $(C_1-C_6)$alkyl substituted with 1 to 3 substituents selected from the group consisting of halo, hydroxy, $(C_1-C_6)$alkoxy, —$NR^7R^8$, —$C(=O)NR^7R^8$, and a 3 to 7 membered heterocycle, wherein $R^7$ and $R^8$ are independently hydrogen or $(C_1-C_6)$alkyl, wherein said heterocycle contains 1 to 3 heteroatoms independently selected from O, N, or S;
$R^2$ is hydrogen or methyl;
$R^3$ is hydrogen or methyl;
$R^4$ is hydrogen, deuterium, or methyl optionally substituted with 1 to 3 substituents independently selected from F or Cl;
$R^5$ is hydrogen, deuterium or methyl optionally substituted with 1 to 3 substituents independently selected from F or Cl;
$R^6$ is H or —C(=O)OH; and
X is C(H), C(F), C(Cl), or N.

2. The compound of claim 1 having the formula (IA):

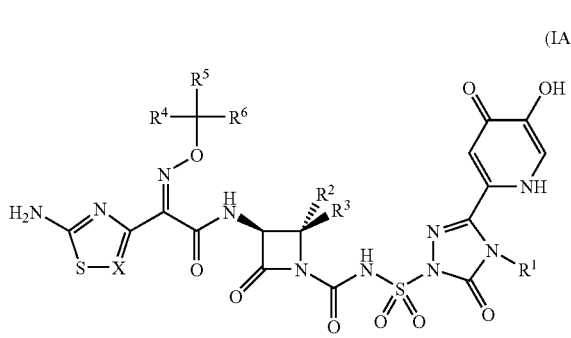

or pharmaceutically acceptable salt thereof.

3. The compound of claim 2, or pharmaceutically acceptable salt thereof, wherein $R^4$ is methyl optionally substituted with 1 to 3 substituents selected from F or Cl.

4. The compound of claim 2, or pharmaceutically acceptable salt thereof, wherein $R^4$ is hydrogen.

5. The compound of claim 4, or pharmaceutically acceptable salt thereof, wherein $R^5$ is methyl optionally substituted with 1 to 3 substituents selected from F or Cl.

6. The compound of claim 4, or pharmaceutically acceptable salt thereof, wherein $R^5$ is hydrogen.

7. The compound of claim 6, or pharmaceutically acceptable salt thereof wherein $R^6$ is —C(=O)OH.

8. The compound of claim 7, or pharmaceutically acceptable salt thereof, wherein X is C(H).

9. The compound of claim 8, or pharmaceutically acceptable salt thereof, wherein $R^2$ is hydrogen.

10. The compound of claim 8, or pharmaceutically acceptable salt thereof, wherein $R^2$ is methyl.

11. The compound of claim 8, or pharmaceutically acceptable salt thereof, wherein $R^3$ is hydrogen.

12. The compound of claim 8, or pharmaceutically acceptable salt thereof, wherein $R^3$ is methyl.

13. The compound of claim 1, or pharmaceutically acceptable salt thereof, wherein
$R^2$ is hydrogen;
$R^3$ is hydrogen;
$R^4$ is methyl;
$R^5$ is methyl;
$R^6$ is —C(=O)OH; and
X is C(H).

14. The compound of claim 13, or pharmaceutically acceptable salt thereof, wherein $R^1$ is $(C_1-C_6)$alkyl substituted with 1 to 3 substituents selected from the group consisting of halo, hydroxy, —$NH_2$, —C(=O)$NH_2$, and a 3 to 7 membered heterocycle, wherein said heterocycle contains 1 to 3 heteroatoms independently selected from O, N, or S.

15. The compound of claim 13, or pharmaceutically acceptable salt thereof, wherein $R^1$ is $(C_1-C_6)$alkyl substituted with 1 to 3 halo.

16. The compound of claim 13, or pharmaceutically acceptable salt thereof, wherein $R^1$ is $(C_1-C_6)$alkyl substituted with 1 to 3 hydroxy.

17. The compound of claim 13, or pharmaceutically acceptable salt thereof, wherein $R^1$ is a 3-7 membered heterocycle, wherein said heterocycle contains 1 to 3 heteroatoms independently selected from O, N, or S.

18.

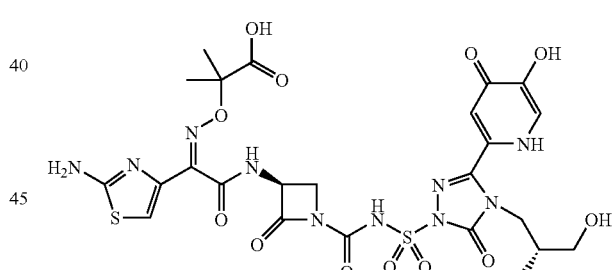

or a pharmaceutically acceptable salt thereof.

19.

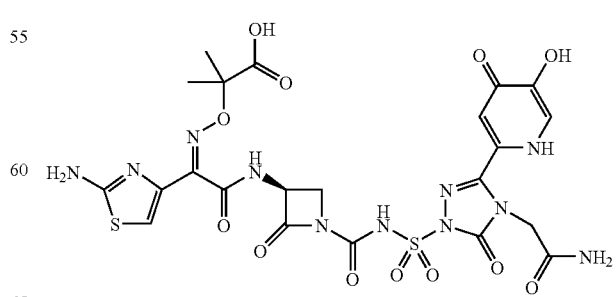

or a pharmaceutically acceptable salt thereof.

20.
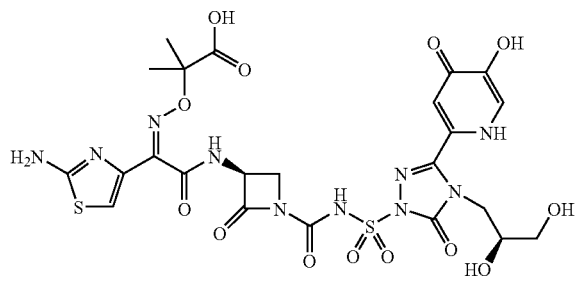
or a pharmaceutically acceptable salt thereof.
21.
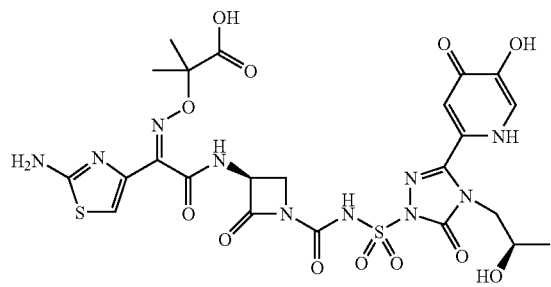
or a pharmaceutically acceptable salt thereof.
22.
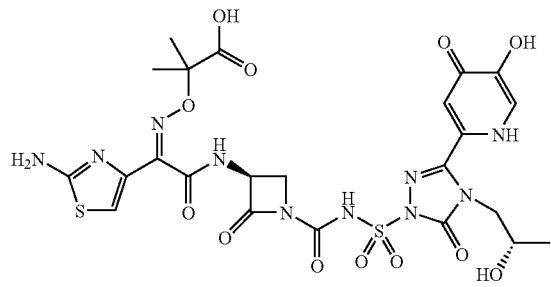
or a pharmaceutically acceptable salt thereof.
23. A compound of formula (IB):
(IB)
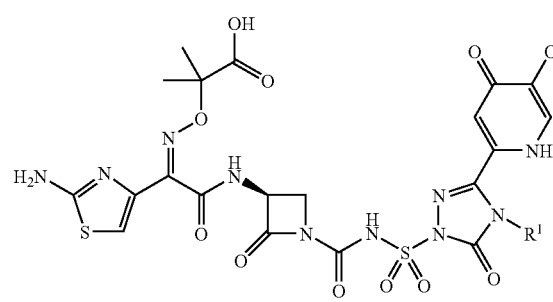
wherein R¹ is selected from the group consisting of:
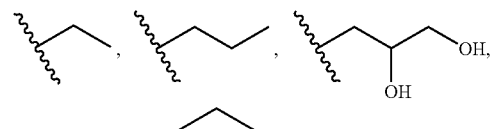
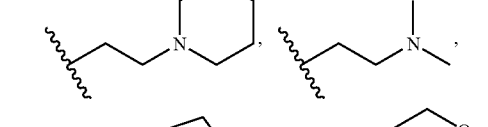
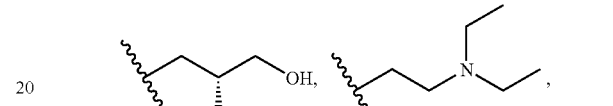
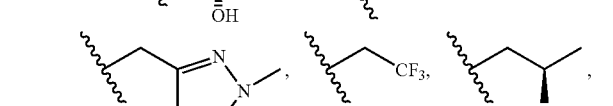
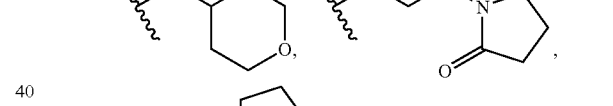
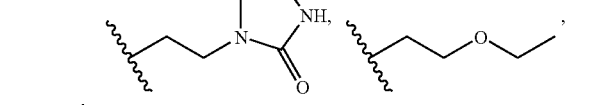
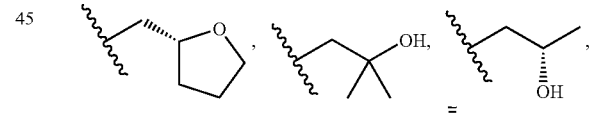
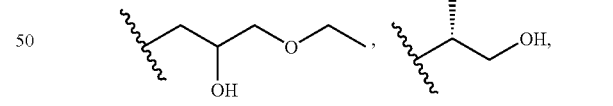
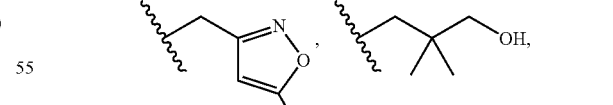
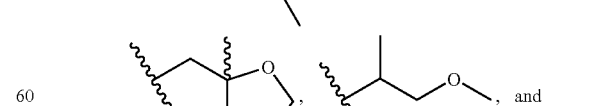
and pharmaceutically acceptable salts thereof.

24. A pharmaceutical composition comprising the compound of claim 1, or pharmaceutically acceptable salt thereof, and a pharmaceutically acceptable carrier.

25. A method for the treatment of a bacterial infection in a mammal comprising administering to said mammal an amount of a compound of formula (I) or pharmaceutically acceptable salt thereof of claim 1 that is effective in treating a bacterial infection.

* * * * *